US007858347B2

(12) United States Patent
Cunningham

(10) Patent No.: US 7,858,347 B2
(45) Date of Patent: Dec. 28, 2010

(54) **COMPOSITIONS AND METHODS FOR DETERMINING THE PRESENCE OF *CHLAMYDOPHILA PNEUMONIAE* IN A TEST SAMPLE**

(75) Inventor: Melissa M. Cunningham, Sliema (MT)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 12/364,295

(22) Filed: Feb. 2, 2009

(65) Prior Publication Data

US 2009/0220981 A1 Sep. 3, 2009

Related U.S. Application Data

(62) Division of application No. 11/448,531, filed on Jun. 6, 2006, now Pat. No. 7,498,137.

(60) Provisional application No. 60/688,127, filed on Jun. 6, 2005.

(51) Int. Cl.
*C12Q 1/68* (2006.01)
*C12P 19/34* (2006.01)
*C07H 21/04* (2006.01)

(52) U.S. Cl. ........................ 435/91.2; 435/6; 435/91.1; 536/24.3; 536/24.33

(58) Field of Classification Search ....................... None
See application file for complete search history.

(56) References Cited

U.S. PATENT DOCUMENTS

| | | | |
|---|---|---|---|
| 4,851,330 | A | 5/1989 | Kohne |
| 5,030,557 | A | 7/1991 | Hogan et al. |
| 5,185,439 | A | 2/1993 | Arnold, Jr. et al. |
| 5,281,518 | A | 1/1994 | Campbell et al. |
| 5,283,174 | A | 2/1994 | Arnold et al. |
| 5,350,673 | A | 9/1994 | Campbell et al. |
| 5,374,718 | A | 12/1994 | Hammond et al. |
| 5,399,491 | A | 3/1995 | Kacian et al. |
| 5,683,870 | A | 11/1997 | Hammond et al. |
| 5,840,488 | A | 11/1998 | Hogan et al. |
| 5,925,517 | A | 7/1999 | Tyagi et al. |
| 6,110,678 | A | 8/2000 | Weisburg et al. |
| 6,130,038 | A | 10/2000 | Becker et al. |
| 6,210,876 | B1 | 4/2001 | Cerney |
| 6,261,769 | B1 | 7/2001 | Everett et al. |
| 6,361,945 | B1 | 3/2002 | Becker |
| 6,379,892 | B1 | 4/2002 | Kacena |
| 6,559,294 | B1 | 5/2003 | Griffais et al. |
| 6,682,889 | B1 | 1/2004 | Wang et al. |
| 7,250,496 | B2 | 7/2007 | Bentwich |
| 2002/0168633 | A1 | 11/2002 | Mabilat et al. |
| 2005/0228172 | A9 | 10/2005 | Wang |
| 2006/0046265 | A1 | 3/2006 | Becker et al. |
| 2007/0031844 | A1 | 2/2007 | Khvorova et al. |

FOREIGN PATENT DOCUMENTS

| | | | |
|---|---|---|---|
| EP | 0 587 331 | A1 | 3/1994 |
| EP | 0 732 408 | A2 | 9/1996 |
| WO | WO90/15159 | A2 | 12/1990 |
| WO | WO95/32305 | A1 | 11/1995 |
| WO | WO98/55646 | A1 | 12/1998 |
| WO | WO99/27105 | A2 | 6/1999 |
| WO | WO2004/029300 | A2 | 4/2004 |

OTHER PUBLICATIONS

Database Genbank, Accession No. AR310754, Version No. AR310754.1, "*Chlamydia pneumoniae* polynucleotides and uses thereof", Jun. 2003 (U.S. Appl. No. 6/559,294, May 6, 2003).

Database Genbank, Accession No. U76711, Version No. U76711.2, "*Chlarnydophila pneumoniae* strain TW-183 16S ribosomal RNA gene," partial sequence, Jun. 21, 1999.

Abdulkarim at al., "Primary biliary chirrhosis: an infectious disease caused by *Chlamydia pneumoniae*?," J. Hepatol., 2004, 40:380-384, Elsevier Science B.V., United Kingdom.

Apfalter et al., "Multicenter Comparison Trial of DNA Extraction Methods and PCR Assays for Detection of *Chlamydia pneumoniae* in Endarterectomy Specimens," J. Clin. Microbiol., 2001, 39(2):519-524, ASM, USA.

Apfalter et al., "Reliability of Nested PCR for Detection of *Chlamydia pneumoniae* DNA in Atheromas: Results from a Multicenter Study Applying Standardized Protocols," J. Clin. Microbiol., 2002, 40(12):4428-4434, ASM, USA.

Apfalter et al., "Comparison of a New Quantitative *ompA*-Based Real-Time PCR TaqMan Assay for Detection of *Chlamydia pneumoniae* DNA in Respiratory Specimens with Four Conventional PCR Assays," J. Clin. Microbiol., 2003, 41(2):592-600, ASM, USA.

Berger et al., "*Chlamydia pneumoniae* in a Free-Ranging Giant Barred Frog (*Mixophyes iteratus*) from Australia," J. Clin. Microbiol., 1999, 37(7):2378-2380, ASM, USA.

Berger et al., "*Chlamydia pneumoniae* DNA in non-coronary athero-sclerotic plaques and circulating leukocytes," J. Lab. Clin. Med., 2000, 136(3):194-200, Elsevier, USA.

Black et al., "Detection of *Chlamydia pnuemoniae* in Clinical Specimens by Polymerase Chain Reaction Using Nested Primers," Eur. J. Clin. Microbiol. Infect. Dis., 1994, 13:752-756, Springer-Verlag, Germany.

Blasi et al., "Failure to detect the presence of *Chlamydia pneumoniae* in sarcoid pathology specimens," Eur. Respir. J., 1997, 10:2609-2611, European Respiratory Society, Switzerland.

Bodetti et al., "Molecular Evidence to Support the Expansion of the Hostrange of *Chlamydophila pneumoniae* to Include Reptiles as Well as Humans, Horses, Koalas and Amphibians," System. Appl. Microbiol., 2002, 25:146-152, Elsevier, Germany.

(Continued)

*Primary Examiner*—Young J Kim
(74) *Attorney, Agent, or Firm*—Charles B. Cappellari

(57) ABSTRACT

Oligonucleotides for use in determining the presence of *Chlamydophila pneumoniae* in a test sample. The oligonucleotides are incorporated into detection probes, capture probes, and amplification oligonucleotides, and can be used in various combinations thereof.

26 Claims, No Drawings

OTHER PUBLICATIONS

Byrne et al., "*Chlamydia pneumoniae* Expresses Genes Required for DNA Replication but Not Cytokinesis during Persistent Infection of HEP-2 Cells," Infect. Immun., 2001, 69(9):5423-5429, ASM, USA.
Cagli et al., "Failure to detect *Chlamydia pneumoniae* DNA in cerebral aneursymal sac tissue with two different polymerase chain reaction methods," J. Neurol. Neurosurg. Psychiatry, 2003, 74:756-759, BMJ Publishing Group, United Kingdom.
Campbell et al., "Detection of *Chlamydia pneumoniae* by Polymerase Chain Reaction," J. Clin. Microbiol., 1992, 30(2):434-439 ASM, USA.
Chen et al., "Detection of *Chlamydia pneumoniae* by polymerase chain reaction-enzyme immunoassay in intestinal mucosal biopsies from patients with inflammatory bowel diseases and controls," J. Gastroenterol. Hepatol., 2002, 17:987-993, Blackwell Scientific Publications, Australia.
Claas, et al., "Detection of *Chlamydia trachomatis* in Clinical Specimens by the Polymerase Chain Reaction," Eur. J. Clin. Microbiol. Infect. Dis., 1990, 9(12):864-868, Springer-Verlag, Germany.
Contini et al., "Molecular identification and antibody testing of *Chlamydophila pneumonlae* in a subgroup of patients with HIV-associated dementia complex. Preliminary Results," J. Neuroimmunol., 2003, 136:172-177, Elsevier, Holland.
Contini et al., "Cerebrospinal fluid molecular demonstration of *Chlamydia pneumoniae* DNA is associated to clinical and brain magnetic resonance imaging activity in a subset of patients with relapsing-remitting multiple sclerosis," Multiple Sclerosis, 2004, 10:360-369, Sage Publications, United Kingdom.
Corsaro et al., "New parachlamydial 16S rDNA phylotypes detected in human clinical samples," Res. Microbiol., 2002, 153:563-567, Elsevier, Holland.
Daugharty at al., "*Chlamydia* DNA Extraction for Use in PCR: Stability and Sensitivity in Detection," J. Clin. Lab. Anal., 1998, 12:47-53, Wiley-Liss, USA.
Deguchi et al., "Detection of *Chlamydia trachomatis* by Polymerase Chain Reaction," J. Japanese Assoc. Infect. Dis., 1991, 65(9):1183-1187, Japan (English Abstract p. 1187).
Devereaux et al., "Molecular Evidence for Novel *Chlamydial* Infections in the Koala (*Phascolarctos cinereus*)," Syst. Appl. Microbiol., 2003, 26:245-253, Elsevier, Germany.
Dong-Si et al., "Increased prevalence of and gene transcription by *Chlamydia pneumoniae* in cerebrospinal fluid of patients with relapsing-remitting multiple sclerosis," J. Neurol., 2004, 251:542-547, Springer-Verlag, Germany.
Esposito et al., "Demonstration of Viable *Chlamydia pneumoniae* in Atherosclerotic Plaques of Carotid Arteries by Reverse Transcriptase Polymerase Chain Reaction," Ann. Vasc. Surg., 1999, 13(4):421-425, Springer Verlag, USA.
Everett et al., "The Ribosomal Intergenic Spacer and Domain I of the 23S rRNA Gene Are Phylogenetic Markers for *Chlamydia* spp.," Int. J. Syst. Bacteriol., 1997, 47(2):461-473, Society for General Microbiology, United Kingdom.
Everett et al., "Emended description of the order *Chlamydiales*, proposal of *Parachlamydiaceae* fam. nov. and *Simkaniaceae* fam. nov., each containing one monotypic genus, revised taxonomy of the family *Chlamydiaceae*, including a new genus and five new species, and standards for the identification of organisms," Int. J. Syst. Bacteriol., 1999, 49:415-440, Society for General Microbiology, United Kingdom.
Fukano, "Comparison of Five PCR Assays for Detecting *Chlamydophila pneumonlae* DNA," Microbiol. Immunol., 2004, 48(6):441-448, Tokyo Japanese Society for Bacteriology, Tokyo, Japan.
Fukushi et al., "Restriction Fragment Length Polymorphisms of rRNA as Genetic Markers to Differentiate *Chlamydia* spp.," Int. J. Syst. Bacteriol., 1993, 43(3):613-617, Society for General Microbiology, United Kingdom.
Gaydos et al., "Identification of *Chlamydia pneumoniae* by DNA Amplification of the 16S rRNA Gene," J. Clin. Microbiol., 1992, 30(4):796-800, ASM, USA.
Gaydos et al., "Detection of *Chiamydia pneumoniae* by Polymerase Chain Reaction-Enzyme Immunoassay in an Immunocompromised Population," Clin. Infect. Dis., 1993, 17:718-723, The University of Chicago Press, USA.
Gaydos et al., "Phylogenetic Relationship of *Chlamydia pneumoniae* to *Chlamydia psittaci* and *Chlamydia trachomatis* as Determined by Analysis of 16S Ribosomal DNA Sequences," Int. J. Syst. Bacteriol., 1993, 43(3):610-612, Society for General Microbiology, United Kingdom.
Gerard et al., "Cytokine and Chemokine mRNA Produced in Synovial Tissue Chronically Infected with *Chlamydia trachomatis* and *C. pneumoniae*," The Internet Journal of Rheumatology—pp. 1-18, www.irheum.com/subscribers/02/09/1827.html (J. Rheumatol., 2002, 29:1827-1835), Toronto Journal Of Rheumatology Publishing Co., Canada.
Gerard at al., "*Chlamydia pneumoniae* present in the human synovium are viable and metabolically active," Microb. Pathog., 2000, 29:17-24, Academic Press, USA.
Goyal et al., "Is *Chiamydia pneumoniae* Infection Associated with Stroke in Children With Sickle Cell Disease?," Pediatrics, 2004, 113(4):e318-e321, The American Academy of Pediatrics, United Kingdom.
Greub et al., "*Parachlamydiaceae*: Potential Emerging Pathogens," Emerg. Infect. Dis., 2002, 8(6):625-630, National Center for Infectious Diseases, Centers for Disease Control and Prevention (CDC), USA.
Grondahl et al., "Rapid Identification of Nine Microorganisms Causing Acute Respiratory Tract Infections by Single-Tube Multiplex Reverse Transcription-PCR: Feasibility Study," J. Clin. Microbiol., 1999, 37(1):1-7, ASM, USA.
Haranaga et al., "Analysis of *Chlamydia pneumoniae* Growth in Cells by Reverse Transcription-PCR Targeted to Bacterial Gene Transcripts," Clin. Diagn. Lab. Immunol., 2002, 9(2):313-319, ASM, USA.
Haranaga et al., "Detection of *Chlamydia pneumoniae* antigen in PBMNCs of healthy blood donors," Transfusion, 2001, 41:1114-1119, Bethesda MD American Association Of Blood Banks, USA.
Haraszthy et al., "Identification of Periodontal Pathogens in Atheromatous Plaques," J. Periodontol., 2000, 71(10):1554-1560, American Academy of Periodontology, Chicago, USA.
Hardick et al., "Real-Time PCR for *Chlamydia pneumoniae* Utilizing the Roche Lightcycler and a 16S rRNA Gene Target," J. Mol. Diagn., 2004, 6(2):132-136, American Society for Investigative Pathology and the Association for Molecular Pathology, USA.
Herrmann at al., "Characterization of the *rnpB* gene and Rnase P RNA in the order *Chlamydiales*," Int. J. Syst. Evol. Microbiol., 2000, 50:149-158, Society for General Microbiology, United Kingdom.
Hogan et al., "Differential expression of genes encoding membrane proteins between acute and continuous *Chlamydia pneumoniae* infections," Microb. Pathog., 2003, 34:11-16, Elsevier Science Ltd., Australia.
Ieven et al., "Relevance of Nucleic Acid Amplification Techniques for Diagnosis of Respiratory Tract Infections in the Clinical Laboratory," Clin. Microbial. Rev., 1997, 10(2):242-256, ASM, USA.
Jacobson et al., "Identification of *Chlamydophila pneumoniae* in an emerald tree boa, *Corallus caninus*," J. Vet. Diagn. Invest., 2004, 16:153-154, Journal of veterinary diagnostic investigation American Association of Veterinary Laboratory Diagnosticians (Aavld), USA.
Jantos et al., "Rapid Detection of *Chlamydia pneumoniae* by PCR-Enzyme Immunoassay," J. Clin. Microbiol., 1998, 36(7)1890-1894, ASM, USA.
Jantos et al., "Low Prevalence of *Chlamydia pneumoniae* in Atherectomy Specimens from Patients with Coronary Heart Disease," Clin. Infect. Dis., 1999, 28:988-992, The University of Chicago Press, USA.
Jensen et al., "Detection of *Mycoplasma genitalium* by PCR Amplification of the 16S rRNA Gene," J. Clin. Microbiol., 2003, 41(1):261-266, ASM, USA.
Kitumnuaypong et al., "Is there a role for *Chlamydia pneumoniae* infection in systemic lupus erythematosus and in the associated atherosclerotic cardiovascular disease?," Clin. Exp. Rheumatol., 2004, 22:339-342, Pisa Clinical And Experimental Rheumatology S.A.S., Italy.

Kornak et al., "Sequence Analysis of the Gene Encoding the *Chlamydia pneumoniae* DnaK Protein Homolog," Infect. Immun., 1991, 59(2):721-725, ASM, USA.

Kraube-Opatz et al., "Frequent contamination of *Chlamydia trachomatis* and *Chlamydia pneumoniae* strains with mycoplasma. Biological relevance and selective eradication of mycoplasma from chlamydial cultures with mupirocin," Med. Microbial. Immunol., 2000, 189:19-26, Springer-Verlag, Germany.

Kuo et al., "Demonstration of *Chlamydia pneumoniae* in Atherosclerotic Lesions of Coronary Arteries," J. Infect. Dis., 1993, 167:841-849, University of Chicago Press, USA.

Leung et al., "Is there a Relation between *Chlamydia* Infection and Primary Biliary Cirrhosis?," Clin. Dev. Immunol., 2003, 10(2-4):227-233, Taylor & Francis Health Sciences, United Kingdom.

Madico et al., "Touchdown Enzyme Time Release-PCR for Detection and Identification of *Chlamydia trachomatis, C. pneumoniae*, and *C. psittaci* Using the 16S and 16S-23S Spacer rRNA Genes," J. Clin. Microbiol., 2000, 38(3):1085-1093, ASM, USA.

Mahony et al., "Analytical Sensitivity, Reproducibility of Results, and Clinical Performance of Five PCR Assays for Detecting *Chlamydia pneumoniae* DNA in Peripheral Blood Mononuclear Cells," J. Clin. Microbiol., 2000, 38(7):2622-2627, ASM, USA.

Maraha et al., "Is the Perceived Association between *Chlamydia pneumoniae* and Vascular Diseases Biased by Methodology?," J. Clin. Microbiol., 2004, 42(9):3937-3941, ASM, USA.

Meijer et al., "Species Identification of *Chlamydia* Isolates by Analyzing Restriction Fragment Length Polymorphism of the 165-23S rRNA Spacer Region," J. Clin. Microbiol., 1997, 35(5); 1179-1183, ASM, USA.

Meijer et al., "Genomic Relatedness of *Chlamydia* Isolates Determined by Amplified Fragment length Polymorphism Analysis," J. Bacteriol., 1999, 181(15):4469-4475, ASM, USA.

Meijer et al., "*Chlamydia pneumoniae* in vitro and in vivo: a critical evaluation of in situ detection methods," J. Clin. Pathol., 2000, 53:904-910, BMJ Pub. Group, United Kingdom.

Meijer et al., "*Chlamydia pnuemoniae* antigens, rather than viable bacteria, persist in atherosclerotic lesions," J. Clin. Pathol., 2000, 53:911-916, BMJ Pub. Group, United Kingdom.

Melgosa et al., "Sequence Analysis of the Major Outer Membrane Protein Gene of *Chlamydia pneumoniae*," Infect. Immun., 1991, 59(6):2195-2199, ASM, USA.

Metogho et al., "Comparison of PCR protocols including positive controls for detection of *Chlamydia pneumoniae* in respiratory specimens," Mol. Cell. Probes, 1999, 13:71-75, Academic Press Limited, USA.

Messmer et al., "Application of a Nested, Multiplex PCR to Psittacosis Outbreaks," J. Clin. Microbiol., 1997, 35(8):2043-2046, ASM, USA.

Olmez et al., "Chlamydial Nucleic Acids in Synovium in Osteoarthritis: What Are the Implications?," J. Rheumatol., 2001, 28:(8):1874-1880, Toronto Journal of Rheumatology Publishing Co., Canada.

Pettersson et al., "Evolutionary Relationships among Members of the Genus *Chlamydia* Based on 16S Ribosomal DNA Analysis," J. Bacteriol., 1997, 179(13):4195-4205, ASM, USA.

Pham et al., "Use of Lambda Phage DNA as a Hybrid Internal Control in a PCR-Enzyme Immunoassay to Detect *Chlamydia pneumoniae*," J. Clin. Microbiol., 1998, 36(7):1919-1922, ASM, USA.

Poppert et al., "Detection and Differentiation of Chlamydiae by Fluorescence In Situ Hybridization," Appl. Environ. Microbiol., 2002, 68(8):4081-4089, ASM, USA.

Pudjiatmoko et al., "Phylogenetic Analysis of the Genus *Chlamydia* Based on 16S rRNA Gene Sequences," Int. J. Syst. Bacteriol., 1997, 47(2):425-431, Society for General Microbiology, United Kingdom.

Ramirez et al., "Diagnosis of *Legionella pneumophila, Mycoplasma pneumoniae*, or *Chlamydia pneumoniae* Lower Respiratory Infection Using the Polymerase Chain Reaaction on a Single Throat Swab Specimen," Diagn. Microbiol. Infect. Dis., 1996, 24:7-14, Elsevier Biomedical, USA.

Rasmussen et al., "PCR detection and differentiation of *Chlamydia pneumoniae, Chlamydia psittaci* and *Chlamydia trachomatis*," Mol. Cell. Probes, 1992, 6:389-394, Academic Press Limited, USA.

Reed et al., "*Chlamydia pneumoniae* Infection in a Breeding Colony of African Clawed Frogs (*Xenopus tropicalis*)," Emerg. Infect. Dis., 2000, 6(2):196-199, National Center for Infectious Diseases Centers for Disease Control and Prevention (CDC), USA.

Regan et al., "Temporal Arteritis and *Chlamydia pneumoniae*," Arthritis Rheum., 2002, 46(4)1056-1060, Wiley-Liss, Inc., USA.

Rurangirwa et al., "Analysis of the 16S rRNA gene of micro-organism WSU 86-1044 from an aborted bovine foetus reveals that it is a member of the order *Chlamydiales*:proposal of *Waddliaceae* fam. nov., *Waddlia chondrophila* gen. nov., sp. nov.," Int. J. Syst. Bacteriol., 1999, 49:577-581, Society for General Microbiology, United Kingdom.

Schumacher et al., "*Chlamydia trachomatis* Nucleic Acids can be Found in the Synovium of Some Asymptomatic Subjects," Arthritis Rheum., 1999, 42(6):1281-1284, Wiley-Liss, Inc., USA.

Schumacher et al., "Lower Prevalence of *Chlamydia pneumoniae* DNA Compared with *Chlamydia trachomatis* DNA in Synovial Tissue of Arthritis Patients," Arthritis Rheum., 1999, 42(9):1889-1893, Wiley-Liss, Inc., USA.

Scieux et al., "DNA fingerprinting of *Chlamydia trachomatis* by use of ribosomal RNA, oligonucleotide and randomly cloned DNA probes," Res. Microbiol., 1992, 143:755-765, Elsevier, Amsterdam.

Scieux et al., "Molecular typing of *Chlamydia trachomatis* by random amplification of polymorphic DNA," Res. Microbiol., 1993, 144:395-404, Elsevier, Amsterdam.

Sheehy et al., "Analysis of partial 16S rRNA nucleotide sequences of *Chlamydia pecorum* and *C. psittaci*," FEMS Immunol. Med. Microbial., 1997, 17:201-205, Elsevier Science, B.V., Amsterdam.

Smith et al., "In Vitro Activities of Garenoxacin andLevofioxacin against *Chlamydia pneumoniae* Are Not Affected by Presence of *Mycoplasma* DNA," Antimicrob. Agents Chemother., 2004, 48(6):2081-2084, ASM, USA.

Sun et al., "Studies on the infection status of seven species—three species of *Chlamydia, Neisseria gonorrhoeae* and *Garderella vaginalis* in 76 patients with sexual transmitted diseases," Chinese J. Epidemiol., 2004, 25(2):146-149, Chinese Medical Assoc., China (English Abstract).

Taylor-Robinson et al., "Oro-Dental Bacteria in Various Atherosclerotic Arteries," Eur. J. Clin. Microbial. Infect. Dis., 2002, 21:755-757, Springer-Verlag, Germany.

Tondella et al., "Development and Evaluation of Real-Time PCR-Based Fluorescence Assays for Detection of *Chlamydia pneumoniae*," J. Clin. Microbial., 2002, 40(2):575-583, ASM, USA.

Toyokawa et al., "Severe *Chlamydophila psittaci* pneumonia rapidly by detection of antigen in sputum with an immunochromatography assay," J. Infect. Chemother., 2004, 10:245-249, Springer-Verlag, Japan.

Tran et al., "Absence of *Porphyromonas asaccharolytica, Bacteroides fragilis* and *Chlamydia pneumoniae* in human subgingival plaque," Oral Microbiol. Immunol., 1997, 12:377-378, Copenhagen Munksgaard International Publishers, Denmark.

Valassina et al., "Search for *Chlamydia pneumoniae* genes and their expression in atherosclerotic plaques of carotid arteries," J. Med. Microbial., 2001, 50:228-232, London Lippincott Williams And Wilkins, United Kingdom.

Verkooyen et al., "Widely used, commercially available *Chlamydia pneumoniae* antigen contaminated with mycoplasma," J. Med. Microbial., 1997, 46:419-424, London Lippincott Williams And Wilkins, United Kingdom.

Wardrop et al., "Characterization of the Koala Biovar of *Chlamydia pneumoniae* at Four Gene Loci—ompAVD4, ompB, 16S rRNA, groESL Spacer Region," Syst. Appl. Microbiol., 1999, 22:22-27, G. Fischer Verlag, Germany.

Watt et al., "Viral and Bacterial DNA in Carotid Atherosclerotic Lesions," Eur. J. Clin. Microbiol. Infect. Dis., 2003, 22:99-105, Springer-Verlag, Germany.

Wilson et al., "Development of a simplified polymerase chain reaction-enzyme immunoassay for the detection of *Chlamydia pneumoniae*," J. Appl. Bacteriol., 1996, 80:431-438, Oxford Blackwell Scientific Publications, United Kingdom.

Wozniak et al., "Absence of *Chlamydia pneumoniae* in brain of vascular dementia patients," Neurobiol. Aging, 2003, 24:761-765, Elsevier, USA.

Yamaguchi et al., "Prevalence of viable *Chlamydia pneumoniae* in peripheral blood mononuclear cells of healthy blood donors," Transfusion, 2004, 44:1072-1078, Bethesda MD American Association Of Blood Banks, USA.

PCT International Search Report , Application No. PCT/US2006/022392, Dec. 13, 2006.

PCT International Preliminary Report on Patentability, International Application No. PCT/US2006/022392, Dec. 21, 2007.

EPO Office Action, European Patent Application No. 06772632.3, Jan. 27, 2010.

COMPOSITIONS AND METHODS FOR DETERMINING THE PRESENCE OF *CHLAMYDOPHILA PNEUMONIAE* IN A TEST SAMPLE

CROSS-REFERENCE TO RELATED APPLICATIONS

This application is a division of U.S. application Ser. No. 11/448,531, filed Jun. 6, 2006, now U.S. Pat. No. 7,498,137, which claims the benefit of U.S. Provisional Application No. 60/688,127, filed Jun. 6, 2005, each of which applications is hereby incorporated by reference herein.

FIELD OF THE INVENTION

The present invention relates to detection probes, capture probes, amplification oligonucleotides, nucleic acid compositions, methods, and kits useful for determining the presence of *Chlamydophila pneumoniae* (also known as *Chlamydia pneumoniae*) in a test sample.

BACKGROUND OF THE INVENTION

*Chlamydophila pneumoniae* is an obligate intracellular bacterium and is known to be a common cause of community-acquired pneumonia (CAP). While *pneumoniae* and bronchitis are most commonly associated with *C. pneumoniae* infections, other possible illnesses include pharyngitis, laryngitis, sinusitis and otitis. Most cases of pneumonia are relatively mild, but *C. pneumoniae* can cause severe disease requiring hospitalization. In the United States alone, there are approximately 50,000 pneumonia-related hospitalizations a year which are caused by a *C. pneumoniae* infection. Humans are the only known reservoir of this organism, and transmission is person-to-person by respiratory secretions.

A number of studies have also demonstrated an epidemiological link between *C. pneumoniae* infection and atherosclerosis. Although it has been shown that *C. pneumoniae* has the capacity to infect smooth muscle cells found within atherosclerotic lesions, it is still not known what role the organism plays in the pathogenesis of atherosclerosis. Associations with Alzheimer's disease, asthma and reactive arthritis have also been proposed.

Presently, there are no standardized diagnostic methods for detecting *C. pneumoniae* infections, and means for performing rapid diagnosis are not readily accessible. Diagnostic techniques which have been employed include serologic antibody tests, cell culture, antigen detection and PCR-based nucleic acid amplification assays. The most commonly used serologic assay is the microimmuno-fluorescent (MIF) test but it requires significant skill to evaluate appropriate fluorescence, has not been well standardized, and may be less reliable in the serodiagnosis of children than adults. Culture is difficult because the organism is fastidious and takes considerable time to grow. Antigen detection is relatively insensitive and has been shown to have substantial cross-reactivity with other chlamydias. PCR systems for detecting *C. pneumoniae* have considerable problems with contamination, inhibitors, specificity and assay complexity. Consequently, most pneumonia diagnoses are made empirically, and the prescribed treatment is generally a B-lactam antibiotic for targeting *Streptococcus pneumoniae*. While the majority of pneumonias respond to B-lactam antibiotics, atypical pneumonias like *C. pneumoniae* do not, instead requiring treatment with macrolide. As a result, empirical diagnosis can lead to inappropriate antibiotic treatments with increased drug resistance and health care costs, as well as disease progression. Thus, a need exists for a sensitive and specific test for rapidly diagnosing *C. pneumoniae* infections.

SUMMARY OF THE INVENTION

The present invention provides a solution to the clinical need for a sensitive assay specific for *C. pneumoniae* by featuring oligonucleotides that are useful for determining whether *C. pneumoniae* is present in a test sample, such as a conjunctiva or respiratory specimen. The featured oligonucleotides may be contained in detection probes, capture probes and/or amplification oligonucleotides that are useful for detecting, immobilizing and/or amplifying *C. pneumoniae* target nucleic acid present in a test sample.

In one embodiment, detection probes are provided that can preferentially hybridize to a target region present in nucleic acid derived from 23S ribosomal nucleic acid of *C. pneumoniae* to form a detectable probe:target hybrid that indicates the presence of *C. pneumoniae* in a test sample. Preferred detection probes of this embodiment include a target binding region that stably hybridizes, under stringent hybridization conditions, to a target sequence contained within a target region selected from the group consisting of:

SEQ ID NO: 1 gctaacacaaggtcgggttgtggttaagggaa,

SEQ ID NO: 2 gcuaacacaaggucggguugugguuaagggaa,

SEQ ID NO: 3 ttcccttaaccacaacccgaccttgtgttagc,
and

SEQ ID NO: 4 uucccuuaaccacaacccgaccuuguguuagc.

The base sequence of the target binding region of the preferred detection probes comprises at least 12, 13, 14 or 15 of 15 contiguous bases of a reference sequence (i.e., the exact complement of a target sequence) selected from the group consisting of:

| | |
|---|---|
| SEQ ID NO: 5 | gctaacacaaggtcg, |
| SEQ ID NO: 6 | gcuaacacaaggucg, |
| SEQ ID NO: 7 | cgaccttgtgttagc, |
| SEQ ID NO: 8 | cgaccuuguguuagc, |
| SEQ ID NO: 9 | gctaacacaaggtcgggttg, |
| SEQ ID NO: 10 | gcuaacacaaggucggguug, |
| SEQ ID NO: 11 | caacccgaccttgtgttagc, |
| SEQ ID NO: 12 | caacccgaccuuguguuagc, |
| SEQ ID NO: 13 | caaggtcgggttgtggttaag, |
| SEQ ID NO: 14 | caaggucggguugugguuaag, |
| SEQ ID NO: 15 | cttaaccacaacccgaccttg, |
| SEQ ID NO: 16 | cuuaaccacaacccgaccuug, |
| SEQ ID NO: 17 | caaggtcgggttgtggttaaggg, |
| SEQ ID NO: 18 | caaggucggguugugguuaaggg, |
| SEQ ID NO: 19 | cccttaaccacaacccgaccttg, |
| SEQ ID NO: 20 | cccuuaaccacaacccgaccuug, |

-continued

```
SEQ ID NO: 21    caaggtcgggttgtggttaagggaa,

SEQ ID NO: 22    caaggucggguugugguuaagggaa,

SEQ ID NO: 23    ttcccttaaccacaacccgaccttg,
and

SEQ ID NO: 24    uucccuuaaccacaacccgaccuug.
```

Detection probes according to the present invention preferentially hybridize to the target nucleic acid and not to nucleic acid derived from non-*C. pneumoniae* organisms present in a test sample under stringent hybridization conditions. In particular, the detection probes of the present invention preferentially hybridize to the target nucleic acid and not to nucleic acid derived from *Chlamydia trachomatis* or *Chlamydophila psittaci* (also known as *Chlamydia psittaci*), which are considered to be the most closely related organisms to *C. pneumoniae*. For testing purposes, *C. trachomatis* and *C. psittaci* can be obtained from the American Type Culture Collection in Manassas, Va. as, for example, ATCC Nos. VR-878 and VR-601, respectively.

A detection probe according to the present invention may have a target binding region of any length suitable to achieve the desired selectivity and specificity for *C. pneumoniae*-derived nucleic acid. The base sequence of the target binding region is preferably between 12, 13, 14 or 15 and 35 bases in length, and more preferably between 15 and 25 bases in length. The base sequence of the detection probe is preferably up to 15, 20, 25, 30, 35, 40, 50 or 100 bases in length. Preferably, the target binding region of the detection probe comprises, overlaps with, consists essentially of, substantially corresponds to, consists of, or is contained within the reference sequence. More preferably, the base sequence of the detection probe consists essentially of, substantially corresponds to, consists of, or is contained within the reference sequence. In a preferred embodiment, the detection probe fully hybridizes to a target sequence substantially corresponding to, consisting of; or contained within the target region. As used herein, the phrase "fully hybridizes" means that the referred to probe or oligonucleotide does not stably hybridize, under assay conditions (e.g., stringent hybridization or amplification conditions), to a region of the target nucleic acid separate from or that extends beyond the boundaries of the target region or sequence.

The target binding region may consist of deoxyribonucleic acid (DNA), ribonucleic acid (RNA), a combination DNA and RNA, or it may be, in whole or in part, a nucleic acid analog having, for example, a modified backbone (e.g., a peptide nucleic acid), a modified sugar moiety (e.g., 2'-O-methyl ribose substitution), a base analog (e.g., inosine), or a known derivative of a purine or pyrimidine base (e.g., deaza- or aza-purines and deaza- or aza-pyrimidines). The target binding region may additionally include molecules that do not hydrogen bond to adenine, cytosine, guanine, thymine or uracil, provided such molecules do not interfere with the ability of the detection probe to selectively and specifically bind to nucleic acid derived from *C. pneumoniae* in the test sample. Examples of such molecules include abasic nucleotides and universal base analogues, such as 5-nitroindole, provided such molecules do not significantly affect duplex stability. See, e.g., Guo et al., "Artificial Mismatch Hybridization," U.S. Pat. No. 5,780,233, the contents of which are hereby incorporated by reference herein.

A detection probe of the present invention may include one or more base sequences in addition to the base sequence of the target binding region which do not stably bind to nucleic acid derived from *C. pneumoniae* under stringent hybridization conditions. An additional base sequence may be comprised of any desired base sequence, so long as it does not stably bind to nucleic acid derived from the *C. pneumoniae* under stringent hybridization conditions or prevent stable hybridization of the probe to the target nucleic acid. By way of example, an additional base sequence may constitute the immobilized probe binding region of a capture probe, where the immobilized probe binding region is comprised of, for example, a 3' poly dA (adenine) region which hybridizes under stringent hybridization conditions to a 5' poly dT (thymine) region of a polynucleotide bound directly or indirectly to a solid support. An additional base sequence might also be a 5' sequence recognized by a RNA polymerase or which enhances initiation or elongation by an RNA polymerase (e.g., a T7 promoter). More than one additional base sequence may be included if the first sequence is incorporated into, for example, a self-hybridizing probe (i.e., a probe having distinct base regions capable of hybridizing to each other in the absence of a target sequence under the conditions of an assay), such as a "molecular beacon" probe. Molecular beacons are disclosed by Tyagi et at, "Detectably Labeled Dual Conformation Oligonucleotide Probes, Assays and Kits," U.S. Pat. No. 5,925,517 (the contents of which are hereby incorporated by reference herein), and include a target binding region which is bounded by or overlaps with two base sequences having regions, referred to as "stems" or "arms," which are at least partially complementary to each other. A more detailed description of molecular beacons is provided infra in the section entitled "Detection Probes to *Chlamydophila pneumoniae* Ribosomal Nucleic Acid." An additional base sequence may be joined directly to the target binding region or, for example, by means of a non-nucleotide linker (e.g., polyethylene glycol or an abasic region).

While not required, detection probes of the present invention preferably include at least one detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester (AE), preferably 4-(2-succinimidyloxycarbonyl ethyl)-phenyl-10-methylacridinium-9-carboxylate fluorosulfonate (hereinafter referred to as "standard AE"). The label may be part of a group of interacting labels useful with a probe pair (see, e.g., Morrison, "Competitive Homogeneous Assay," U.S. Pat. No. 5,928,862, the contents of which are hereby incorporated by reference herein) or a self-hybridizing probe (see, e.g., Tyagi et al., U.S. Pat. No. 5,925,517). Groups of interacting labels include, but are not limited to, enzyme/substrate, enzyme/cofactor, luminescent/quencher, luminescent/adduct, dye dimers and Förrester energy transfer pairs. An interacting luminescent/quencher pair, such as fluoroscein and DABCYL, is particularly preferred.

The invention also contemplates compositions comprising stable nucleic acid duplexes formed between any of the above-described detection probes and the target nucleic acids for the probes under stringent hybridization conditions.

In another embodiment of the present invention, a capture probe is provided for isolating and purifying target nucleic acid derived from *C. pneumoniae* present in a test sample. Preferred capture probes of this embodiment include a target binding region that stably hybridizes, under assay conditions, to a target sequence that is derived from 23S ribosomal nucleic acid of *C. pneumoniae* and is contained within a target region selected from the group consisting of:

```
SEQ ID NO: 25  gttaaatattcctgtaccacctaaaactttagc,

SEQ ID NO: 26  guuaaauauuccuguaccaccuaaaacuuuagc,

SEQ ID NO: 27  gctaaagttttaggtggtacaggaatatttaac,
               and

SEQ ID NO: 28  gcuaaaguuuuaggugguacaggaauauuuaac.
```

The base sequence of the target binding region of the preferred capture probes comprises an at least 12, 13, 14 or 15 of 15 contiguous base region of a reference sequence selected from the group consisting of:

```
SEQ ID NO: 29   gttttaggtggtacaggaatatttaac,

SEQ ID NO: 30   guuuuaggugguacaggaauauuuaac,

SEQ ID NO: 31   gttaaatattcctgtaccacctaaaac,

SEQ ID NO: 32   guuaaauauuccuguaccaccuaaaac,

SEQ ID NO: 33   gctaaagttttaggtggtacagg,

SEQ ID NO: 34   gcuaaaguuuuaggugguacagg,

SEQ ID NO: 35   cctgtaccacctaaaactttagc,
                and

SEQ ID NO: 36   ccuguaccaccuaaaacuuuagc.
```

A capture probe according to the present invention is preferably up to 100 bases in length and the target binding region is preferably up to 20, 25, 30, 35 or 40 bases in length. More preferably, the target binding region of the capture probe comprises, consists essentially of, substantially corresponds to, consists of, or is contained within one of the reference sequences. In a preferred embodiment, the capture probe fully hybridizes to a target sequence substantially corresponding to, consisting of, or contained within one of the target regions.

Capture probes of the present invention may be immobilized on a solid support by means of ligand-ligate binding pairs, such as avidin-biotin linkages, but preferably include an immobilized probe binding region. The immobilized probe binding region of the preferred capture probes is comprised of any base sequence capable of stably hybridizing under assay conditions to an oligonucleotide that is bound to a solid support present in a test sample. Preferably, the immobilized probe binding region is a poly dA, homopolymer tail located at the 3' end of the capture probe. In this embodiment, oligonucleotides bound to the solid support would include 5' poly dT tails of sufficient length to stably bind to the poly dA tails of the capture probes under assay conditions. In a preferred embodiment, the immobilized probe binding region includes a poly dA tail which is about 30 adenines in length, and the capture probe includes a spacer region which is about 3 thymines in length for joining together the target binding region and the immobilized probe binding region.

The present invention also features amplification oligonucleotides useful for determining the presence of *C. pneumoniae* in an amplification assay. In a preferred embodiment, at least one amplification oligonucleotide for amplifying *C. pneumoniae*-derived nucleic acid in a test sample is provided, where the at least one amplification oligonucleotide is a first amplification oligonucleotide having a target binding region that stably binds, under amplification conditions, to a target sequence derived from 23 ribosomal nucleic acid of *C. pneumoniae* and contained within a first target region selected from the group consisting of:

```
SEQ ID NO: 37
gtggttaagggaaatcttcggaggaactgatagtgtggcgcaaggctttc,

SEQ ID NO: 38
gugguuaagggaaaucuucggaggaacugauagugug gcgcaaggcuuuc,

SEQ ID NO: 39
gaaagccttgcgccacactatcagttcctccgaagatttcccttaaccac,
and

SEQ ID NO: 40
gaaagccuugcgccacacuaucaguuccuccgaagauuucccuuaaccac.
```

The base sequence of the target binding region of the first amplification oligonucleotide preferably comprises at least 12, 13, 14 or 15 of 15 contiguous bases of a first reference sequence (i.e., the exact complement of a target sequence of the first target region) selected from the group consisting of:

```
SEQ ID NO: 41    ctccgaagatttcccttaaccac,

SEQ ID NO: 42    cuccgaagauuucccuuaaccac,

SEQ ID NO: 43    gtggttaagggaaatcttcggag,

SEQ ID NO: 44    gugguuaagggaaaucuucggag,

SEQ ID NO: 45    cacactatcagttcctccgaag,

SEQ ID NO: 46    cacacuaucaguuccuccgaag,

SEQ ID NO: 47    cttcggaggaactgatagtgtg,

SEQ ID NO: 48    cuucggaggaacugauagugug,

SEQ ID NO: 49    ccacactatcagttcctcc,

SEQ ID NO: 50    ccacacuaucaguuccucc,

SEQ ID NO: 51    ggaggaactgatagtgtgg,

SEQ ID NO: 52    ggaggaacugauagugugg,

SEQ ID NO: 53    gcgccacactatcagttc,

SEQ ID NO: 54    gcgccacacuaucaguuc,

SEQ ID NO: 55    gaactgatagtgtggcgc,

SEQ ID NO: 56    gaacugauagugugg cgc,

SEQ ID NO: 57    ccttgcgccacactatcagttc,

SEQ ID NO: 58    ccuugcgccacacuaucaguuc,

SEQ ID NO: 59    gaactgatagtgtggcgcaagg,

SEQ ID NO: 60    gaactgatagtgtggcgcaagg,

SEQ ID NO: 61    cttgcgccacactatcag,

SEQ ID NO: 62    cuugcgccacacuaucag,

SEQ ID NO: 63    ctgatagtgtggcgcaag,

SEQ ID NO: 64    cugauagugug gcgcaag,
```

-continued

SEQ ID NO: 65 ccttgcgccacactatc,

SEQ ID NO: 66 ccuugcgccacacuauc,

SEQ ID NO: 67 gatagtgtggcgcaagg,

SEQ ID NO: 68 gauaguguggcgcaagg,

SEQ ID NO: 69 gaaagccttgcgccacactat,

SEQ ID NO: 70 gaaagccuugcgccacacuau,

SEQ ID NO: 71 atagtgtggcgcaaggctttc,
and

SEQ ID NO: 72 auaguguggcgcaaggcuuuc.

In another preferred embodiment, the at least one amplification oligonucleotide for amplifying *C. pneumoniae*-derived nucleic acid present in a test sample is a second amplification oligonucleotide having a target binding region that stably binds, under amplification conditions, to a target sequence derived from 23S ribosomal nucleic acid of *C. pneumoniae* and contained within a second target region selected from the group consisting of:

SEQ ID NO: 73 cggagtacgttaagcacgcggacgattggaaat,

SEQ ID NO: 74 cggaguacguuaagcacgcggacgauuggaaat,

SEQ ID NO: 75 atttccaatcgtccgogtgcttaacgtactccg,
and

SEQ ID NO: 76 atttccaaucguccgcgugcuuaacguacuccg.

The base sequence of the target binding region of the second amplification oligonucleotide preferably comprises at least 12, 13, 14 or 15 of 15 contiguous bases of a reference sequence (i.e., the exact complement of a target sequence of the second target region) selected from the group consisting of:

SEQ ID NO: 77 cggagtacgttaagcacgcggacgattggaaat,

SEQ ID NO: 78 cggaguacguuaagcacgcggacgauuggaaau,

SEQ ID NO: 79 atttccaatcgtccgcgtgcttaacgtactccg,

SEQ ID NO: 80 auuuccaaucguccgcgugcuuaacguacuccg,

SEQ ID NO: 81 cggagtacgttaagcac,

SEQ ID NO: 82 cggaguacguuaagcac,

SEQ ID NO: 83 gtgcttaacgtactccg,

SEQ ID NO: 84 gtgcttaacgtactccg,

SEQ ID NO: 85 gagtacgttaagcacgcggacgattg,

SEQ ID NO: 86 gaguacguuaagcacgcggacgauug,

SEQ ID NO: 87 caatcgtccgcgtgcttaacgtactc,

SEQ ID NO: 88 caaucguccgcgugcuuaacguacuc,

SEQ ID NO: 89 gttaagcacgcggacgattg,

SEQ ID NO: 90 guuaagcacgcggacgauug,

SEQ ID NO: 91 caatcgtccgcgtgcttaac,
SEQ ID NO: 92 caatcgtccgcgtgcttaac,

-continued

SEQ ID NO: 93 gttaagcacgcggacgattgg,

SEQ ID NO: 94 guuaagcacgcggacgauugg,

SEQ ID NO: 95 ccaatcgtccgcgtgcttaac,
and

SEQ ID NO: 96 ccaatcgtcegcgtgcttaac.

Amplification oligonucleotides of the present invention have a target binding region that is preferably from 12, 13, 14 or 15 to 20, 25, 30, 35 or 40 bases in length. The target binding region of the amplification oligonucleotide preferably comprises, overlaps with, consists essentially of, substantially corresponds to, consists of, or is contained within the reference sequence. More preferably, the amplification oligonucleotide fully hybridizes to a target sequence substantially corresponding to, consisting of, or contained within the target region under amplification conditions. The amplification oligonucleotide optionally includes a 5' sequence which is recognized by a RNA polymerase or which enhances initiation or elongation by RNA polymerase. The T7 promoter sequence of SEQ ID NO:97: aatttaatacgactcactatagggaga is preferred, although other promoter sequences may be employed.

Amplification oligonucleotides of the present invention can be employed in sets of at least two amplification oligonucleotides, and preferably include an embodiment of each of the first and second amplification oligonucleotides described above. Generally, the set of amplification oligonucleotides will include at least one each of a sense and an antisense amplification oligonucleotide, although a plurality of the same sense amplification oligonucleotides may be used. At least one member of the set of amplification oligonucleotides preferably includes a 5' sequence which is recognized by a RNA polymerase or which enhances initiation or elongation by RNA polymerase (e.g., a T7 promoter sequence) for use in a transcription-based amplification procedure. It is not a requirement of the present invention that each of the sense and antisense amplification oligonucleotides be capable of extension in the presence of a polymerase. See, e.g., Becker et al., "Single-Primer Nucleic Acid Amplification Methods," U.S. Patent Publication No. US-2006-0046265-A1, the contents of which are hereby incorporated by reference herein.

The invention additionally contemplates compositions comprising stable nucleic acid duplexes formed between any of the above-described amplification oligonucleotides and the target nucleic acids for the amplification oligonucleotides under amplification conditions.

In a further embodiment of the present invention, a set of oligonucleotides is provided for determining the presence of *C. pneumoniae* in a test sample, where each member of the set has a target binding region that stably binds, under assay conditions, to a target sequence (or its complement) derived from 23S ribosomal nucleic acid of *C. pneumoniae* and selected from the group consisting of:

SEQ ID NO: 98
cggagtacgttaagcacgcggacgattggaaatgtccgtatcacaatgag actggttagtaggcaaatccgctaacacaaggtcgggttgtggttaaggg aaatcttcggaggaactgatagtgtggcgcaaggctttc, -continued

```
SEQ ID NO: 99
cggaguacguuaagcacgcggacgauuggaaauguccguaucacaaugag

acugguuaguaggcaaauccgcuaacacaaggucggguugugguuaaggg

aaaucuucggaggaacugauaguguggcgcaaggcuuuc,

SEQ ID NO: 100
gcctcatgcaattcgtgcgcctgctaacctttacaggcatagtgttactc

tgaccaatcatccgtttaggcgattgtgttccagcccaacaccaattccc

tttagaagcctccttgactatcacaccgcgttccgaaag,
and

SEQ ID NO: 101
gccucaugcaauucgugcgccugcuaaccuuuacaggcauaguguuacuc

ugaccaaucauccguuuaggcgauuguguuccagcccaacaccaauuccc

uuuagaagccuccuugacuaucacaccgcguuccgaaag.
```

In one preferred embodiment, the set of oligonucleotides includes a detection probe, preferably one of the above-described detection probes, which preferentially hybridizes to the target sequence, or its complement, and not to nucleic acid derived from non-*C. pneumoniae* organisms present in a test sample under stringent hybridization conditions. In another preferred embodiment, the set of oligonucleotides includes a detection probe which preferentially hybridizes to the target sequence, or its complement, and not to nucleic acid derived from non-*C. pneumoniae* organisms present in a test sample under stringent hybridization conditions, and a pair of amplification oligonucleotides capable of amplifying all or a portion of the target sequence under amplification conditions. In a more preferred embodiment, the detection probe is one of the above-described detection probes and the pair of amplification oligonucleotides include at least one, and preferably a pair, of the above-described amplification oligonucleotides. In a particularly preferred embodiment, each member of the set of oligonucleotides contains a target binding region which stably and fully hybridizes, under assay conditions, to a sequence contained within the target sequence, or its complement, and at least one member of the set preferentially hybridizes to the target sequence, or its complement, and not to nucleic acid derived from non-*C. pneumoniae* organisms present in a test sample under stringent hybridization conditions.

The present invention further features methods for determining whether *C. pneumoniae* is present in a test sample. In certain embodiments, the invention provides methods for determining whether *C. pneumoniae* is present in a test sample, where such methods comprise the steps of: (a) contacting the test sample with one of the above-described detection probes for detecting *C. pneumoniae* under conditions permitting the probe to preferentially hybridize to a target nucleic acid derived from *C. pneumoniae*, thereby forming a probe:target hybrid stable for detection; and (b) determining whether the hybrid is present in the test sample as an indication of the presence or absence of *C. pneumoniae* in the test sample. This method may further include the step of quantifying the amount of hybrid present in the test sample as a means for estimating the amount of *C. pneumoniae* present in the test sample.

The methods for determining whether *C. pneumoniae* is present in a test sample, or the amount of *C. pneumoniae* present in a test sample, may further include the step of contacting the test sample with a helper oligonucleotide for facilitating hybridization of the detection probe to a target sequence and/or one of the above-described capture probes for isolating and purifying a target nucleic acid and/or one of the above-described amplification oligonucleotides appropriate for amplifying a target region present in nucleic acid derived from *C. pneumoniae*, as desired.

The invention also contemplates methods for amplifying a target sequence contained in nucleic acid derived from *C. pneumoniae* present in a test sample, where the method comprises the steps of: (a) contacting the test sample with at least one of the above-described amplification oligonucleotides; and (b) exposing the test sample to conditions sufficient to amplify the target sequence. Preferred amplification methods will include a set of at least two of the above-described amplification oligonucleotides.

In preferred embodiments, the methods for amplifying a target nucleic acid sequence present in nucleic acid derived from *C. pneumoniae* will further include the steps of: (a) contacting the test sample with a detection probe which preferentially hybridizes to the target sequence or its complement under stringent hybridization conditions, thereby forming a probe:target hybrid stable for detection; and (b) determining whether the probe:target hybrid is present in the test sample as an indication of the presence or absence of *C. pneumoniae* in the test sample. The detection probe may be contacted with the test sample prior to, at the same time as, or after the amplification oligonucleotide(s) are contacted with the test sample. The above-described detection probes are preferred for these methods.

The invention also contemplates kits for determining whether *C. pneumoniae* is present in a test sample. These kits include at least one of the above-described detection probes specific for a target sequence derived from *C. pneumoniae* and optionally include written instructions for determining the presence or amount of *C. pneumoniae* in a test sample. In another embodiment, the kits further include a helper oligonucleotide for aiding hybridization of the detection probe to the target sequence. In a further embodiment, the kits also include at least one of the above-described amplification oligonucleotides appropriate for amplifying the target sequence or its complement. In yet another embodiment, the kits further include the above-described capture probe for separating the target sequence from other components of the test sample prior to amplifying or directly detecting the target sequence or its complement. In still another embodiment, the kits additionally include at least two members of a group made up of at least one of the above-described detection probes, at least one of the above-described amplification oligonucleotides, at least one of the above-described capture probes, and a helper oligonucleotide.

The invention also contemplates kits for amplifying a target sequence present in a target nucleic acid derived from *C. pneumoniae* which include at least one of the above-described amplification oligonucleotides and optionally include written instructions for amplifying nucleic acid derived from *C. pneumoniae*. In another embodiment, the amplification kits further include at least one of the above-described capture probes for separating the target nucleic acid from other components of the test sample prior to amplifying the target sequence.

Those skilled in the art will appreciate that the detection probes of the present invention may be used as amplification oligonucleotides, helper oligonucleotides or capture probes, and the amplification oligonucleotides of the present invention may be used as helper oligonucleotides or capture probes, depending upon the degree of specificity required.

Other features and advantages of the invention will be apparent from the following description of the preferred embodiments thereof and from the claims.

DESCRIPTION OF THE PREFERRED EMBODIMENTS

The present invention features oligonucleotides targeted to nucleic acids derived from 23S ribosomal nucleic acid of *C. pneumoniae* which are particularly useful for determining the presence or absence of *C. pneumoniae* in a test sample. The oligonucleotides can aid in detecting *C. pneumoniae* in different ways, such as by functioning as detection probes, capture probes and/or amplification oligonucleotides. Detection probes of the present invention can preferentially hybridize to a target nucleic acid sequence present in a target nucleic acid derived from *C. pneumoniae* under stringent hybridization conditions to form detectable duplexes which indicate the presence of *C. pneumoniae* in a test sample. Probes of the present invention are believed to be capable of distinguishing between *C. pneumoniae* and its closest phylogenetic neighbors (*C. trachomatis* and *C. psittaci*). Capture probes of the present invention can hybridize to a target nucleic acid sequence present in nucleic acid derived from *C. pneumoniae* under assay conditions and can be used to separate target nucleic acid from other components of a clinical specimen. Amplification oligonucleotides of the present invention can hybridize to a target nucleic acid sequence present in nucleic acid derived from *C. pneumoniae* under amplification conditions and can be used, for example, as primers in amplification reactions to generate multiple copies of *C. pneumoniae*-derived nucleic acid. The probes and amplification oligonucleotides can be used in assays for the detection and/or quantitation of *C. pneumoniae* in a test sample.

A. Definitions

The following terms have the indicated meanings in the specification unless expressly indicated to have a different meaning.

By "sample" or "test sample" is meant any substance suspected of containing a target organism or nucleic acid derived from the target organism. The substance may be, for example, an unprocessed clinical specimen, such as a respiratory specimen, a buffered medium containing the specimen, a medium containing the specimen and lytic agents for releasing nucleic acid belonging to the target organism, or a medium containing nucleic acid derived from the target organism which has been isolated and/or purified in a reaction receptacle or on a reaction material or device. In the claims, the terms "sample" and "test sample" may refer to specimen in its raw form or to any stage of processing to release, isolate and purify nucleic acid derived from target organisms in the specimen. Thus, within a method of use claim, each reference to a "sample" or "test sample" may refer to a substance suspected of containing nucleic acid derived from the target organism or organisms at different stages of processing and is not limited to the initial form of the substance in the claim.

By "target nucleic acid" or "target" is meant a nucleic acid containing a target nucleic acid sequence.

By "target nucleic acid sequence," "target sequence" or "target region" is meant a specific deoxyribonucleotide or ribonucleotide sequence comprising all or part of the nucleotide sequence of a single-stranded nucleic acid molecule.

By "oligonucleotide" or "oligomer" is meant a polymer made up of two or more nucleoside subunits or nucleobase subunits coupled together. The oligonucleotide may be DNA and/or RNA and analogs thereof. The sugar groups of the nucleoside subunits may be ribose, deoxyribose and analogs thereof, including, for example, 2'-O-methyl ribose and 2' halide substitutions (e.g., 2'-F). (Oligonucleotides including nucleoside subunits having 2' substitutions and which are useful as detection probes, capture probes and/or amplification oligonucleotides are disclosed by Becker et al, "Method for Amplifying Target Nucleic Acids Using Modified Primers," U.S. Pat. No. 6,130,038.) The nucleoside subunits may be joined by linkages such as phosphodiester linkages, modified linkages, or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo-peptide backbone, such as a 2-aminoethylglycine backbone which couples the nucleobase subunits by means of a carboxymethyl linker to the central secondary amine. (DNA analogs having a pseudo-peptide backbone are referred to as "peptide nucleic acids" or "PNA", and are disclosed by Nielsen et al., "Peptide Nucleic Acids," U.S. Pat. No. 5,539,082.) The nitrogenous bases may be conventional bases (A, G, C, T, U), known analogs thereof (e.g., inosine or "I" (see Roger L. P. Adams et al., The Biochemistry of the Nucleic Acids ($11^{th}$ ed. 1992)), known derivatives of purine or pyrimidine bases (e.g., $N^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, 06 methylguanine, 4-thio-pyrimidines, 4-amino-pyrimidines, 4-dimethylhydrazine-pyrimidines, and $O^4$-alkyl-pyrimidines (see Cook et al., U.S. Pat. No. 5,623,065) and "abasic" residues where the backbone includes no nitrogenous base for one or more residues of the polymer (see Arnold et al., U.S. Pat. No. 5,585,481). Any nucleic acid analog is contemplated by the present invention, provided that the modified oligonucleotide can hybridize to a target nucleic acid under stringent hybridization conditions, amplification conditions or assay conditions, as defined herein. In the case of detection probes, the modified oligonucleotides must also be capable of preferentially hybridizing to the target nucleic acid under stringent hybridization conditions.

Oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of wild-type chromosomal DNA or the in vivo transcription products thereof. One use of an oligonucleotide is as a detection probe. Oligonucleotides may also be used as capture probes and amplification oligonucleotides.

By "detection probe" or "probe" is meant a structure comprising an oligonucleotide having a base sequence sufficiently complementary to its target nucleic acid sequence to form a probe:target hybrid stable for detection under stringent hybridization conditions. As would be understood by someone having ordinary skill in the art, the oligonucleotide is an isolated nucleic acid molecule, or an analog thereof, in a form not found in nature without human intervention (e.g., recombined with foreign nucleic acid, isolated, or purified to some extent). The probes of this invention may have additional nucleosides or nucleobases complementary to nucleotides outside of the targeted region so long as such nucleosides or nucleobases do not prevent hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promotor sequence, a binding site for RNA transcription, a restriction endonuclease recognition site, or sequences which will confer a desired secondary or tertiary structure, such as a catalytic active site or a hairpin structure, which can be used to facilitate detection and/or amplification. Probes of a defined sequence may be produced by techniques known to those of ordinary skill in the art, such as by chemical synthesis, and by in vitro or in vivo expression from recombinant nucleic acid molecules.

By "stable" or "stable for detection" is meant that the temperature of a reaction mixture is at least 2° C. below the melting temperature of a nucleic acid duplex. The temperature of the reaction mixture is more preferably at least 5° C. below the melting temperature of the nucleic acid duplex, and even more preferably at least 10° C. below the melting temperature of the reaction mixture.

By "substantially corresponding," or "substantially corresponds" is meant that the subject oligonucleotide has a base sequence containing an at least 10 contiguous base region that is at least 80% homologous, preferably at least 90% homologous, and most preferably 100% homologous to an at least 10 contiguous base region present in a reference base sequence (excluding RNA and DNA equivalents). (Those skilled in the art will readily appreciate modifications that could be made to the hybridization assay conditions at various percentages of homology to permit hybridization of the oligonucleotide to the target sequence while preventing unacceptable levels of non-specific hybridization.) The degree of similarity is determined by comparing the order of nucleobases making up the two sequences and does not take into consideration other structural differences that may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0 to 2 base differences.

By "substantially complementary" is meant that the subject oligonucleotide has a base sequence containing an at least 10 contiguous base region that is at least 80% complementary, preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0 to 2 base mismatches.

By "RNA and DNA equivalents" is meant RNA and DNA molecules having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "hybridization" or "hybridize" is meant the ability of two completely or partially complementary nucleic acid strands to come together under specified hybridization assay conditions in a parallel or preferably antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., Roger L. P. Adams et al., the Biochemistry of the Nucleic Acids ($11^{th}$ ed. 1992).)

By "preferentially hybridize" is meant that under stringent hybridization conditions, detection probes can hybridize to their target nucleic acids to form stable probe:target hybrids indicating the presence of at least one organism of interest, and there is not formed a sufficient number of stable probe: non-target hybrids to indicate the presence of non-targeted organisms, especially phylogenetically closely related organisms. Thus, the probe hybridizes to target nucleic acid to a sufficiently greater extent than to non-target nucleic acid to enable one having ordinary skill in the art to accurately detect the presence (or absence) of nucleic acid derived from *C. pneumoniae*, as appropriate, and distinguish its presence from that of a phylogenetically closely related organism in a test sample. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. Preferably, there is at least a 10-fold difference between target and non-target hybridization signals in a test sample, more preferably at least a 100-fold difference, and most preferably at least a 1.000-fold difference. Preferably, non-target hybridization signals in a test sample are no more than the background signal level.

By "stringent hybridization conditions," or "stringent conditions" is meant conditions permitting a detection probe to preferentially hybridize to a target nucleic acid (preferably rRNA or rDNA derived from *C. pneumoniae*) and not to nucleic acid derived from a closely related non-target microorganism. Stringent hybridization conditions may vary depending upon factors including the GC content and length of the probe, the degree of similarity between the probe sequence and sequences of non-target sequences which may be present in the test sample, and the target sequence. Hybridization conditions include the temperature and the composition of the hybridization reagents or solutions. Preferred hybridization assay conditions for detecting target nucleic acids derived from *C. pneumoniae* with the probes of the present invention correspond to a temperature of about 60° C.

when the salt concentration is in the range of about 0.6-0.9 M. Specific hybridization assay conditions are set forth infra in the Examples section and in the section entitled "Detection Probes to *Chlamydophila pneumoniae* Ribosomal Nucleic Acid." Other acceptable stringent hybridization conditions could be easily ascertained by those having ordinary skill in the art.

By "assay conditions" is meant conditions permitting stable hybridization of an oligonucleotide to a target nucleic acid. Assay conditions do not require preferential hybridization of the oligonucleotide to the target nucleic acid.

By "consists essentially of" or "consisting essentially of," when used with reference to an oligonucleotide herein, is meant that the oligonucleotide has a base sequence substantially homologous to a specified base sequence and may have up to four additional bases and/or two bases deleted therefrom. Thus, these phrases contain both a sequence length limitation and a sequence variation limitation. Any additions or deletions are non-material variations of the specified base sequence which do not prevent the oligonucleotide from having its claimed property, such as being able to preferentially hybridize under stringent hybridization conditions to its target nucleic acid over non-target nucleic acids. The oligonucleotide may contain a base sequence substantially similar to a specified nucleic acid sequence without any additions or deletions. However, a probe or primer containing an oligonucleotide consisting essentially of (or which consists essentially of) a specified base sequence may include other nucleic acid molecules which do not participate in hybridization of the probe to the target nucleic acid and which do not affect such hybridization.

By "nucleic acid duplex," "duplex," "nucleic acid hybrid" or "hybrid" is meant a stable nucleic acid structure comprising a double-stranded, hydrogen-bonded region. Such hybrids include RNA:RNA, RNA:DNA and DNA:DNA duplex molecules and analogs thereof. The structure is sufficiently stable to be detectable by any known means, including means that do not require a probe associated label. For instance, the detection method may include a probe-coated substrate that is optically active and sensitive to changes in mass at its surface. Mass changes result in different reflective and transmissive properties of the optically active substrate in response to light and serve to indicate the presence or amount of immobilized target nucleic acid. (This exemplary form of optical detection is disclosed by Nygren et al., "Devices and Methods for Optical Detection of Nucleic Acid Hybridization," U.S. Pat. No. 6,060,237.) Other means for detecting the formation of a nucleic acid duplex that do not require the use of a labeled probe include the use of binding agents, which include intercalating agents such as ethidium bromide. See, e.g., Higuchi, "Homogenous Methods for Nucleic Amplification and Detection," U.S. Pat. No. 5,994,056.

By "amplification oligonucleotide" or "primer" is meant an oligonucleotide capable of hybridizing to a target nucleic acid and acting as a primer and/or a promoter template (e.g., for synthesis of a complementary strand, thereby forming a functional promoter sequence) for the initiation of nucleic acid synthesis. If the amplification oligonucleotide is designed to initiate RNA synthesis, the primer may contain a base sequence which is non-complementary to the target sequence but which is recognized by a RNA polymerase such as a T7, T3, or SP6 RNA polymerase. An amplification oligonucleotide may contain a 3' terminus that is modified to prevent or lessen the rate or amount of primer extension. (See, e.g., McDonough et al, "Methods of Amplifying Nucleic Acids Using Promoter-Containing Primer Sequences," U.S. Pat. No. 5,766,849, disclose primers and promoter-primers having modified or blocked 3'-ends.) While the amplification oligonucleotides of the present invention may be chemically synthesized or derived from a vector, they are not naturally occurring nucleic acid molecules.

By "nucleic acid amplification" or "target amplification" is meant increasing the number of nucleic acid molecules having at least one target nucleic acid sequence. Target amplification according to the present invention may be either linear or exponential, although exponential amplification is preferred.

By "amplification conditions" is meant conditions permitting nucleic acid amplification. Acceptable amplification conditions could be readily ascertained without the exercise of anything more than routine experimentation by someone having ordinary skill in the art depending on the particular method of amplification employed.

By "antisense," "opposite sense," or "negative sense" is meant a nucleic acid molecule perfectly complementary to a reference, or sense, nucleic acid molecule.

By "sense," "same-sense," or "positive sense" is meant a nucleic acid molecule perfectly homologous to a reference nucleic acid molecule.

By "amplicon" or "amplification product" is meant a nucleic acid molecule generated in a nucleic acid amplification reaction and which is derived from a target nucleic acid. An amplicon or amplification product contains a target nucleic acid sequence that may be of the same or opposite sense as the target nucleic acid.

By "derived" is meant that the referred to nucleic acid is obtained directly from an organism or is the product of a nucleic acid amplification. Thus, a nucleic acid that is "derived" from an organism may be, for example, an antisense RNA molecule which does not naturally exist in the organism.

By "capture probe" is meant an oligonucleotide that is capable of binding to a target nucleic acid (preferably in a region other than that targeted by a detection probe) and, either directly or indirectly, to a solid support, thereby providing means for immobilizing and isolating the target nucleic acid in a test sample. The capture probe includes a target binding region that hybridizes to the target nucleic acid. Although the capture probe may include a member of ligand-ligate binding pair (e.g., avidin-biotin linkage) for immobilizing the capture probe on a solid support, preferred capture probes include an immobilized probe binding region that hybridizes to an immobilized probe bound to a solid support. While the capture probe preferably hybridizes to both the target nucleic acid and the immobilized probe under stringent conditions, the target binding and the immobilized probe binding regions of the capture probe may be designed to bind to their target sequences under different hybridization conditions. In this way, the capture probe may be designed so that it first hybridizes to the target nucleic acid under more favorable in solution kinetics before adjusting the conditions to permit hybridization of the immobilized probe binding region to the immobilized probe.

The target binding and immobilized probe binding regions may be contained within the same oligonucleotide, directly adjoining each other or separated by one or more optionally modified nucleotides, or these regions may be joined to each other by means of a non-nucleotide linker.

By "target binding region" is meant that portion of an oligonucleotide which stably binds to a target sequence present in a target nucleic acid, a DNA or RNA equivalent of the target sequence or a complement of the target sequence under assay conditions. The assay conditions may be stringent hybridization conditions or amplification conditions.

By "immobilized probe binding region" is meant that portion of an oligonucleotide which hybridizes to an immobilized probe under assay conditions.

By "homopolymer tail" in the claims is meant a contiguous base sequence of at least 10 identical bases (e.g., 10 contiguous adenines or thymines).

By "immobilized probe" is meant an oligonucleotide for joining a capture probe to an immobilized support. The immobilized probe is joined either directly or indirectly to the solid support by a linkage or interaction which remains stable under the conditions employed to hybridize the capture probe to the target nucleic acid and to the immobilized probe, whether those conditions are the same or different. The immobilized probe facilitates separation of the bound target nucleic acid from unbound materials in a sample.

By "isolate" or "isolating" is meant that at least a portion of the target nucleic acid present in a test sample is concentrated within a reaction receptacle or on a reaction device or solid carrier (e.g., test tube, cuvette, microtiter plate well, nitrocellulose filter, slide or pipette tip) in a fixed or releasable manner so that the target nucleic acid can be purified without significant loss of the target nucleic acid from the receptacle, device or carrier.

By "purify" or "purifying" is meant that one or more components of the test sample are removed from one or more other components of the sample. Sample components to be purified may include viruses, nucleic acids or, in particular, target nucleic acids in a generally aqueous solution phase which may also include undesirable materials such as proteins, carbohydrates, lipids, non-target nucleic acid and/or labeled probes. Preferably, the purifying step removes at least about 70%, more preferably at least about 90% and, even more preferably, at least about 95% of the undesirable components present in the sample.

By "phylogenetically closely related" is meant that the organisms are closely related to each other in an evolutionary sense and therefore would be expected to have a higher total nucleic acid sequence homology than organisms that are more distantly related. Organisms occupying adjacent and next to adjacent positions on the phylogenetic tree are closely related. Organisms occupying positions farther away than adjacent or next to adjacent positions on the phylogenetic tree will still be closely related if they have significant total nucleic acid sequence homology.

B. Hybridization Conditions and Probe Design

Hybridization reaction conditions, most importantly the temperature of hybridization and the concentration of salt in the hybridization solution, can be selected to allow the detection probes or, in some cases, amplification oligonucleotides of the present invention to preferentially hybridize to a *C. pneumoniae*-derived target nucleic acid and not to other non-target nucleic acids suspected of being present in a test sample. At decreased salt concentrations and/or increased temperatures (conditions of increased stringency) the extent of nucleic acid hybridization decreases as hydrogen bonding between paired nucleobases in the double-stranded hybrid molecule is disrupted. This process is known as "melting."

Generally speaking, the most stable hybrids are those having the largest number of contiguous, perfectly matched (i.e., hydrogen-bonded) nucleotide base pairs. Such hybrids would usually be expected to be the last to melt as the stringency of the hybridization conditions increases. However, a double-stranded nucleic acid region containing one or more mismatched, "non-canonical," or imperfect base pairs (resulting in weaker or non-existent base pairing at that position in the nucleotide sequence of a nucleic acid) may still be sufficiently stable under conditions of relatively high stringency to allow the nucleic acid hybrid to be formed and detected in a hybridization assay without cross-reacting with other, non-selected nucleic acids which may be present in a test sample.

Hence, depending on the degree of similarity between the nucleotide sequences of the target nucleic acid and those of non-target nucleic acids belonging to phylogenetically distinct, but closely-related organisms on one hand, and the degree of complementarity between the nucleotide sequences of a particular detection probe or amplification oligonucleotide and those of the target and non-target nucleic acids on the other, one or more mismatches will not necessarily defeat the ability of an oligonucleotide contained in the probe or amplification oligonucleotide to hybridize to the target nucleic acid and not to non-target nucleic acids.

The detection probes of the present invention were chosen, selected, and/or designed to maximize the difference between the melting temperatures of the probe:target hybrid ($T_m$, defined as the temperature at which half of the potentially double-stranded molecules in a given reaction mixture are in a single-stranded, denatured state) and the $T_m$ of a mismatched hybrid formed between the probe and ribosomal RNA (rRNA) or ribosomal DNA (rDNA) of the phylogenetically most closely-related organisms expected to be present in the test sample, but not sought to be detected. While the unlabeled amplification oligonucleotides and capture probes need not have such an extremely high degree of specificity as the detection probe to be useful in the present invention, they are designed in a similar manner to preferentially hybridize to one or more target nucleic acids over other nucleic acids under specified amplification, assay or stringent hybridization conditions.

Within the rRNA molecule there is a close relationship between secondary structure (caused in part by intra-molecular hydrogen bonding) and function. This fact imposes restrictions on evolutionary changes in the primary nucleotide sequence causing the secondary structure to be maintained. For example, if a base is changed in one "strand" of a double helix (due to intra-molecular hydrogen bonding, both "strands" are part of the same rRNA molecule), a compensating substitution usually occurs in the primary sequence of the other "strand" in order to preserve complementarity (this is referred to as co-variance), and thus the necessary secondary structure. This allows two very different rRNA sequences to be aligned based both on the conserved primary sequence and also on the conserved secondary structure elements. Potential target sequences for the detection probes described herein were identified by noting variations in the homology of the aligned sequences.

The sequence evolution at each of the variable regions is mostly divergent. Because of the divergence, corresponding rRNA variable regions of more distant phylogenetic relatives of *C. pneumoniae* show greater differences from *C. pneumoniae* rRNA than do the rRNAs of phylogenetically closer relatives. Sufficient variation between *C. pneumoniae* and other organisms was observed to identify preferred target sites and to design detection probes useful for distinguishing *C. pneumoniae* over non-*C. pneumoniae* organisms in a test sample, particularly *C. psittaci*, the most closely related organism to *C. pneumoniae*.

Merely identifying putatively unique potential target nucleotide sequences does not guarantee that a functionally species-specific detection probe may be made to hybridize to *C. pneumoniae* rRNA or rDNA comprising that sequence. Various other factors will determine the suitability of a nucleic acid locus as a target site for genus-specific or species-specific probes. Because the extent and specificity of hybridization reactions such as those described herein are affected by a number of factors, manipulation of one or more of those factors will determine the exact sensitivity and specificity of a particular oligonucleotide, whether perfectly complementary to its target or not. The importance and effect of various assay conditions are known to those skilled in the art and are disclosed by Hogan et al., "Nucleic Acid Probes for Detection and/or Quantitation of Non-Viral Organisms," U.S. Pat. No. 5,840,488; Hogan et al., "Nucleic Acid Probes to *Mycobacterium gordonae*," U.S. Pat. No. 5,216,143; and Kohne, "Method for Detection, Identification and Quantitation of Non-Viral Organisms," U.S. Pat. No. 4,851,330. The contents of each of the foregoing references is hereby incorporated by reference herein.

The desired temperature of hybridization and the hybridization solution composition (such as salt concentration, detergents, and other solutes) can also greatly affect the stability of double-stranded hybrids. Conditions such as ionic strength and the temperature at which a probe will be allowed to hybridize to a target must be taken into account in constructing a genus-specific or species-specific probe. The thermal stability of hybrid nucleic acids generally increases with the ionic strength of the reaction mixture. On the other hand, chemical reagents that disrupt hydrogen bonds, such as formamide, urea, dimethyl sulfoxide and alcohols, can greatly reduce the thermal stability of the hybrids.

To maximize the specificity of a probe for its target, the subject probes of the present invention were designed to hybridize to their targets under conditions of high stringency. Under such conditions only single nucleic acid strands having a high degree of complementarity will hybridize to each other. Single nucleic acid strands without such a high degree of complementarity will not form hybrids. Accordingly, the stringency of the assay conditions determines the amount of complementarity that should exist between two nucleic acid strands in order to form a hybrid. Stringency is chosen to maximize the difference in stability between the hybrid formed between the probe and the target nucleic acid and potential hybrids between the probe and any non-target nucleic acids present in a test sample.

Proper specificity may be achieved by minimizing the length of the detection probe having perfect complementarity to sequences of non-target organisms, by avoiding G and C rich regions of complementarity to non-target nucleic acids, and by constructing the probe to contain as many destabilizing mismatches to non-target sequences as possible. Whether a probe is appropriate for detecting only a specific type of organism depends largely on the thermal stability difference between probe:target hybrids versus probe:non-target hybrids. In designing probes, the differences in these $T_m$ values should be as large as possible (preferably 2-5° C. or more). Manipulation of the $T_m$ can be accomplished by changes to probe length and probe composition (e.g., GC content versus AT content).

In general, the optimal hybridization temperature for oligonucleotide probes is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G-C base pairs exhibit additional hydrogen bonding and therefore greater thermal stability than A-T base pairs. Such considerations are known in the art. (See, e.g., J. Sambrook et al., Molecular Cloning: A Laboratory Manual, ch. 11 ($2^{nd}$ ed. 1989).)

A preferred method to determine $T_m$ measures hybridization using the well known Hybridization Protection Assay (HPA) disclosed by Arnold et al., "Homogenous Protection Assay," U.S. Pat. No. 5,283,174, the contents of which are hereby incorporated by reference herein. The $T_m$ can be measured using HPA in the following manner. Probe molecules are labeled with an acridinium ester and permitted to form probe:target hybrids in a lithium succinate buffer (0.1 M lithium succinate buffer, pH 4.7, 20 mM EDTA, 15 mM aldrithiol-2, 1.2 M LiCl, 3% (v/v) ethanol absolute, 2% (w/v) lithium lauryl sulfate) using an excess amount of target. Aliquots of the solution containing the probe:target hybrids are then diluted in the lithium succinate buffered solution and incubated for five minutes at various temperatures starting below that of the anticipated $T_m$ (typically 55° C.) and increasing in 2-5° C. increments. This solution is then diluted with a mild alkaline borate buffer (600 mM boric acid, 240 mM NaOH, 1% (v/v) TRITON® X-100 detergent, pH 8.5) and incubated at an equal or lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer, such as a LEADER® HC+ Luminometer (Gen-Probe Incorporated; San Diego, Calif.; Cat. No. 4747). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods known to those skilled in the art (see, e.g., Hogan et al., U.S. Pat. No. 5,840,488).

To ensure specificity of a detection probe for its target, it is preferable to design probes that hybridize only to target nucleic acid under conditions of high stringency. Only highly complementary sequences will form hybrids under conditions of high stringency. Accordingly, the stringency of the assay conditions determines the amount of complementarity needed between two sequences in order for a stable hybrid to form. Stringency should be chosen to maximize the difference in stability between the probe:target hybrid and potential probe:non-target hybrids.

Examples of specific stringent hybridization conditions are provided in the Examples section infra. Of course, alternative stringent hybridization conditions can be determined by those of ordinary skill in the art based on the present disclosure. (See, e.g., Sambrook et al., supra, ch. 11.)

The length of the target nucleic acid sequence region and, accordingly, the length of the probe sequence can also be important. In some cases, there may be several sequences from a particular region, varying in location and length, which may be used to design probes with the desired hybridization characteristics. In other cases, one probe may be significantly better with regard to specificity than another that differs from it merely by a single base. While it is possible for nucleic acids that are not perfectly complementary to hybridize, the longest stretch of perfectly complementary bases, as well as the base compositions, will generally determine hybrid stability.

Regions of rRNA known to form strong internal structures inhibitory to hybridization are less preferred target regions. Likewise, probes with extensive self-complementarity are generally to be avoided, with specific exceptions being discussed below. If a strand is wholly or partially involved in an intramolecular or intermolecular hybrid, it will be less able to participate in the formation of a new intermolecular probe: target hybrid without a change in the reaction conditions. Ribosomal RNA molecules are known to form very stable intramolecular helices and secondary structures by hydrogen bonding. By designing a probe to a region of the target nucleic acid which remains substantially single-stranded under hybridization conditions, the rate and extent of hybridization between probe and target may be increased.

A genomic ribosomal nucleic acid (rDNA) target occurs naturally in a double-stranded form, as does the product of the polymerase chain reaction (PCR). These double-stranded targets are naturally inhibitory to hybridization with a probe and require denaturation prior to hybridization. Appropriate denaturation and hybridization conditions are known in the art (see, e.g., Southern, E. M., *J. Mol. Biol.,* 98:503 (1975)).

A number of formulae are available which will provide an estimate of the melting temperature for perfectly matched oligonucleotides to their target nucleic acids. One such formula is the following: $T_m$=81.5+16.6($\log_{10}$[Na+])+0.41 (fraction G+C)−(600/N) (where N=the length of the oligonucleotide in number of nucleotides) provides a good estimate of the $T_m$ for oligonucleotides between 14 and 60 to 70 nucleotides in length. From such calculations, subsequent empirical verification or "fine tuning" of the $T_m$ may be made using screening techniques well known in the art. For further information on hybridization and oligonucleotide probes reference may be made to SAMBROOK ET AL., supra, ch. 11. This reference, among others well known in the art, also provides estimates of the effect of mismatches on the $T_m$ of a hybrid. Thus, from the known nucleotide sequence of a given region of the ribosomal RNA (or rDNA) of two or more organisms, oligonucleotides may be designed which will distinguish these organisms from one another.

C. Nucleic Acid Amplification

Preferably, the amplification oligonucleotides of the present invention are oligodeoxynucleotides and are sufficiently long to be used as a substrate for the synthesis of extension products by a nucleic acid polymerase. Optimal amplification oligonucleotide length should take into account several factors, including the temperature of reaction, the structure and base composition of the amplification oligonucleotide, and how the amplification oligonucleotide is to be used. For example, for optimal specificity the oligonucleotide amplification oligonucleotide generally should be at least 12 bases in length, depending on the complexity of the target nucleic acid sequence. If such specificity is not essential, shorter amplification oligonucleotides may be used. In such a case, it may be desirable to carry out the reaction at cooler temperatures in order to form stable hybrid complexes with the template nucleic acid.

Useful guidelines for designing amplification oligonucleotides and detection probes with desired characteristics are described infra in the section entitled "Preparation of Oligonucleotides." Optimal sites for amplifying and probing contain at least two, and preferably three, conserved regions of *C. pneumoniae* nucleic acid. These regions are about 15 to 350 bases in length, and preferably between about 15 and 150 bases in length.

The degree of amplification observed with a set of amplification oligonucleotides (e.g., primers and/or promoter-primers) depends on several factors, including the ability of the amplification oligonucleotides to hybridize to their specific target sequences and their ability to be extended or copied enzymatically. While amplification oligonucleotides of different lengths and base compositions may be used, amplification oligonucleotides preferred in this invention have target binding regions of 15 to 40 bases with a predicted $T_m$ to target of about 42° C.

Parameters affecting probe hybridization, such as $T_m$, complementarity, and secondary structure of the target sequence, also affect amplification oligonucleotide hybridization and therefore performance of the amplification oligonucleotides. The degree of non-specific extension (primer-dimer or non-target copying) can also affect amplification efficiency. Thus, amplification oligonucleotides are selected to have low self-complementarity or cross-complementarity, particularly at the 3' ends of their sequences. Notwithstanding, it should be noted that the "signal primers" described infra could be modified to include regions of self-complementarity, thereby transforming them into "molecular torch" or "molecular beacon" signal primers, such as these terms are defined below. Lengthy homopolymer runs and high GC content are avoided to reduce spurious primer extension. Computer programs are available to aid in this aspect of the design, including Oligo Tech analysis software which is available from Oligos Etc. Inc. and can be accessed on the World Wide Web at www.oligosetc.com/analysis.php using a hypertext transfer protocol (http) in the URL.

A nucleic acid polymerase used in conjunction with the amplification oligonucleotides of the present invention refers to a chemical, physical, or biological agent that incorporates either ribonucleotides or deoxyribonucleotides, or both, into a nucleic acid polymer, or strand, in a template-dependent manner. Examples of nucleic acid polymerases include DNA-directed DNA polymerases, RNA-directed DNA polymerases, and RNA-directed RNA polymerases. DNA polymerases bring about nucleic acid synthesis in a template-dependent manner and in a 5 to 3' direction. Because of the typical anti-parallel orientation of the two strands in a double-stranded nucleic acid, this direction is from a 3' region on the template to a 5' region on the template. Examples of DNA-directed DNA polymerases include *E. coli* DNA polymerase I, the thermostable DNA polymerase from *Thermus aquaticus* (Taq), and the large fragment of DNA polymerase I from *Bacillus stearothermophilis* (Bst). Examples of RNA directed DNA polymerases include various retroviral reverse transcriptases, such as Moloney murine leukemia virus (MMLV) reverse transcriptase or avian myeloblastosis virus (AMV) reverse transcriptase.

During most nucleic acid amplification reactions, a nucleic acid polymerase adds nucleotide residues to the 3' end of the primer using the target nucleic acid as a template, thus synthesizing a second nucleic acid strand having a nucleotide sequence partially or completely complementary to a region of the target nucleic acid. In many nucleic acid amplification reactions, the two strands comprising the resulting double-stranded structure must be separated by chemical or physical means in order to allow the amplification reaction to proceed. Alternatively, the newly synthesized template strand may be made available for hybridization with a second primer or promoter-primer by other means, such as through strand displacement or the use of a nucleolytic enzyme which digests part or all of the original target strand. In this way the process may be repeated through a number of cycles, resulting in a large increase in the number of nucleic acid molecules having the target nucleotide sequence.

Either the first or second amplification oligonucleotide, or both, may be a promoter-primer. (In some applications, the amplification oligonucleotides may only consist of promoter-primers which are complementary to the sense strand, as disclosed by Kacian et al., "Nucleic Acid Sequence Amplification Method, Composition and Kit," U.S. Pat. No. 5,554,516, the contents of which are hereby incorporated by reference herein.) A promoter-primer usually contains an oligonucleotide that is not complementary to a nucleotide sequence present in the target nucleic acid molecule or primer extension product(s) (see Kacian et al., "Nucleic Acid Sequence Amplification Methods," U.S. Pat. No. 5,399,491, the contents of which are hereby incorporated by reference herein). These non-complementary sequences may be located 5' to the complementary sequences on the amplification oligonucleotide and may provide a locus for initiation of RNA synthesis when made double-stranded through the action of a nucleic acid polymerase. The promoter thus provided may allow for the in vitro transcription of multiple RNA copies of the target nucleic acid sequence. It will be appreciated that when reference is made to a primer in this specification, such reference is intended to include the primer aspect of a promoter-primer as well, unless the context of the reference clearly indicates otherwise.

In some amplification systems (see, e.g., Dattagupta et al., "Isothermal Strand Displacement Amplification," U.S. Pat. No. 6,087,133, the contents of which are hereby incorporated by reference herein), the amplification oligonucleotides may contain 5' non-complementary nucleotides which assist in strand displacement. Furthermore, when used in conjunction with a nucleic acid polymerase having 5' exonuclease activity, the amplification oligonucleotides may have modifications at their 5' end to prevent enzymatic digestion. Alternatively, the nucleic acid polymerase may be modified to remove the 5' exonuclease activity, such as by treatment with a protease that generates an active polymerase fragment with no such nuclease activity. In such a case the primers need not be modified at their 5' ends.

1. Preparation of Oligonucleotides

The detection probes, capture probes and amplification oligonucleotides of the present invention can be readily prepared by methods known in the art. Preferably, the oligonucleotides are synthesized using solid phase methods. For example, Caruthers describes using standard phosphoramidite solid-phase chemistry to join nucleotides by phosphodiester linkages. See Caruthers et al, "Chemical Synthesis of Deoxynucleotides by the Phosphoramidite Method," *Methods Enzymol.,* 154:287 (1987). Automated solid-phase chemical synthesis using cyanoethyl phosphoramidite precursors has been described by Barone. See Barone et al., "In Situ Activation of bis-dialkylaminephosphines—a New Method for Synthesizing Deoxyoligonucleotides on Polymer Supports," *Nucleic Acids Res.,* 12(10):4051 (1984). Likewise, Bhatt, "Method and Reagent for Sulfurization of Organophosphorous Compounds," U.S. Pat. No. 5,449,769, discloses a procedure for synthesizing oligonucleotides containing phosphorothioate linkages. In addition, Riley et al, "Process for the Purification of Oligomers," U.S. Pat. No. 5,811,538, disclose the synthesis of oligonucleotides having different linkages, including methylphosphonate linkages. Moreover, methods for the organic synthesis of oligonucleotides are known to those of skill in the art and are described in, for example, SAMBROOK ET AL., supra, ch. 10. Each of the foregoing references is hereby incorporated by reference herein.

Following synthesis of a particular oligonucleotide, several different procedures may be utilized to purify and control the quality of the oligonucleotide. Suitable procedures include polyacrylamide gel electrophoresis or high pressure liquid chromatography. Both of these procedures are well known to those skilled in the art.

All of the oligonucleotides of the present invention, whether detection probes, capture probes or amplification oligonucleotides, may be modified with chemical groups to enhance their performance or to facilitate the characterization of amplification products.

For example, backbone-modified oligonucleotides such as those having phosphorothioate, methylphosphonate, 2'-O-alkyl, or peptide groups which render the oligonucleotides resistant to the nucleolytic activity of certain polymerases or to nuclease enzymes may allow the use of such enzymes in an amplification or other reaction. Another example of a modification involves using non-nucleotide linkers incorporated between nucleotides in the nucleic acid chain of a probe or primer, and which do not prevent hybridization of a probe or hybridization and elongation of a primer. (See Arnold et al., "Non-Nucleotide Linking Reagents for Nucleotide Probes," U.S. Pat. No. 6,031,091, the contents of which are hereby incorporated by reference herein.) The oligonucleotides of the present invention may also contain mixtures of the desired modified and natural nucleotides.

The 3' end of an amplification oligonucleotide, particularly a promoter-primer, may be modified or blocked to prevent or inhibit initiation of DNA synthesis, as disclosed by Kacian et al., U.S. Pat. No. 5,554,516, and Kolk et al., "Single-Primer Nucleic Acid Amplification Methods," U.S. Provisional Application No. 60/639,110, the contents of which are hereby incorporated by reference herein. The 3' end of the primer can be modified in a variety of ways well known in the art. By way of example, appropriate modifications to a promoter-primer can include the addition of ribonucleotides, 3' deoxynucleotide residues (e.g., cordycepin), 2',3'-dideoxynucleotide residues, modified nucleotides such as phosphorothioates, and non-nucleotide linkages such as those disclosed by Arnold et al. in U.S. Pat. No. 6,031,091 or alkane-diol modifications (see Wilk et al, "Backbone-Modified Oligonucleotides Containing a Butanediol-1,3 Moiety as a 'Vicarious Segment' for the Deoxyribosyl Moiety—Synthesis and Enzyme Studies," *Nucleic Acids Res.,* 18(8):2065 (1990), the contents of which are hereby incorporated by reference herein), or the modification may simply consist of a region 3' to the priming sequence that is non-complementary to the target nucleic acid sequence. Additionally, a mixture of different 3' blocked promoter-primers or of 3' blocked and unblocked promoter-primers may increase the efficiency of nucleic acid amplification, as described therein.

As disclosed above, the 5' end of primers may be modified to be resistant to the 5'-exonuclease activity present in some nucleic acid polymerases. Such modifications can be carried out by adding a non-nucleotide group to the terminal 5' nucleotide of the primer using techniques such as those disclosed by Arnold et al, U.S. Pat. No. 6,031,091.

Once synthesized, a selected oligonucleotide may be labeled by any well known method (see, e.g., SAMBROOK ET AL., supra, ch. 10). Useful labels include radioisotopes as well as non-radioactive reporting groups. Isotopic labels include $^{3}H$, $^{35}S$, $^{32}P$, $^{125}I$, $^{57}Co$, and $^{14}C$. Isotopic labels can be introduced into the oligonucleotide by techniques known in the art such as nick translation, end labeling, second strand synthesis, the use of reverse transcription, and by chemical methods. When using radiolabeled probes, hybridization can be detected by autoradiography, scintillation counting, or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as disclosed by Arnold et al., U.S. Pat. No. 6,031,091. Non-isotopic labels include fluorescent molecules (individual labels or combinations of labels, such as the fluorescence resonance energy transfer (FRET) pairs disclosed by Tyagi et al., "Detectably Labeled Dual Conformation Oligonucleotide Probes," U.S. Pat. No. 5,925,517), chemiluminescent molecules, enzymes, cofactors, enzyme substrates, haptens, or other ligands.

With the detection probes of the present invention, the probes are preferably labeled using of a non-nucleotide linker with an acridinium ester. Acridinium ester labeling may be performed as disclosed by Arnold et al., "Acridinium Ester Labelling and Purification of Nucleotide Probes," U.S. Pat. No. 5,185,439, the contents of which are hereby incorporated by reference herein.

2. Amplification of *Chlamydophila pneumoniae* Ribosomal Nucleic Acid

The amplification oligonucleotides of the present invention are directed to 23S regions of ribosomal nucleic acid derived from *C. pneumoniae*. These amplification oligonucleotides may flank, overlap, or be contained within at least one of the target sequences of a detection probe (or its complement) used to detect the presence of *C. pneumoniae* in a nucleic acid amplification assay. As indicated above, the amplification oligonucleotides may also include non-complementary bases at their 5' ends comprising a promoter sequence able to bind a RNA polymerase and direct RNA transcription using the target nucleic acid as a template. A T7 promoter sequence, such as SEQ ID NO:97, may be used.

Amplification oligonucleotides of the present invention are capable of amplifying a region of nucleic acid derived from 23S ribosomal nucleic acid of *C. pneumoniae* under amplification conditions. In one embodiment, a first amplification oligonucleotide of the present invention preferably comprises a target binding region up to 40 bases in length which stably hybridizes, under amplification conditions, to a target sequence contained within a first target region selected from the group consisting of SEQ ID NO:37, SEQ ID NO:38, SEQ ID NO:39 and SEQ ID NO:40. More preferably, the base sequence of the target binding region comprises, overlaps with, consists essentially of, substantially corresponds to, consists of, or is contained within and includes at least 12, 13, 14 or 15 of 15 contiguous bases of a base sequence selected from the group consisting of SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71 or SEQ ID NO:72. Even more preferably, the first amplification oligonucleotide fully hybridizes to a target sequence substantially corresponding to, consisting of, or contained within the first target region.

In another embodiment, a second amplification oligonucleotide of the present invention preferably comprises a target binding region up to 40 bases in length which stably hybridizes, under amplification conditions, to a target sequence contained within a second target region selected from the group consisting of SEQ ID NO:73, SEQ ID NO:74, SEQ ID NO:75 and SEQ ID NO:76. More preferably, the base sequence of the target binding region comprises, overlaps with, consists essentially of, substantially corresponds to, consists of, or is contained within and includes at least 12, 13, 14 or 15 of 15 contiguous bases of a base sequence selected from the group consisting of SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95 or SEQ ID NO:96. Even more preferably, the second amplification oligonucleotide fully hybridizes to a target sequence substantially corresponding to, consisting of, or contained within the second target region.

The amplification oligonucleotides of the present invention are preferably provided in sets of at least two amplification oligonucleotides for amplifying *C. pneumoniae*-derived nucleic acid. Each set of amplification oligonucleotides preferably has at least one antisense amplification oligonucleotide and at least one sense amplification oligonucleotide. Preferred sets of amplification oligonucleotides comprise at least one of the above-described first amplification oligonucleotides in combination with any of the above-described second amplification oligonucleotides. More preferably, the set of amplification oligonucleotides is used in a transcription-based amplification procedure and at least one of the amplification oligonucleotides includes a promoter sequence recognized by an RNA polymerase.

Amplification oligonucleotides of the present invention may have modifications, such as blocked 3' and/or 5' termini (as discussed above) or sequence additions including, but not limited to, a specific nucleotide sequence recognized by a RNA polymerase (e.g., a promoter sequence for T7, T3 or SP6 RNA polymerase), a sequence which enhances initiation or elongation of RNA transcription by a RNA polymerase, or a sequence which may provide for intra-molecular base pairing and encourage the formation of secondary or tertiary nucleic acid structures.

Amplification oligonucleotides are used in any suitable nucleic acid amplification procedure now known or later developed. Existing amplification procedures include the polymerase chain reaction (PCR), transcription-mediated amplification (TMA), nucleic acid sequence-based amplification (NASBA), self-sustained sequence replication (3SR), ligase chain reaction (LCR), strand displacement amplification (SDA), and Loop-Mediated Isothermal Amplification (LAMP), each of which is well known in the art. See, e.g., Mullis, "Process for Amplifying Nucleic Acid Sequences," U.S. Pat. No. 4,683,202; Erlich et al., "Kits for Amplifying and Detecting Nucleic Acid Sequences," U.S. Pat. No. 6,197,563; Walker et al., *Nucleic Acids Res.,* 20:1691-1696 (1992); Fahy et al., "Self-sustained Sequence Replication (3SR): An Isothermal Transcription-Based Amplification System Alternative to PCR," *PCR Methods and Applications,* 1:25-33 (1991); Kacian et al, U.S. Pat. No. 5,399,491; Kacian et al., "Nucleic Acid Sequence Amplification Methods," U.S. Pat. No. 5,480,784; Davey et al., "Nucleic Acid Amplification Process," U.S. Pat. No. 5,554,517; Birkenmeyer et al., "Amplification of Target Nucleic Acids Using Gap Filling Ligase Chain Reaction," U.S. Pat. No. 5,427,930; Marshall et al., "Amplification of RNA Sequences Using the Ligase Chain Reaction," U.S. Pat. No. 5,686,272; Walker, "Strand Displacement Amplification," U.S. Pat. No. 5,712,124; Notomi et al., "Process for Synthesizing Nucleic Acid," European Patent Application No. 1 020 534 A1; Dattagupta et al, "Isothermal Strand Displacement Amplification," U.S. Pat. No. 6,214,587; and HELEN H. LEE ET AL., NUCLEIC ACID AMPLIFICATION TECHNOLOGIES: APPLICATION TO DISEASE DIAGNOSIS (1997). (Each of the foregoing amplification references is hereby incorporated by reference herein.) Any other amplification procedure which meets the definition of "nucleic acid amplification" supra is also contemplated by the inventors.

Amplification oligonucleotides of the present invention are preferably unlabeled but may include one or more reporter groups to facilitate detection of a target nucleic acid in combination with or exclusive of a detection probe. A wide variety of methods are available to detect an amplified target sequence. For example, the nucleotide substrates or the amplification oligonucleotides can include a detectable label that is incorporated into newly synthesized DNA. The resulting labeled amplification product is then generally separated from the unused labeled nucleotides or amplification oligonucleotides and the label is detected in the separated product fraction. (See, e.g., Wu, "Detection of Amplified Nucleic Acid Using Secondary Capture Oligonucleotides and Test Kit," U.S. Pat. No. 5,387,510.)

A separation step is not required, however, if the amplification oligonucleotide is modified by, for example, linking it to an interacting label pair, such as two dyes which form a donor/acceptor dye pair. The modified amplification oligonucleotide can be designed so that the fluorescence of one dye pair member remains quenched by the other dye pair member, so long as the amplification oligonucleotide does not hybridize to target nucleic acid, thereby physically separating the two dyes. Moreover, the amplification oligonucleotide can be further modified to include a restriction endonuclease recognition site positioned between the two dyes so that when a hybrid is formed between the modified amplification oligonucleotide and target nucleic acid, the restriction endonuclease recognition site is rendered double-stranded and available for cleavage or nicking by an appropriate restriction endonuclease. Cleavage or nicking of the hybrid then separates the two dyes, resulting in a change in fluorescence due to decreased quenching which can be detected as an indication of the presence of the target organism in the test sample. This type of modified amplification oligonucleotide, referred to as a "signal primer," is disclosed by Nadeau et al., "Detection of Nucleic Acids by Fluorescence Quenching," U.S. Pat. No. 6,054,279.

Substances which can serve as useful detectable labels are well known in the art and include radioactive isotopes, fluorescent molecules, chemiluminescent molecules, chromophores, as well as ligands such as biotin and haptens which, while not directly detectable, can be readily detected by a reaction with labeled forms of their specific binding partners, e.g., avidin and antibodies, respectively.

Another approach is to detect the amplification product by hybridization with a detectably labeled oligonucleotide probe and measuring the resulting hybrids in any conventional manner. In particular, the product can be assayed by hybridizing a chemiluminescent acridinium ester-labeled oligonucleotide probe to the target sequence, selectively hydrolyzing the acridinium ester present on unhybridized probe, and measuring the chemiluminescence produced from the remaining acridinium ester in a luminometer. (See, e.g., Arnold et al., U.S. Pat. No. 5,283,174, and NORMAN C. NELSON ET AL., NONISOTOPIC PROBING, BLOTTING, AND SEQUENCING, ch. 17 (Larry J. Kricka ed., 2d ed. 1995).)

D. Sample Processing

Sample processing prior to amplification or detection of a target sequence may be necessary or useful for discriminating a target sequence from non-target nucleic acid present in a sample. Sample processing procedures may include, for example, direct or indirect immobilization of nucleic acids and/or oligonucleotides from the liquid phase in a heterogeneous assay. With some procedures, such immobilization may require multiple hybridization events. Ranki et al., "Detection of Microbial Nucleic Acids by a One-Step Sandwich Hybridization Test," U.S. Pat. Nos. 4,486,539 and 4,563,419, for example, disclose a one-step nucleic acid "sandwich" hybridization method involving the use of a solid-phase bound nucleic acid having a target complementary sequence and a labeled nucleic acid probe which is complementary to a distinct region of the target nucleic acid. Stabinsky, "Methods and Kits for Performing Nucleic Acid Hybridization Assays," U.S. Pat. No. 4,751,177, discloses methods including a "mediator" polynucleotide that reportedly overcomes sensitivity problems associated with Ranki's method resulting from leakage of immobilized probe from the solid support. Instead of directly immobilizing the target nucleic acid, the mediator polynucleotides of Stabinsky are used to bind and indirectly immobilize target polynucleotide: probe polynucleotide complexes which have formed free in solution.

Any known solid support may be used for sample processing, such as matrices and particles free in solution. The solid support may be, for example, nitrocellulose, nylon, glass, polyacrylate, mixed polymers, polystyrene, silane polypropylene and, preferably, particles having a magnetic charge to facilitate recovering sample and/or removing unbound nucleic acids or other sample components. Particularly preferred supports are magnetic spheres that are monodisperse (i.e., uniform in size±5%), thereby providing consistent results, which is particularly advantageous for use in an automated procedure. One such automated procedure is disclosed by Ammann et al., "Automated Process for Isolating and Amplifying a Target Nucleic Acid Sequence," U.S. Pat. No. 6,335,166, the contents of which are hereby incorporated by reference herein.

An oligonucleotide for immobilizing a target nucleic acid on a solid support may be joined directly or indirectly to the solid support by any linkage or interaction which is stable under assay conditions (e.g., conditions for amplification and/or detection). Referred to herein as an "immobilized probe," this oligonucleotide may bind directly to the target nucleic acid or it may include a base sequence region, such as a homopolymeric tract (e.g., a poly dT) or a simple short repeating sequence (e.g., an AT repeat), which hybridizes to a complementary base sequence region present on a capture probe. Direct joining occurs when the immobilized probe is joined to the solid support in the absence of an intermediate group. For example, direct joining may be via a covalent linkage, chelation or ionic interaction. Indirect joining occurs when the immobilized probe is joined to the solid support by one or more linkers. A "linker" is a means for binding at least two different molecules into a stable complex and contains one or more components of a binding partner set.

Members of a binding partner set are able to recognize and bind to each other. Binding partner sets may be, for example, receptor and ligand, enzyme and substrate, enzyme and cofactor, enzyme and coenzyme, antibody and antigen, sugar and lectin, biotin and streptavidin, ligand and chelating agent, nickel and histidine, substantially complementary oligonucleotides, and complementary homopolymeric nucleic acids or homopolymeric portions of polymeric nucleic acids. Components of a binding partner set are the regions of the members that participate in binding.

A preferred sample processing system having practical advantages in terms of its ease of use and rapidity comprises an immobilized probe containing a base sequence which is complementary to a base sequence of a capture probe, referred to herein as an "immobilized probe binding region." The capture probe additionally contains a base sequence, referred to herein as a "target binding region," which may specifically hybridize to a target sequence contained in a target nucleic acid under assay conditions. (While specificity of the target binding region of the capture probe for a region of the target nucleic acid is desirable to minimize the number of non-target nucleic acids remaining from the sample after a separation step, it is not a requirement of the capture probes of the present invention if the capture probes are being used solely to isolate target nucleic acid.) If the capture probe is not being employed to isolate a target nucleic acid for subsequent amplification of a target sequence, the capture probe may further include a detectable label attached within or near the target binding region, such as a substituted or unsubstituted acridinium ester. The labeled capture probe may be used in a homogeneous or semi-homogenous assay to specifically detect hybrid nucleic acids without detecting single-stranded nucleic acids, such as the capture probe. A preferred homogenous assay which could be used with this system is the hybridization protection assay (HPA), which is discussed above in the section entitled "Hybridization Conditions and Probe Design." Following the HPA format, label associated with capture probes which have not hybridized to target nucleic acids would be hydrolyzed with the addition of a mild base, while label associated with capture probe:target hybrids would be protected from hydrolysis.

An advantage of this latter assay system is that only a single target-specific hybridization event (capture probe:target) is necessary for target detection, rather than multiple such events (e.g., capture probe target and probe:target or probe: amplicon) which are required in other sample processing procedures described herein. Also, fewer oligonucleotides in an assay tend to make the assay faster and simpler to optimize, since the overall rate at which a target nucleic acid is captured and detected is limited by the slowest hybridizing oligonucleotide. While the target binding region of a capture probe may be less specific in alternative assay systems, it must still be rare enough to avoid significant saturation of the capture probe with non-target nucleic acids. Thus, the requirement that two separate and specific target sequences be identified in these alternative systems could place constraints on the identification of an appropriate target. By contrast, only one such target sequence is needed when the capture probe simultaneously functions as the detection probe.

Whichever approach is adopted, the assay needs to include means for detecting the presence of the target nucleic acid in the test sample. A variety of means for detecting target nucleic acids are well known to those skilled in the art of nucleic acid detection, including means which do not require the presence of a detectable label. Nevertheless, probes including a detectable label are preferred. A labeled probe for detecting the presence of a target nucleic acid would have to include a base sequence which is substantially complementary and specifically hybridizes to a target sequence contained in the target nucleic acid. Once the probe stably binds to the target nucleic acid, and the resulting target:probe hybrid has been directly or indirectly immobilized, unbound probe can be washed away or inactivated and the remaining bound probe can be detected and/or measured.

Preferred sample processing systems combine the elements of detection and nucleic acid amplification. These systems first directly or indirectly immobilize a target nucleic acid using a capture probe, the captured target nucleic acid is purified by removing inter alia cellular debris, non-target nucleic acid and amplification inhibitors from the sample-containing vessel, which is followed by amplification of a target sequence contained in the target nucleic acid. Amplified product is then detected, preferably in solution with a labeled probe. (The target nucleic acid may remain in the immobilized state during amplification or it may be eluted from the solid support prior to amplification using appropriate conditions, such as by first incubating at a temperature above the $T_m$ of the capture probe:target complex and/or the $T_m$ of the capture probe:immobilized probe complex.) A preferred embodiment of this system is disclosed by Weisburg et al., "Two-Step Hybridization and Capture of a Polynucleotide," U.S. Pat. No. 6,110,678, the contents of which are hereby incorporated by reference herein. In this system, the capture probe hybridizes to the target nucleic acid and an immobilized probe hybridizes to the capture probe:target complex under different hybridization conditions. Under a first set of hybridization conditions, hybridization of the capture probe to the target nucleic acid is favored over hybridization of the capture probe to the immobilized probe. Thus, under this first set of conditions, the capture probe is in solution rather than bound to a solid support, thereby maximizing the concentration of the free capture probe and utilizing favorable liquid phase kinetics for hybridization to the target nucleic acid. After the capture probe has had sufficient time to hybridize to the target nucleic acid, a second set of hybridization conditions is imposed permitting in the capture probe:target complex to hybridize to the immobilized probe, thereby isolating the target nucleic acid in the sample solution. The immobilized target nucleic acid may then be purified, and a target sequence present in the target nucleic acid may be amplified and detected. A purification procedure which includes one or more wash steps is generally desirable when working with crude samples (e.g., clinical samples) to prevent enzyme inhibition and/or nucleic acid degradation due to substances present in the sample.

A preferred amplification method is the transcription-mediated amplification method disclosed by Kacian et al., "Nucleic Acid Sequence Amplification Methods," U.S. Pat. No. 5,480,789, the contents of which are hereby incorporated by reference herein. In accord with this method, a promoter-primer having a 3' region complementary to a portion of the target and a 5' promoter region and a primer having the same nucleotide sequence as a portion of the target are contacted with a target RNA molecule. The primer and promoter-primer define the boundaries of the target region to be amplified, including both the sense present on the target molecule and its complement, and thus the length and sequence of the amplicon. In this preferred embodiment, the amplification oligonucleotides and immobilized target RNA are contacted in the presence of effective amounts of Moloney murine leukemia virus-derived reverse transcriptase and T7 RNA polymerase, both ribonucleotide and deoxyribonucleotide triphosphates, and necessary salts and cofactors at 42° C. Under these conditions, nucleic acid amplification occurs, resulting predominantly in the production of RNA amplicons of a sense opposite to that of the target nucleic acid. These amplicons can then be detected in solution by, for example, using an acridinium ester-labeled hybridization assay probe of the same sense as the target nucleic acid, employing HPA, as disclosed by Arnold et al. in U.S. Pat. No. 5,283,174.

The 3' terminus of the immobilized probe and the capture probe are preferably "capped" or blocked to prevent or inhibit their use as templates for nucleic acid polymerase activity. Capping may involve adding 3' deoxyribonucleotides (such as cordycepin), 3',2'-dideoxynucleotide residues, non-nucleotide linkers, such as those disclosed by Arnold et al. in U.S. Pat. No. 6,031,091, alkane-diol modifications, or non-complementary nucleotide residues at the 3' terminus.

Those skilled in the art will recognize that the above-described methodology is amenable, either as described or with obvious modifications, to various other amplification schemes, including, for example, the polymerase chain reaction (PCR), Qβ replicase-mediated amplification, self-sustained sequence replication (3SR), strand displacement amplification (SDA), nucleic acid sequence-based amplification (NASBA), loop-mediated isothermal amplification (LAMP), and the ligase chain reaction (LCR).

E. Capture Probes for Isolating *Chlamydophila pneumoniae* Ribosomal Nucleic Acid Capture probes of the present invention are designed to bind to and isolate nucleic acid derived from 23 S ribosomal nucleic acid of *C. pneumoniae* in the presence of non-target nucleic acid. As such, the capture probes preferably include both a target binding region and an immobilized probe binding region. The target binding region of the capture probes includes a base sequence which hybridizes to a target sequence contained within the *C. pneumoniae*-derived nucleic acid under assay conditions. While not essential, the target binding region preferably exhibits specificity for the target sequence in the presence of non-target nucleic acid under assay conditions. The immobilized probe binding region has a base sequence which hybridizes to an immobilized probe comprising a polynucleotide, or a chimeric containing polynucleotide sequences, which is joined to a solid support present in the test sample, either directly or indirectly. The target binding region and the immobilized probe binding region may be joined to each other directly or by means of, for example, a nucleotide base sequence, an abasic sequence or a non-nucleotide linker.

In a preferred embodiment, capture probes according to the present invention are up to 100 bases in length and include a target binding region that stably binds to a target sequence that is derived from *C. pneumoniae* 23S ribosomal nucleic acid under assay conditions, where the target sequence is contained within a target region selected from the group consisting of SEQ ID NO:25, SEQ ID NO:26, SEQ ID NO:27 and SEQ ID NO:28. The base sequence of the target binding region preferably comprises, overlaps with, consists essentially of, substantially corresponds to, consists of, or is contained within and includes at least 12, 13, 14 or 15 of 15 contiguous bases of the base sequence selected from the group consisting of SEQ ID NO:29, SEQ ID NO:30, SEQ ID NO:31, SEQ ID NO:32, SEQ ID NO:33, SEQ ID NO:34, SEQ ID NO:35 and SEQ ID NO:36. The immobilized probe binding region of these preferred capture probes comprises a base sequence which hybridizes to an immobilized probe joined directly or indirectly to a solid support provided to the test sample under assay conditions. Preferably, the immobilized probe binding region comprises a homopolymeric region (e.g., poly dA) located at the 3' end of the capture probe which is complementary to a homopolymeric region (e.g., poly dT) located at the 5' end of the immobilized probe. The immobilized probe binding region preferably consists of the base sequence of SEQ ID NO:102 tttaaaaaaaaaaaaaaaaaaaaaaaaaaaaaa. (The tail portion includes a 5'-ttt-3' spacer sequence interposed between the target binding portion and the oligo$(dA)_{30}$ sequence to make the capture probe more flexible for binding to the immobilized probe binding region.) Other base sequences may be incorporated into the immobilized probe binding region, including, for example, short repeating sequences.

To prevent undesirable cross-hybridization reactions, the capture probes of the present invention preferably exclude nucleotide base sequences, other than the nucleotide base sequence of the target binding region, which can stably bind to nucleic acid derived from any organism which may be present in the test sample under assay conditions. Consistent with this approach, and in order to maximize the immobilization of capture probe:target complexes which are formed, the nucleotide base sequence of the immobilized probe binding region is preferably designed so that it can stably bind to a nucleotide base sequence present in the immobilized probe under assay conditions and not to nucleic acid derived from any organism which may be present in the test sample.

The target binding region and the immobilized probe binding region of the capture probe may be selected so that the capture probe:target complex has a higher $T_m$ than the $T_m$, of the capture probe:immobilized probe complex. In this way, a first set of conditions may be imposed which favors hybridization of the capture probe to the target sequence over the immobilized probe, thereby providing for optimal liquid phase hybridization kinetics for hybridization of the capture probe to the target sequence. Once sufficient time has passed for the capture probe to bind to the target sequence, a second set of less stringent conditions may be imposed which allows for hybridization of the capture probe to the immobilized probe.

Capture probes of the present invention may also include a label or a pair of interacting labels for direct detection of the target sequence in a test sample. Non-limiting examples of labels, combinations of labels and means for labeling probes are set forth supra in the section entitled "Preparation of Oligonucleotides" and infra in the section entitled "Detection Probes to *Chlamydophila pneumoniae* Ribosomal Nucleic Acid." A particularly useful method for detecting the presence of a capture probe hybridized to a target nucleic acid is the Hybridization Protection Assay (HPA), which is described above in the section entitled "Hybridization Conditions and Probe Design." HPA is a homogenous assay which distinguishes between probe hybridized to target nucleic acid and probe which remains unhybridized. Signal detected from an HPA reaction vessel provides an indication of the presence or amount of target organisms in the test sample.

Despite their application in a direct detection assay, the most common use of capture probes is in the isolation and purification of target nucleic acid prior to amplifying a target sequence contained in the target nucleic acid. By isolating and purifying the target nucleic acid prior to amplification, the number of unintended amplification reactions (i.e., amplification of non-target nucleic acid) can be severely limited. And, to prevent or inhibit the capture probe itself from functioning as a template for nucleic acid polymerase activity in the presence of amplification reagents and under amplification conditions, the 3' end of the capture probe may be capped or blocked. Examples of capping agents include 3' deoxyribonucleotides, 3',2'-dideoxynucleotide residues, non-nucleotide linkers, alkane-diol modifications, and non-complementary nucleotide residues at the 3' terminus.

F. Detection Probes to *Chlamydophila pneumoniae* Ribosomal Nucleic Acid

This embodiment of the invention relates to novel detection probes. Hybridization is the association of two single strands of complementary nucleic acid to form a hydrogen-bonded double strand. A nucleic acid sequence able to hybridize to a nucleic acid sequence sought to be detected ("target sequence") can serve as a probe for the target sequence. Hybridization may occur between complementary nucleic acid strands, including DNA/DNA, DNA/RNA, and RNA/RNA, as well as between single-stranded nucleic acids wherein one or both strands of the resulting hybrid contain at least one modified nucleotide, nucleoside, nucleobase, and/or base-to-base linkage. In any case, two single strands of sufficient complementarity may hybridize to form a double-stranded structure in which the two strands are held together by hydrogen bonds between pairs of complementary bases. As described above, in general A is hydrogen-bonded to T or U, while G is hydrogen-bonded to C. At any point along the hybridized strands, therefore, the classical base pairs AT or AU, TA or UA, GC, or CG may be found. Thus, when a first single strand of nucleic acid contains sufficient contiguous complementary bases to a second, and those two strands are brought together under conditions that promote their hybridization, double-stranded nucleic acid will result. Accordingly, under appropriate conditions, double-stranded nucleic acid hybrids may be formed.

The rate and extent of hybridization is influenced by a number of factors. For instance, it is implicit that if one of the two strands is wholly or partially involved in a hybrid, it will be less able to participate in the formation of a new hybrid. By designing a probe so that a substantial portion of the sequence of interest is single-stranded, the rate and extent of hybridization may be greatly increased. Also, if the target is an integrated genomic sequence it will naturally occur in a double-stranded form, as is the case with a product of PCR. These double-stranded targets are naturally inhibitory to hybridization with a single-stranded probe and require denaturation (in at least the region to be targeted by the probe) prior to the hybridization step. In addition, there can be intra-molecular and inter-molecular hybrids formed within a probe if there is sufficient self-complementarity. Regions of the nucleic acid known or expected to form strong internal structures inhibitory to hybridization are less preferred. Examples of such structures include hairpin loops. Likewise, probes with extensive self-complementarity generally should be avoided. All these undesirable structures can be avoided through careful probe design, and commercial computer programs are available to search for these types of interactions, such as the Oligo Tech analysis software.

In some applications, however, probes exhibiting at least some degree of self-complementarity are desirable to facilitate detection of probe:target duplexes in a test sample without first requiring the removal of unhybridized probe prior to detection. "Molecular torches" are a type of self-complementary probe that is disclosed by Becker et al., "Molecular Torches," U.S. Pat. No. 6,361,945. Molecular torches have distinct regions of self-complementarity, referred to as "the target binding domain" and "the target closing domain," which are connected by a joining region and which hybridize to one another under predetermined hybridization assay conditions. When exposed to denaturing conditions, the complementary regions (which may be fully or partially complementary) of a molecular torch melt, leaving the target binding domain available for hybridization to a target sequence when the predetermined hybridization assay conditions are restored. And when exposed to strand displacement conditions, a portion of the target sequence binds to the target binding domain and displaces the target closing domain from the target binding domain. Molecular torches are designed so that the target binding domain favors hybridization to the target sequence over the target closing domain. The target binding domain and the target closing domain of a molecular torch include interacting labels (e.g., luminescent/quencher) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label or labels associated therewith.

Another example of detection probes having self-complementarity are the molecular beacons disclosed by Tyagi et al. in U.S. Pat. No. 5,925,517. Molecular beacons include nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open confirmation. The shift to the open confirmation is detectable due to reduced interaction of the label pair, which may be, for example, a fluorophore and quencher, such as DABCYL and EDANS.

The rate at which a probe hybridizes to its target is one measure of the thermal stability of the target secondary structure in the probe region. The standard measurement of hybridization rate is the $C_o t_{1/2}$, which is measured as moles of nucleotide per liter times seconds. Thus, it is the concentration of probe times the time at which 50% of maximal hybridization occurs at that concentration. This value is determined by hybridizing various amounts of probe to a constant amount of target for a fixed time. The $C_o t_{1/2}$ is found graphically by standard procedures. The probe:target hybrid melting temperature may be determined by isotopic methods well-known to those skilled in the art. The melting temperature ($T_m$) for a given hybrid will vary depending on the hybridization solution being used.

Preferred detection probes are sufficiently complementary to the target nucleic acid sequence, or its complement, to hybridize therewith under stringent hybridization conditions corresponding to a temperature of about 60° C. when the salt concentration is in the range of about 0.6-0.9 M. Preferred salts include lithium chloride, but other salts such as sodium chloride and sodium citrate also can be used in the hybridization solution. Examples of high stringency hybridization conditions are alternatively provided by 0.48 M sodium phosphate buffer, 0.1% sodium dodecyl sulfate, and 1 mM each of EDTA and EGTA at a temperature of about 60° C., or by 0.6 M LiCl, 1% lithium lauryl sulfate (LLS), 60 mM lithium succinate and 10 mM each of EDTA and EGTA at a temperature of about 60° C.

Thus, in a first aspect, the present invention features detection probes able to distinguish *C. pneumoniae*-derived nucleic acid from non-*C. pneumoniae* nucleic acid (e.g., *C. trachomatis* and *C. psittaci*) by virtue of the ability of the detection probe to preferentially hybridize to *C. pneumoniae*-derived nucleic acid) under stringent hybridization conditions. Specifically, the detection probes contain an oligonucleotide having a base sequence that is substantially complementary to a target sequence present in *C. pneumoniae*-derived nucleic acid.

In the case of a hybridization assay, the length of the target nucleic acid sequence and, accordingly, the length of the probe sequence can be important. In some cases, there may be several sequences from a particular region, varying in location and length, which will yield probes with the desired hybridization characteristics. In other cases, one sequence may have better hybridization characteristics than another that differs merely by a single base. While it is possible for nucleic acids that are not perfectly complementary to hybridize, the longest stretch of perfectly homologous base sequence will normally primarily determine hybrid stability. While probes of different lengths and base composition may be used, the probes preferred in the present invention are up to 100 bases in length, more preferably from 13 to 35 bases in length, and even more preferably from 15 to 25 bases in length.

The detection probes include a base sequence that is substantially complementary to to a target sequence present in 23S ribosomal RNA (rRNA), or the encoding DNA (rDNA), of *C. pneumoniae*. Thus, the detection probes are able to stably hybridize to a target sequence derived from *C. pneumoniae* under stringent hybridization conditions. The detection probes may also have additional bases outside of the targeted nucleic acid region which may or may not be complementary to *C. pneumoniae*-derived nucleic acid but which are not complementary to nucleic acid derived from a non-target organism which may be present in the test sample.

Probes (and amplification oligonucleotides) of the present invention may also be designed to include a capture tail comprised of a base sequence (distinct from the base sequence intended to hybridize to the target sequence) that can hybridize under predetermined hybridization conditions to a substantially complementary base sequence present in an immobilized oligonucleotide that is joined to a solid support. The immobilized oligonucleotide is preferably joined to a magnetically charged particle that can be isolated in a reaction vessel during a purification step after a sufficient period of time has passed for probe to hybridize to target nucleic acid. (An example of an instrument which can be used to perform such a purification step is the DTS® 400 Target Capture System (Gen-Probe; Cat. No. 5202).) The probe is preferably designed so that the melting temperature of the probe:target hybrid is greater than the melting temperature of the probe: immobilized oligonucleotide hybrid. In this way, different sets of hybridization assay conditions can be employed to facilitate hybridization of the probe to the target nucleic acid prior to hybridization of the probe to the immobilized oligonucleotide, thereby maximizing the concentration of free probe and providing favorable liquid phase hybridization kinetics. This "two-step" target capture method is disclosed by Weisburg et at in U.S. Pat. No. 6,110,678. Other target capture schemes which could be readily adapted to the present invention are well known in the art and include, for example, those disclosed by Ranki et al, "Detection of Microbial Nucleic Acids by a One-Step Sandwich Hybridization Test," U.S. Pat. No. 4,486,539; Stabinsky, "Methods and Kits for Performing Nucleic Acid Hybridization Assays," U.S. Pat. No. 4,751,177; and Boom et al., "Process for Isolating Nucleic Acid," U.S. Pat. No. 5,234,809, each of which references is hereby incorporated by reference herein.

For *C. pneumoniae* detection probes, the terms "target nucleic acid sequence," "target nucleotide sequence," "target sequence," and "target region" all refer to a nucleic acid sequence present in *C. pneumoniae* rRNA or rDNA, or a sequence complementary thereto, which is not identically present in the nucleic acid of a closely related species. Nucleic acids having nucleotide sequences complementary to a target sequence may be generated by target amplification techniques disclosed elsewhere herein.

Organisms closely related to *C. pneumoniae* include *Chlamydia trachomatis* and *Chlamydophila psittaci*. And causes of community acquired pneumonia, in addition to *Chlamydophila pneumoniae*, include *Streptococcus pneumoniae, Staphylococcus aureus, Haemophilus influenzae, Legionella pneumophila, Mycoplasma pneumoniae* and *Coxiella burnetii*. The detection probes of the present invention should be able to distinguish nucleic acid derived from *C. pneumoniae* over nucleic acid derived from any of these organisms. Additionally, the *C. pneumoniae* detection probes of the present invention can be used to distinguish *C. pneumoniae*-derived nucleic acid from any non-*C. pneumoniae* nucleic acid that does not stably hybridize with the probe(s) under stringent hybridization conditions.

In a preferred embodiment of the present invention, *C. pneumoniae* detection probes are preferably up to 100 bases in length and comprise a target binding region which forms a probe:target hybrid stable for detection with a target sequence derived from *C. pneumoniae* 23S ribosomal nucleic acid and contained within a target region selected from the group consisting of SEQ ID NO:1, SEQ ID NO:2, SEQ ID NO:3 and SEQ ID NO:4. More preferably, the base sequence of the target binding region comprises, overlaps with, consists essentially of, substantially corresponds to, consists of, or is contained within and includes at least 12, 13, 14 or 15 of 15 contiguous bases of a base sequence selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23 and SEQ ID NO:24. Even more preferably, the detection probe fully hybridizes to a target sequence substantially corresponding to, consisting of, or contained within the target region. The probe preferentially hybridizes under stringent hybridization conditions to the *C. pneumoniae*-derived target nucleic acid over nucleic acid derived from non-*C. pneumoniae* organisms present in the test sample. In particular, the probe does not form a hybrid stable for detection with *Chlamydia trachomatis* or *Chlamydophila psittaci* under the conditions used.

Once synthesized, the probes may be labeled with a detectable label or reporter group by any well-known method. (See, e.g., SAMBROOK ET AL., supra, ch. 10.) The probe may be labeled with a detectable moiety such as a radioisotope, antigen or chemiluminescent moiety to facilitate detection of the target sequence. Useful labels include radioisotopes as well as non-radioactive reporting groups. Isotopic labels include $^{3}H$, $^{35}S$, $^{32}P$, $^{125}I$, $^{57}Co$ and $^{14}C$. Isotopic labels can be introduced into an oligonucleotide by techniques known in the art such as nick translation, end labeling, second strand synthesis, reverse transcription and by chemical methods. When using radiolabeled probes, hybridization can be detected by techniques such as autoradiography, scintillation counting or gamma counting. The chosen detection method depends on the particular radioisotope used for labeling.

Non-isotopic materials can also be used for labeling and may be introduced internally between nucleotides or at an end of the oligonucleotide. Modified nucleotides may be incorporated enzymatically or chemically. Chemical modifications of the oligonucleotide may be performed during or after synthesis of the oligonucleotide using techniques known in the art. For example, through use of non-nucleotide linker groups disclosed by Arnold et al in U.S. Pat. No. 6,031,091. Non-isotopic labels include fluorescent molecules, chemiluminescent molecules, fluorescent chemiluminescent molecules, phosphorescent molecules, electrochemiluminescent molecules, chromophores, enzymes, enzyme cofactors, enzyme substrates, dyes and haptens or other ligands. Another useful labeling technique is a base sequence that is unable to stably hybridize to the target nucleic acid under stringent conditions. Probes of the present invention are preferably labeled with an acridinium ester. (Acridinium ester labeling is disclosed by Arnold et al. in U.S. Pat. No. 5,185,439.)

The selected detection probe can then be brought into contact with a test sample suspected of containing *C. pneumoniae*. Generally, the test sample is from a source that also contains unknown organisms. Typically, the source of the test sample will be a patient specimen, such as a respiratory specimen. After bringing the probe into contact with nucleic acids derived from the test sample, the probe and sample-derived nucleic acids can be incubated under conditions permitting preferential hybridization of the probe to a target nucleic acid derived from *C. pneumoniae* that may be present in the test sample in the presence of nucleic acid derived from other organisms present in the test sample.

Detection probes may also be combined with one or more unlabeled helper probes to facilitate binding to target nucleic acid derived from *C. pneumoniae*. (See Hogan et al., "Means and Method for Enhancing Nucleic Acid Hybridization," U.S. Pat. No. 5,030,557, the contents of which are hereby incorporated by reference herein.) After a detection probe has hybridized to target nucleic acid present in the test sample, the resulting hybrid may be separated and detected by various techniques well known in the art, such as hydroxyapatite adsorption and radioactive monitoring. Other techniques include those which involve selectively degrading label associated with unhybridized probe and then measuring the amount of remaining label associated with hybridized probe, as disclosed by Arnold et al. in U.S. Pat. No. 5,283,174. The inventors particularly prefer this latter technique.

I. Assay Methods

The present invention contemplates various methods for assaying for the presence or amount of nucleic acid derived from *C. pneumoniae* in a test sample. One skilled in the art will understand that the exact assay conditions, probes, and/or amplification oligonucleotides used will vary depending on the particular assay format used and the source of the sample.

One aspect of the present invention relates to a method for determining the presence or amount of *C. pneumoniae* in a test sample by contacting the test sample, under stringent hybridization conditions, with a detection probe capable of preferentially hybridizing under stringent hybridization conditions to a *C. pneumoniae*-derived target nucleic acid over nucleic acids from non-*C. pneumoniae* organisms present in the test sample. In such methods, detection probes of the present invention are preferably up to 100 bases in length and comprise a target binding region which forms a probe:target hybrid stable for detection with a target sequence derived from 23S ribosomal nucleic acid of *C. pneumoniae* and contained within a target region selected from the group consisting of SEQ ID NO:1, SEQ ID NO:2, SEQ ID NO:3 and SEQ ID NO:4. (Depending on the source, the test sample may contain unknown organisms that the probes of this method can distinguish over.) More preferably, the base sequence of the target binding region comprises, overlaps with, consists essentially of, substantially corresponds to, consists of, or is contained within and includes at least 12, 13, 14 or 15 of 15 contiguous bases of a base sequence selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23 and SEQ ID NO:24. Even more preferably, a detection probe according to this method fully hybridizes to a target sequence substantially corresponding to, consisting of, or contained within the target region. The detection probes may further include a label to facilitate detection in the test sample. In a particularly preferred mode, the detection probes used in the methods of the present invention include acridinium ester labels joined to the probes in accordance with the teachings of Arnold et al. in U.S. Pat. Nos. 5,185,439 and 6,031,091.

Another aspect of the present invention relates to a method for amplifying a target sequence derived from *C. pneumoniae* 23S ribosomal nucleic acid in a test sample by contacting the test sample under amplification conditions with one or more amplification oligonucleotides that will, when contacted with a nucleic acid polymerase, bind to or cause elongation through a nucleic acid region having a base sequence selected from the group consisting of SEQ ID NO:37, SEQ ID NO:38, SEQ ID NO:39, SEQ ID NO:40, SEQ ID NO:73, SEQ ID NO:74, SEQ ID NO:75 and SEQ ID NO:76. Amplification oligonucleotides of this method optionally include a nucleic acid sequence recognized by an RNA polymerase or which enhances initiation or elongation by a RNA polymerase. Particular amplification oligonucleotides and amplification oligonucleotide combinations that can be used in this method are set forth above under the heading "Amplification of *Chlamydophila pneumoniae* Ribosomal Nucleic Acid" and in the Examples below.

In preferred embodiments, the methods for amplifying *C. pneumoniae*-derived nucleic acid in a test sample further include the step of contacting the test sample under stringent hybridization conditions with a detection probe capable of preferentially hybridizing under stringent hybridization conditions to an amplified *C. pneumoniae* target nucleic acid over nucleic acids from non-*C. pneumoniae* organisms present in the test sample. While the test sample is generally contacted with the detection probe after a sufficient period for amplification has passed, the amplification oligonucleotides and detection probe may be added to the sample in any order, as when the detection probe is a self-hybridizing probe, such as a molecular torch discussed supra. This step of contacting the test sample with a detection probe is performed so that the presence or amount of *C. pneumoniae* in the test sample can be determined. Preferred detection probes for use in this method are described in the section entitled "Detection Probes to *Chlamydophila pneumoniae* Ribosomal Nucleic Acid" supra.

Still another aspect of the present invention relates to a method for immobilizing a target nucleic acid derived from *C. pneumoniae* 23S ribosomal nucleic acid in a test sample. Capture probes of the present invention are preferably up to 100 bases in length and comprise a target binding region that stably hybridizes, under assay conditions, to a target sequence that is contained within a target region selected from the group consisting of SEQ ID NO:25, SEQ ID NO:26, SEQ ID NO:27 and SEQ ID NO:28. More preferably, the base sequence of the target binding region comprises, overlaps with, consists essentially of, substantially corresponds to, consists of, or is contained within and includes at least 12, 13, 14 or 15 of 15 contiguous bases of a base sequence selected from the group consisting of SEQ ID NO:29, SEQ ID NO:30, SEQ ID NO:31, SEQ ID NO:32, SEQ ID NO:33, SEQ ID NO:34, SEQ ID NO:35 and SEQ ID NO:36. Even more preferably, a detection probe according to this method fully hybridizes to a target sequence substantially corresponding to, consisting of, or contained within the target region. A purifying step will generally follow the immobilizing step to remove one or more components of the test sample that might interfere with or prevent amplification or specific detection of a target sequence contained in the immobilized target nucleic acid.

The immobilization method of the present invention preferably comprises providing to the test sample a capture probe having a target binding region and an immobilized probe binding region under a first set of hybridization conditions permitting the capture probe to stably bind the target nucleic acid, thereby forming a capture probe:target complex, and a second set of hybridization conditions permitting the capture probe to stably bind to an immobilized probe in the test sample, thereby forming an immobilized probe:capture probe:target complex. The first and second sets of hybridization conditions may be the same or different and the capture probe:target complex remains stable under the second set of hybridization conditions.

This method for immobilizing and optionally purifying a *C. pneumoniae*-derived nucleic may precede any of the methods described above for amplifying and/or detecting the presence of a target nucleic acid derived from *C. pneumoniae*. If a purifying step is included, the target nucleic acid may be indirectly eluted from the immobilized probe or directly eluted from the capture probe of the immobilized probe: capture probe:target complex by altering the sample conditions prior to amplifying or detecting the target sequence.

J. Diagnostic Systems

The present invention also contemplates diagnostic systems in kit form. A diagnostic system of the present invention may include a kit that contains, in an amount sufficient for at least one assay, any of the detection probes, capture probes and/or amplification oligonucleotides of the present invention in a packaging material. Typically, the kits will also include instructions recorded in a tangible form (e.g., contained on paper or an electronic medium, such as a disk, CD-ROM, DVD or video tape) for using the packaged probes and/or amplification oligonucleotides in an amplification and/or detection assay for determining the presence or amount of *C. pneumoniae* in a test sample.

The various components of the diagnostic systems may be provided in a variety of forms. For example, the required enzymes, the nucleotide triphosphates, the probes and/or primers may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present invention may contain a reconstitution reagent for reconstituting the lyophilized reagents of the kit. In preferred kits for amplifying target nucleic acid derived from *C. pneumoniae*, the enzymes, nucleotide triphosphates and required cofactors for the enzymes are provided as a single lyophilized reagent that, when reconstituted, forms a proper reagent for use in the present amplification methods. In these kits, a lyophilized primer reagent may also be provided. In other preferred kits, lyophilized probe reagents are provided.

Typical packaging materials would include solid matrices such as glass, plastic, paper, foil, micro-particles and the like, capable of holding within fixed limits detection probes and/or amplification oligonucleotides of the present invention. Thus, for example, the packaging materials can include glass vials used to contain sub-milligram (e.g., picogram or nanogram) quantities of a contemplated probe or primer, or they can be microtiter plate wells to which probes or primers of the present invention have been operatively affixed, i.e., linked so as to be capable of participating in an amplification and/or detection method of the present invention.

The instructions will typically indicate the reagents and/or concentrations of reagents and at least one assay method parameter that might be, for example, the relative amounts of reagents to use per amount of sample. In addition, such specifics as maintenance, time periods, temperature and buffer conditions may also be included.

The diagnostic systems of the present invention contemplate kits having any of the detection probes, capture probes and/or amplification oligonucleotides described herein, whether provided individually or in one of the preferred combinations described above, for use in amplifying and/or determining the presence or amount of *C. pneumoniae* in a test sample.

EXAMPLES

Examples are provided below illustrating different aspects and embodiments of the invention. It is believed that these examples accurately reflect the details of experiments actually performed, however, it is possible that some minor discrepancies may exist between the work actually performed and the experimental details set forth below which do not affect the conclusions of these experiments. Skilled artisans will appreciate that these examples are not intended to limit the invention to the specific embodiments described therein.

1. Organism Lysis

Whole cells in the examples below were chemically lysed in a transport medium described below in the "Reagents" section as the "Lysis Buffer." This transport medium is a detergent-containing buffered solution which, in addition to lysing cells, protects released RNAs by inhibiting the activity of RNAses present in a test sample.

2. Oligonucleotide Synthesis

Oligonucleotides featured in the examples below include detection probes, helper probes, primers and capture probes. These oligonucleotides were synthesized using standard phosphoramidite chemistry, various methods of which are well known in the art. See, e.g., Caruthers et al., *Methods in Enzymol.,* 154.287 (1987). Synthesis was performed using an Expedite™ 8909 Nucleic Acid Synthesizer (Applied Biosystems, Foster City, Calif.). The detection probes were also synthesized to include a non-nucleotide linker, as disclosed by Arnold et at in U.S. Pat. Nos. 5,585,481 and 5,639,604, and labeled with a chemiluminescent acridinium ester, as disclosed by Arnold et at in U.S. Pat. No. 5,185,439.

3. Transcription-Mediated Amplification

Amplification of a target sequence in the following examples was by a Transcription-Mediated Amplification (TMA) procedure disclosed by, for example, Kacian et at in U.S. Pat. Nos. 5,399,491 and 5,480,784 and by Lee et al., supra, ch. 8. TMA is an isothermal amplification procedure which allows for a greater than one billion-fold increase in copy number of the target sequence using reverse transcriptase and RNA polymerase (see "Enzyme Reagents" below). A TMA reaction involves converting a single-stranded target sequence to a double-stranded DNA intermediate by reverse transcriptase in the presence of a pair of amplification oligonucleotides, one of which has a 5' RNA polymerase-specific promoter sequence. In this embodiment, the DNA intermediate includes a double-stranded promoter sequence which is recognized by a RNA polymerase and directs transcription of the target sequence into hundreds of copies of RNA. Each of these transcribed RNA molecules, in turn, can be converted to a double-stranded DNA intermediate which is used for producing additional RNA. Thus, the TMA reaction proceeds exponentially. The particulars of the TMA reactions used in the following examples are set forth below.

4. Reagents

Various reagents are referenced in the examples below, which include a lysis buffer, a target capture reagent, an amplification reagent, an oil reagent, an enzyme reagent, a hybridization reagent, a selection reagent, and detection reagents. While these reagents are believed to be generally the same for all of the examples which follow, the specific formulations and pH values (where relevant) of the reagents used in Examples 1 and 2 were as follows.

Lysis Buffer. The "Lysis Buffer" contained 15 mM sodium hydroxide, 15 mM NaOH, 1.0 mM EDTA, 1.0 mM EGTA, and 110 mM lithium lauryl sulfate ("LLS").

Target Capture Reagent. The "Target Capture Reagent" contained 250 mM N-2-hydroxyethelpiperazine-N'-2-ethanesulfonic acid ("HEPES"), 310 mM LiOH, 1.88 M LiCl, 100 mM EDTA, adjusted to pH 6.4, and 250 μg/mL Sera-Mag® Magnetic Carboxylate-Modified Microparticles (Seradyn, Inc., Indianapolis, Ind.; Cat. No. 2415-2105) having 5'-amino modified oligo$(dT)_{14}$ covalently bound thereto.

Amplification Reagent. The "Amplification Reagent" was a lyophilized form of a 3.6 mL solution containing 26.7 mM rATP, 5.0 μM-rCTP, 33.3 mM rGTP, 5.0 mM rUTP, 125 mM HEPES, 8% (w/v) trehalose 1.33 mM dATP, 1.33 mM dCTP, 1.33 mM dGTP, 1.33 mM dTTP, 0.003% phenol red, 0.5%, and adjusted to pH 7.5. The Amplification Reagent was reconstituted in 9.7 mL of the Amplification Reagent Reconstitution Solution described below.

Amplification Reagent Reconstitution Solution. The "Amplification Reagent Reconstitution Solution" contained 0.4% (v/v) ethyl alcohol, 0.10% (w/v) methyl paraben, 0.02% (w/v) propyl paraben, 33 mM $KCl_2$, and 30.6 mM $MgCl_2$.

Wash Solution. The "Wash Solution" contained 10 mM HEPES, 6.5 mM NaOH, 1 mM EDTA, 0.3% (v/v) ethyl alcohol, 0.02% (w/v) methyl paraben, 0.01% (w/v) propyl paraben, 150 mM NaCl, and 0.1% (w/v) sodium lauryl sulfate, adjusted to pH 7.5.

Enzyme Reagent. The "Enzyme Reagent" was a lyophilized form of a 1.45 mL enzyme reagent solution containing 900 RTU/μL Moloney murine leukemia virus ("MMLV") reverse transcriptase and 200 U/μL T7 RNA polymerase in an enzyme lyophilization buffer made up of 20 mM HEPES, 125 mM N-acetyl-L-cysteine ("NALC"), 0.1 mM EDTA, 0.2% (v/v) TRITON® X-100 detergent, and 0.2 M trehalose, adjusted to pH 7.0. (One "unit" or "RTU" of activity is defined as the synthesis and release of 5.75 fmol cDNA in 15 minutes at 37° C. for MMLV reverse transcriptase, and for T7 RNA polymerase, one "unit" or "U" of activity is defined as the production of 5.0 fmol RNA transcript in 20 minutes at 37° C.) The Enzyme Reagent was reconstituted in 3.6 mL of the Enzyme Reagent Reconstitution Solution described below.

Enzyme Reagent Reconstitution Solution. The "Enzyme Reagent Reconstitution Solution" contained 50 mM HEPES, 1 mM EDTA, 10% (v/v) TRITON® X-100 detergent, 120 mM $KCl_2$, and 20% (v/v) glycerol, adjusted to pH 7.0.

Hybridization Reagent. The "The Hybridization Reagent" contained 100 mM succinic acid, 2% (w/v) LLS, 100 mM LiOH, 15 mM aldrithiol-2, 1.2 M $LiCl_2$, 20 mM EDTA, and 3.0% (v/v) ethyl alcohol, adjusted to pH 4.7.

Selection Reagent. The "Selection Reagent" contained 600 mM boric acid, 182.5 mM NaOH, pellets, and 1% (v/v) TRITON® X-100 detergent, adjusted to pH 8.5.

Detection Reagents. The "Detection Reagents" of the following examples comprised Detect Reagent I, which contained 1 mM $HNO_3$ and 32 mM $H_2O_2$, 30% (v/v), and Detect Reagent II, which contained 1.575 M NaOH, pellets.

Oil Reagent. The "Oil Reagent" of the following examples was a silicone oil (United Chemical Technologies, Inc., Bristol, Pa.; Cat. No. PS038).

Example 1

Specificity of a *C. pneumoniae* Amplification Assay

This experiment was conducted to determine the sensitivity and specificity of an amplification assay targeting a 23 S region of *C. pneumoniae* mRNA over nucleic acid derived from numerous non-target bacteria, including the closely related species of *Chlamydia trachomatis* and *Chlamydophila abortus*, which is derived from *Chlamydophila psittaci*. For each amount of organisms or rRNA tested, test samples were prepared in replicates of two. Three replicates of a negative control were also prepared and tested.

The test samples and negative controls were initially set up in the reaction tubes of Ten-Tube Units (Gen-Probe Incorporated, San Diego, Calif.; Cat. No. TU0022) by combining 100 μL of the Target Capture Reagent with 400 μL of the Lysis Buffer. For each test sample, the Lysis Buffer further contained the amounts of organisms or rRNA indicated in Table 1 below. The Target Capture Reagent contained 2.5 pmol of a target capture probe having the sequence of SEQ ID NO:103 gctaaagttttaggtggtacaggtttaaaaaaaaaaaaaaaaaaaaaaaaaaaaaa. This capture probe includes a 5' target binding region (SEQ ID NO:33) and a 3' immobilized probe binding region (SEQ ID NO:102). (The immobilized probe binding region includes a 5'-ttt-3' spacer sequence interposed between the target binding portion and the oligo$(dA)_{30}$ sequence to make the capture probe more flexible for binding to the immobilized oligo$(dT)_{14}$.) The reaction tubes were covered with a sealing card (Gen-Probe; Cat. No. 2085), hand-shaken, and incubated for 30 minutes at 62° C. to permit hybridization of the target binding region of the capture probe to the target nucleic acid. Following this incubation, the reaction tubes were vortexed for 60 seconds and then cooled for 30 minutes at room temperature to facilitate hybridization of the oligo $(dA)_{30}$ sequence of the immobilized probe binding region of the capture probe to oligo$(dT)_{14}$ bound to the magnetic particles. After cooling the samples, a DTSO® 400 Target Capture System (Gen-Probe; Cat. No. 5202) was used to isolate and wash the magnetic particles. The DTS® 400 Target Capture System has a test tube bay for positioning Ten-Tube Test Units ("TTUs") and applying magnetic fields to the reaction tubes. The TTUs were placed in the test tube bay on the DTS® 400 Target Capture System for 5 minutes in the presence of the magnetic fields to isolate the magnetic particles within the reaction tubes before aspirating sample material from the TTUs. Each reaction tube was then provided with 1 mL of the Wash Solution, covered with a sealing card and vortexed to resuspend the magnetic particles. The TTUs were returned to the test tube bay on the DTSO® 400 Target Capture System and allowed to stand at room temperature for 5 minutes before the Wash Solution was aspirated.

Following target capture, a 75 μL aliquot of the reconstituted Amplification Reagent was added to each reaction tube. Each aliquot of the reconstituted Amplification Reagent was spiked with 14 pmol of a primer having the sequence of SEQ ID NO:81 and 20 pmol of a promoter-primer having the sequence of SEQ ID NO:104 aatttaatacgactcactatagggagacacactat cagttcctccgaag. The promoter-primer included a 3' target-binding portion (SEQ ID NO:45) and a 5' T7 promoter sequence (SEQ ID NO:97). The reaction tubes were then provided with 200 μL of the Oil Reagent, covered with a sealing card, and vortexed for 10 seconds before being incubated for 10 minutes at 62° C. for an initial anneal step to promote binding of the promoter-primers to the target nucleic acid. The reaction tubes were then incubated for another 5 minutes at 42° C. before adding 25 μL of the reconstituted Enzyme Reagent to each reaction tube. The reaction tubes were again covered with a sealing card and their contents were gently mixed by hand. After mixing, the reaction tubes were incubated for 60 minutes at 42° C.

For detection of *C. pneumoniae* amplification products, 100 μL of the Hybridization Reagent containing 20 fmol of a detection probe was added to each reaction tube. The detection probe had the base sequence of SEQ ID NO:105 gcuaacacaaggucg (a 2'-O-methyl modified version of SEQ ID NO:6) and a standard acridinium ester label joined to the probe by means of a non-nucleotide linker positioned between nucleotides 8 and 9, reading 5' to 3'. The reaction tubes were covered with a sealing card, vortexed for 10 seconds, and then incubated for 20 minutes at 62° C. to allow hybridization of the detection probe to amplification products present in the reaction tubes. The reaction tubes were then cooled for 5 minutes at room temperature before adding 250 μL of the Selection Reagent to each reaction tube. The reaction tubes were again covered with a sealing card, vortexed for 10 seconds, and then incubated for another 10 minutes at 62° C. to hydrolyze acridinium ester labels associated with unhybridized probe. The reaction tubes were then allowed to cool for 15 minutes at room temperature before being analyzed in a LEADER® HC+Luminometer (Gen-Probe; Cat. No. 4747) equipped with automatic injection of Detection Reagent 1, followed by automatic injection of Detection Reagent 2. The cut-off for a negative result in this experiment was 50,000 RLU.

The results of this experiment are summarized in Table 1 below and indicate that the *C. pneumoniae* assay being tested amplified and detected *C. pneumoniae*-derived nucleic acid without cross-reacting with nucleic acid derived from *C. trachomatis, C. abortus*, or any of the other bacteria tested. The term "RLU" in this table stands for relative light units.

TABLE 1

Specificity and Sensitivity of the *C. pneumoniae* Amplification Assay

| Organism | ATCC No. | Amount | Avg. RLU |
|---|---|---|---|
| Negative Control | N/A | N/A | 1082 |
| *Chlamydophila pneumoniae* | VR-2282 | 40 Organisms | 1,095,664 |
| *Chlamydia Trachomatis* | VR-878 | 0.144 μg rRNA | 1934 |
| *Chlamydophila abortus* | VR-656 | 0.04 μg rRNA | 2312 |

TABLE 1-continued

Specificity and Sensitivity of the *C. pneumoniae* Amplification Assay

| Organism | ATCC No. | Amount | Avg. RLU |
|---|---|---|---|
| *Streptococcus agalactiae* | 13813 | 10E+6 Organisms | 906 |
| | | 10E+4 Organisms | 1223 |
| *Enterococcus* sp. | 102361 | 10E+6 Organisms | 1147 |
| | | 10E+4 Organisms | 1036 |
| *Streptococcus sanguis* | 10566 | 10E+6 Organisms | 1141 |
| | | 10E+4 Organisms | 1011 |
| *Corynebacterium xerosis* | 373 | 10E+6 Organisms | 1145 |
| | | 10E+4 Organisms | 1147 |
| *Streptococcus pyogenes* | 12344 | 10E+6 Organisms | 1128 |
| | | 10E+4 Organisms | 1153 |
| *Corynebacterium jeikeium* | 43734 | 10E+6 Organisms | 1000 |
| | | 10E+4 Organisms | 1094 |
| *Corynebacterium striatum* | 6940 | 10E+6 Organisms | 1137 |
| | | 10E+4 Organisms | 1150 |
| *Staphylococcus epidermidis* | 14990 | 10E+6 Organisms | 1159 |
| | | 10E+4 Organisms | 848 |
| *Leifsonia aquatica* | 14665 | 10E+6 Organisms | 1180 |
| | | 10E+4 Organisms | 1043 |
| *Streptococcus dysgalactiae* | 27957 | 10E+6 Organisms | 1111 |
| | | 10E+4 Organisms | 1131 |
| *Haemophilus parainfluenzae* | 33392 | 10E+6 Organisms | 1088 |
| | | 10E+4 Organisms | 1109 |
| *Haemophilus influenzae* | 33533 | 10E+6 Organisms | 1147 |
| | | 10E+4 Organisms | 1162 |
| *Escherichia coli* | 29214 | 10E+6 Organisms | 1115 |
| | | 10E+4 Organisms | 1003 |
| *Pseudomonas aeruginosa* | Clinical | 10E+6 Organisms | 1168 |
| | Isolate | 10E+4 Organisms | 1118 |
| *Streptococcus mitis* | 33399 | 10E+6 Organisms | 1024 |
| | | 10E+4 Organisms | 1099 |
| *Moraxella catarrhalis* | 25238 | 10E+6 Organisms | 854 |
| | | 10E+4 Organisms | 1079 |
| *Streptococcus bovis* | 35034 | 10E+6 Organisms | 984 |
| | | 10E+4 Organisms | 1023 |
| *Klebsiella pneumoniae* | 23357 | 10E+6 Organisms | 1078 |
| | | 10E+4 Organisms | 918 |
| *Streptococcus pneumoniae* | 35088 | 10E+6 Organisms | 1048 |
| | | 10E+4 Organisms | 1082 |

Example 2

Comparison of Two *C. pneumoniae* Detection Probes

The purpose of this experiment was to determine which of two detection probes best differentiates between *C. pneumoniae, C. trachomatis* and *C. psittaci*. The detection probes of this experiment included the detection probe of Example 1 ("Probe 1") and a detection probe having the sequence of SEQ ID NO:21 and a standard acridinium ester label joined to the probe by means of a non-nucleotide linker positioned between nucleotides 7 and 8, reading 5' to 3' ("Probe 2"). In the detection step of this experiment, probe hybridized to amplification products was selected for by adding 250 μL of the Selection Reagent to each reaction tube and incubating the samples for 5, 10, 15 or 20 minutes at 62° C. The samples were tested in replicates of five for each selection time. At the conclusion of each selection period, the reaction tubes of that time group were stored on ice, and all reaction tubes were stored on ice for additional 5 minutes at the completion of all selection times. The reaction tubes were then warmed at room temperature for 10 minutes before hybridized probe was detected in the manner set forth in Example 1. Except for the concentrations of the detection probes (0.1 pmol/sample) and primers (15 pmol/sample non-T7 primer and 15 pmol/sample T7 promoter-primer), the remainder of the reagents, materials, and procedures of this experiment were substantially the same as those set forth in Example 1.

The results of this experiment are set forth in Tables 2 and 3 below and show strong RLU values for both probes hybridized to *C. pneumoniae* amplicon. The cut-off for a negative result in this experiment was 50,000 RLU. Thus, Probe 1 exhibited cross-reactivity with *C. trachomatis* and *C. psittaci* at the 5 minute selection time, and Probe 2 exhibited cross-reactivity with *C. psittaci* at the 5 and 10 minute selection times. While these results show that both probes are capable of specifically detecting *C. pneumoniae*, Probe 1 was determined to be best. It is expected that both probes would exhibit better specificity at a selection temperature of 62° C.

TABLE 2

Specificity of Probe 1 for *C. pneumoniae* Amplicon

| Selection Time | Organism | Source | Amount | Avg. RLU |
|---|---|---|---|---|
| 5 | Negative Control | N/A | N/A | 8595 |
|  | C. pneumoniae | ATCC No. VR-2282 | 10E+4 Organisms | 5,298,443 |
|  | C. trachomatis | Internal Stock | 1 ng rRNA/10 μL | 127,285 |
|  | C. psittaci | ATCC No. VR-601 | 10E+4 Organisms | 290,659 |
| 10 | Negative Control | N/A | N/A | 4369 |
|  | C. pneumoniae | ATCC No. VR-2282 | 10E+4 Organisms | 4,735,585 |
|  | C. trachomatis | Internal Stock | 1 ng rRNA/10 μL | 10,824 |
|  | C. psittaci | ATCC No. VR-601 | 10E+4 Organisms | 11,435 |
| 15 | Negative Control | N/A | N/A | 4055 |
|  | C. pneumoniae | ATCC No. VR-2282 | 10E+4 Organisms | 3,949,153 |
|  | C. trachomatis | Internal Stock | 1 ng rRNA/10 μL | 10,529 |
|  | C. psittaci | ATCC No. VR-601 | 10E+4 Organisms | 6797 |
| 20 | Negative Control | N/A | N/A | 4672 |
|  | C. pneumoniae | ATCC No. VR-2282 | 10E+4 Organisms | 3,590,383 |
|  | C. trachomatis | Internal Stock | 1 ng rRNA/10 μL | 7169 |
|  | C. psittaci | ATCC No. VR-601 | 10E+4 Organisms | 7073 |

TABLE 3

Specificity of Probe 2 for *C. pneumoniae* Amplicon

| Selection Time | Organism | Source | Amount | Mean RLU |
|---|---|---|---|---|
| 5 | Negative Control | N/A | N/A | 9034 |
|  | C. pneumoniae | ATCC No. VR-2282 | 10E+4 Organisms | 4,047,409 |
|  | C. trachomatis | Internal Stock | 1 ng rRNA/10 μL | 9422 |
|  | C. psittaci | ATCC No. VR-601 | 10E+4 Organisms | 772,396 |
| 10 | Negative Control | N/A | N/A | 10,158 |
|  | C. pneumoniae | ATCC No. VR-2282 | 10E+4 Organisms | 3,987,735 |
|  | C. trachomatis | Internal Stock | 1 ng rRNA/10 μL | 8309 |
|  | C. psittaci | ATCC No. VR-601 | 10E+4 Organisms | 103,937 |
| 15 | Negative Control | N/A | N/A | 4028 |
|  | C. pneumoniae | ATCC No. VR-2282 | 10E+4 Organisms | 2,848,006 |
|  | C. trachomatis | Internal Stock | 1 ng rRNA/10 μL | 5038 |
|  | C. psittaci | ATCC No. VR-601 | 10E+4 Organisms | 16,443 |
| 20 | Negative Control | N/A | N/A | 4889 |
|  | C. pneumoniae | ATCC No. VR-2282 | 10E+4 Organisms | 2,014,033 |
|  | C. trachomatis | Internal Stock | 1 ng rRNA/10 μL | 7128 |
|  | C. psittaci | ATCC No. VR-601 | 10E+4 Organisms | 7188 |

Example 3

Specificity of a *C. pneumoniae* Amplification Assay

The purpose of this experiment was to determine the specificity of another amplification assay targeting a 23S region of *C. pneumoniae* rRNA. For this experiment, RNA from eleven different organisms, including *C. pneumoniae* and closely related *C trachomatis* and *C psittaci*, was tested at three different concentrations in replicates of two. Three replicates of a negative control were also run with this *C. pneumoniae* amplification assay.

The test samples and negative controls were initially set up in the reaction tubes of TTUs (Gen-Probe; Cat. No. TU0022) by combining 200 μL of a target capture reagent with 400 μL of a detergent-containing transport medium. The test samples were spiked with RNA transcript in the amounts indicated in Table 4 below. The target capture reagent contained magnetically responsive particles having bound oligo(dT) sequences and 5 pmol of a capture probe having the sequence of SEQ ID NO:106   gctccatcgtctacgcatttgtgctttaaaaaaaaaaaaaaaaaaa aaaaaaaaaaa, which included a 5' target binding region (SEQ ID NO:33) and a 3' immobilized probe binding region (SEQ ID NO:102). The contents of the reaction tubes were mixed and incubated for 10 minutes at 60° C. to allow hybridization of the target binding region of the capture probe to the target nucleic acid. The samples were then cooled at room temperature for 5 minutes to allow the oligo(dA)$_{30}$ sequences of the capture probe to hybridize to the oligo(dT) sequences of the magnetically responsive particles. To isolate the magnetically responsive particles, the reaction tubes were exposed to magnetic fields for 10 minutes using a DTSO® 400 Target Capture System, as described in Example 1, before aspirating sample material from the reaction tubes. The magnetically responsive particles were washed by adding 1 mL of a buffered wash solution to each reaction tube, vortexing, subjecting the contents of the reaction tubes to magnetic fields of the DTSO® 400 Target Capture System for another 5 minutes, and then aspirating the buffered wash solution from each reaction tube. This wash procedure was repeated one time.

After the target capture step, 75 μL of an amplification reagent was added to each reaction tube. The amplification reagent included 15 pmol each of a primer having the sequence of SEQ ID NO:77 and a T7 promoter-primer having the sequence of SEQ ID NO:107 aatttaatacgactcactatagg-gagaccttgcgccacactatc, which included a 3' target-binding portion having the sequence of SEQ ID NO:65 and a 5' T7 promoter sequence (SEQ ID NO:97). The amplification reagent also included rNTPs, dNTPs, salts, buffers, and cofactors needed for amplifying the *C. pneumoniae* target sequence in a TMA reaction. Each reaction tube was then provided with 100 μL of a silicone oil and vortexed before being incubated for 10 minutes at 60° C. for an initial anneal step to promote binding of the promoter-primers to the target nucleic acid. Following the initial anneal step, the reaction tubes were incubated for 5 minutes at 42° C. before adding 25 μL of an enzyme reagent containing a reverse transcriptase and a T7 RNA polymerase to each reaction tube. The contents of the reaction tubes were then hand-mixed and incubated for 60 minutes at 42° C.

Following amplification, a 100 μL of a probe reagent containing 10 pmol of a detection probe having a 2'-O-methyl modified version of the sequence of SEQ ID NO:108 caa ugagacugguuaguag and an acridinium ester label joined to the probe by means of a non-nucleotide linker positioned between nucleotides 9 and 10, reading 5' to 3'. The reaction tubes were incubated for 20 minutes at 60° C. to permit hybridization of the detection probe to amplification products present in the reaction tubes. Afterwards, 300 μL of a selection reagent was added to each reaction tube. The reaction tubes were then incubated for 10 minutes at 60° C. to hydrolyze acridinium ester labels associated with unhybridized probe. The contents of the reaction tubes were then cooled on ice for 1 minute before being analyzed in a LEADER® 450hc Luminometer equipped with automatic injection of reagents for detecting acridinium ester labels associated with hybridized probe.

The results of this experiment are set forth in Table 4 below and show cross-reactivity of this assay with the *C. trachomatis* RNA. Additionally, the RLU values associated with the *C. pneumoniae* RNA suggest that this assay has low sensitivity for the targeted nucleic acid.

TABLE 4

Specificity of *C. pneumoniae* Amplification Assay

| Organism | Total RNA Input | Avg. RLU |
|---|---|---|
| Negative Control | N/A | 2136 |
| *Mycoplasma pneumoniae* | 50 fg | 2140 |
| | 5 fg | 1752 |
| | 0.5 fg | 2529 |
| *Mycoplasma fermentans* | 50 pg | 2502 |
| | 5 pg | 2037 |
| | 500 fg | 2955 |
| *Mycoplasma gallisepticum* | 50 pg | 3227 |
| | 5 pg | 1895 |
| | 500 fg | 1618 |
| *Mycoplasma genitallium* | 50 pg | 1362 |
| | 5 pg | 1486 |
| | 500 fg | 1982 |
| *Mycoplasma hominis* | 50 pg | 1616 |
| | 5 pg | 2485 |
| | 500 fg | 2383 |
| *Mycoplasma orale* | 50 pg | 2172 |
| | 5 pg | 4241 |
| | 500 fg | 1817 |
| *Streptococcus pneumoniae* | 50 pg | 1473 |
| | 5 pg | 2809 |
| | 500 fg | 2060 |
| *Ureaplasma urealyticum* | 50 pg | 2666 |
| | 5 pg | 3045 |
| | 500 fg | 4480 |
| *Chlamydophila pneumoniae* | 5 pg | 877,746 |
| | 500 fg | 481,972 |
| | 50 fg | 185,535 |
| *Chlamydophila psittaci* | 50 pg | 11,816 |
| | 5 pg | 16,615 |
| | 500 fg | 12,851 |
| *Chlamydia trachomatis* | 50 pg | 170,953 |
| | 5 pg | 65,451 |
| | 500 fg | 24,164 |

Example 4

Effectiveness of Various Primer Sets at Amplifying *C. pneumoniae* 23S rRNA

This experiment was designed to evaluate the performance of various primer sets at amplifying a *C. pneumoniae* 23S rRNA target sequence. Samples were tested in replicates of four and had either 200 or 2000 copies of a transcript containing the *C. pneumoniae* target sequence. Also included was a negative control tested in replicates of two for each primer set evaluated.

Reaction tubes were initially set up to include 200 μL of a target capture reagent and 400 μL of a detergent-containing transport medium having 0, 200 or 2000 copies of the transcript. The target capture reagent included magnetically responsive particles having bound oligo(dT) sequences and the capture probe of Example 1. The contents of the reaction tubes were mixed and incubated for 10 minutes at 60° C. to allow hybridization of the target binding region of the capture probe to the target nucleic acid. The samples were then cooled at room temperature for 10 minutes to allow the oligo$(dA)_{30}$ sequences of the capture probe to hybridize to the oligo(dT) sequences of the magnetically responsive particles. To isolate the magnetically responsive particles, the reaction tubes were exposed to a magnetic field for 10 minutes using a DTSO®400 Target Capture System, as described in Example 1. Sample material was then aspirated from the reaction tubes and the magnetically responsive particles were washed twice with a buffered wash solution.

Following the target capture procedure, each reaction tube was provided with 75 μL of an amplification reagent containing rNTPs, dNTPs, salts, buffers, cofactors, and a primer set for amplifying the *C. pneumoniae* target sequence. Each primer set included 15 pmol each of a non-T7 primer and a T7 promoter-primer for use in a TMA reaction. The primer sets were divided into Groups A-D, with each group including a primer and five different promoter-primers. Group A included a primer having the sequence of SEQ ID NO:81, Group B included a primer having the sequence of SEQ ID NO:85, Group C included a primer having the sequence of SEQ ID NO:89, and Group D included a primer having the sequence of SEQ ID NO:93. The primer of each of Groups A-D was separately tested in combination with each of the following promoter-primers:

```
SEQ ID NO: 104
aatttaatacgactcactatagggagacacactatcagttcctccgaag
("Promoter-Primer 1");

SEQ ID NO: 109
aatttaatacgactcactatagggagagcgccacactatcagttc
("Promoter-Primer 2");

SEQ ID NO: 110
aatttaatacgactcactatagggagaccttgcgccacactatcagttc
("Promoter-Primer 3");

SEQ ID NO: 111
aatttaatacgactcactatagggagaccttgcgccacactatc
("Promoter-Primer 4");
and

SEQ ID NO: 112
aatttaatacgactcactatagggagagaaagccttgcgccacactat
("Promoter-Primer 5").
```

Each of the promoter-primers included a 3' target-binding portion and a 5' T7 promoter sequence (SEQ ID NO:97). The target-binding portions of SEQ ID Nos. 104 and 109-112 had the sequences of SEQ ID Nos. 45, 53, 57, 65 and 69, respectively. After adding the amplification reagent, 200 μL of a silicone oil was added to each reaction tube, and the samples were vortexed before being incubated for 10 minutes at 60° C. to initiate binding of the promoter-primers to the transcript. This was followed by a 5 minute incubation at 42° C., after which each reaction tube was provided with 25 μL of an enzyme reagent containing a reverse transcriptase and a T7 RNA polymerase. The samples were then incubated for 60 minutes at 42° C.

To detect *C. pneumoniae* amplification products, each reaction tube received 100 μL of a probe reagent containing 10 pmol of the detection probe having the sequence of SEQ ID NO:108 and an acridinium ester label joined to the probe by means of a non-nucleotide linker positioned between nucleotides 9 and 10, reading 5' to 3'. The reaction tubes were incubated for 20 minutes at 60° C. to permit hybridization of the detection probe to amplification products present in the reaction tubes. Afterwards, 300 μL of a selection reagent was added to each reaction tube. The reaction tubes were then incubated for 10 minutes at 60° C. to hydrolyze acridinium ester labels associated with unhybridized probe. The contents of the reaction tubes were then cooled on ice for 1 minute before being analyzed in a LEADER® 450hc Luminometer equipped with automatic injection of reagents for detecting acridinium ester labels associated with hybridized probe.

The results of this experiment are set forth in Table 5 below and show that the primers of Groups A and C and the promoter-primers having the sequences of SEQ ID Nos. 104, 109 and 110 performed best. Other combinations that performed well were the primer of Group A in combination with the promoter-primer having the sequence of SEQ ID NO:112, and the primer of Group D in combination with the promoter-primers having the sequences of SEQ ID Nos. 104, 109 and 112.

TABLE 5

Performance of *C. pneumoniae* Primer Sets

| Primer Set | | Signal in Relative Light Units (RLU) | | |
|---|---|---|---|---|
| Primer Set Group | Promoter-Primer | Negative Control | 200 Copies Transcript | 2000 Copies Transcript |
| A | 1 | 2662 | 1,096,106 | 4,006,808 |
| | 2 | 3812 | 1,348,048 | 3,929,352 |
| | 3 | 2395 | 1,175,357 | 4,167,669 |
| | 4 | 15,528 | 8833 | 791,064 |
| | 5 | 2686 | 2439 | 2,322,786 |
| B | 1 | 3060 | 24,546 | 1,269,208 |
| | 2 | 4069 | 12,328 | 989,117 |
| | 3 | 5681 | 6459 | 627,281 |
| | 4 | 64,402 | 319,594 | 67,557 |
| | 5 | 5099 | 3805 | 76,491 |
| C | 1 | 5328 | 23,760 | 3,351,216 |
| | 2 | 12,778 | 162,241 | 4,133,638 |
| | 3 | 4200 | 84,428 | 2,469,481 |
| | 4 | 291,911 | 134,662 | 520,551 |
| | 5 | 5824 | 3156 | 1,307,266 |
| D | 1 | 4138 | 3649 | 2,590,635 |
| | 2 | 5974 | 47,380 | 4,157,073 |
| | 3 | 3415 | 7380 | 1,299,714 |
| | 4 | 20,020 | 21,648 | 105,204 |
| | 5 | 4660 | 18,709 | 2,734,940 |

Example 5

Effect of Varying Primer Concentration on Amplification of *C. pneumoniae* 23S rRNA This experiment was designed to evaluate the performance of preferred primer sets of Example 4 at varying primer concentrations. The procedure was substantially the same as that of Example 4, except that the primer sets and negative controls were tested in replicates of five and only samples containing 2000 copies of the 23rRNA *C. pneumoniae* transcript were tested. Additionally, the Group A sets of primers described below were tested using the capture probe of Example 4, while tests involving the Group B sets of primers described below used a capture probe having the sequence of SEQ ID NO:113 gctccatcgtctacgcatttgtgctt-taaaaaaaaaaaaaaaaaaaaaaaaa aaaaa, which included a 5' target binding region (SEQ ID NO:29) and a 3' immobilized probe binding region (SEQ ID NO:102).

The Group A sets of primers tested included a non-T7 primer having the sequence of SEQ ID NO:81 in combination with a T7 promoter-primer having the sequence of SEQ ID NO:104 ("Promoter-Primer 1"), SEQ ID NO:109 ("Promoter-Primer 2"), or SEQ ID NO:110 ("Promoter-Primer 3"). The Group B sets of primers tested included a non-T7 primer having the sequence of SEQ ID NO:89 in combination with Promoter-Primer 2 or Promoter-Primer 3 of the Group A sets of primers. The negative control signal for the primer combinations averaged 2,089 RLU. The remainder of the results of this experiment are presented in Tables 6 and 7 below, which show that the non-T7 primer of Group A performed better than the non-T7 primer of Group B at each primer concentration tested. The results also indicate that better amplification results can be achieved using higher concentrations of either non-T7 primer (between 15 and 30 pmol).

TABLE 6

Performance of Group A Primer Sets in Amplifying *C. pneumoniae* 23S rRNA

| Primer Concentrations | Signal in Relative Light Units (RLU) | | |
|---|---|---|---|
| (Primer/Promoter-Primer) | Promoter-Primer 1 | Promoter-Primer 2 | Promoter-Primer 3 |
| 3 pmol/3 pmol | 1,619,727 | 1,080,112 | 2,696,778 |
| 3 pmol/15 pmol | 2,542,466 | 2,099,013 | 1,723,142 |
| 3 pmol/30 pmol | 1,173,753 | 1,087,449 | 1,029,686 |
| 15 pmol/15 pmol | 2,701,186 | 2,910,068 | 2,963,372 |
| 30 pmol/3 pmol | 2,574,541 | 2,766,368 | 2,459,222 |
| 30 pmol/15 pmol | 2,826,894 | 2,889,268 | 2,998,225 |
| 30 pmol/30 pmol | 2,830,232 | 2,808,374 | 2,712,769 |

TABLE 7

Performance of Group B Primer Sets in Amplifying *C. pneumoniae* 23S rRNA

| Primer Concentrations (Primer/Promoter- | Signal in Relative Light Units (RLU) | |
|---|---|---|
| Primer) | Promoter-Primer 2 | Promoter-Primer 3 |
| 3 pmol/3 pmol | 2,299 | 118,372 |
| 3 pmol/15 pmol | 258,020 | 51,572 |
| 3 pmol/30 pmol | 45,990 | 30,021 |
| 15 pmol/15 pmol | 1,872,782 | 781,421 |
| 30 pmol/3 pmol | 2,080 | 1,591,081 |
| 30 pmol/15 pmol | 750,580 | 1,272,457 |
| 30 pmol/30 pmol | 2,098,994 | 862,345 |

* * * * *

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

The invention claimed is:

1. A detection probe for use in determining the presence of *Chlamydophila pneumoniae* in a test sample, said probe being up to 50 bases in length and comprising a target binding region that forms a probe:target hybrid stable for detection with a target sequence contained within a target region selected from the group consisting of SEQ ID NO:1, SEQ ID NO:2, SEQ ID NO:3 and SEQ ID NO:4 under stringent hybridization conditions, wherein said target binding region comprises the nucleotide base sequence of SEQ ID NO:13, SEQ ID NO:14, SEQ ID NO:15 or SEQ ID NO:16, and wherein said probe does not form a hybrid stable for detection with nucleic acid derived from *Chlamydia trachomatis* or *Chlamydophila psittaci* under said conditions.

2. The detection probe of claim 1, wherein said probe is up to 40 bases in length.

3. The detection probe of claim 1, wherein said probe is up to 35 bases in length.

4. The detection probe of claim 1, wherein said probe is up to 30 bases in length.

5. The detection probe of claim 1, wherein said probe is up to 25 bases in length.

6. The detection probe of claim 1, wherein said probe fully hybridizes to said target region.

7. The detection probe of claim 6, wherein said target binding region consists of the base sequence of SEQ ID NO:13, SEQ ID NO:14, SEQ ID NO:15 or SEQ ID NO:16.

8. The detection probe of claim 1, wherein the base sequence of said probe consists of the base sequence of SEQ ID NO:13, SEQ ID NO:14, SEQ ID NO:15 or SEQ ID NO:16.

9. The detection probe of claim 1, wherein said probe includes a detectable label.

10. The detection probe of claim 1, wherein said probe is a self-hybridizing probe under said conditions and in the absence of said target sequence.

11. The detection probe of claim 1, wherein said probe comprises a pair of interacting labels.

12. The detection probe of claim 1,wherein said target binding region includes at least one 2'-O-methyl ribonucleotide.

13. The detection probe of claim 1, wherein said conditions include a temperature of about 60° C. and a salt concentration of about 0.6 M to about 0.9 M.

14. A composition comprising said probe of claim 1 hybridized to nucleic acid derived from *Chlamydophila pneumoniae* under said conditions.

15. A method for determining the presence of *Chlamydophila pneumoniae* in a test sample, said method comprising the steps of:

(a) contacting a test sample with said probe of claim 1 under said conditions; and (b) determining whether said probe:target hybrid is present in said test sample as indication of the presence of *Chlamydophila pneumoniae* in said test sample.

16. The method of claim 15, wherein said probe is up to 40 bases in length.

17. The method of claim 15, wherein said probe is up to 35 bases in length.

18. The method of claim 15, wherein said probe is up to 30 bases in length.

19. The method of claim 15, wherein said probe is up to 25 bases in length.

20. The method of claim 15, wherein said probe fully hybridizes to said target region.

21. The method of claim 20, wherein said target binding region consists of the base sequence of SEQ ID NO:13, SEQ ID NO:14, SEQ ID NO:15 or SEQ ID NO:16.

22. The method of claim 15, wherein the base sequence of said probe consists of the base sequence of SEQ ID NO:13, SEQ ID NO:14, SEQ ID NO:15 or SEQ ID NO:16.

23. The method of claim 15, wherein said probe includes a detectable label.

24. The method of claim 15, wherein said probe is a self-hybridizing probe under said conditions and in the absence of said target sequence.

25. The method of claim 24, wherein said probe comprises a pair of interacting labels.

26. The method of claim 15, wherein said target binding region includes at least one 2'-O-methyl ribonucleotide.

* * * * *

SEQUENCE LISTING

```
<160> NUMBER OF SEQ ID NOS: 113

<210> SEQ ID NO 1
<211> LENGTH: 32
<212> TYPE: DNA
<213> ORGANISM: Chlamydophila pneumoniae

<400> SEQUENCE: 1

gctaacacaa ggtcgggttg tggttaaggg aa                                   32


<210> SEQ ID NO 2
<211> LENGTH: 32
<212> TYPE: RNA
<213> ORGANISM: Chlamydophila pneumoniae

<400> SEQUENCE: 2

gcuaacacaa ggucggguug ugguuaaggg aa                                   32


<210> SEQ ID NO 3
<211> LENGTH: 32
<212> TYPE: DNA
<213> ORGANISM: Chlamydophila pneumoniae

<400> SEQUENCE: 3

ttcccttaac cacaacccga ccttgtgtta gc                                   32


<210> SEQ ID NO 4
<211> LENGTH: 32
<212> TYPE: RNA
<213> ORGANISM: Artificial
<220> FEATURE:
<223> OTHER INFORMATION: Sequence derived from 23S rRNA of Chlamydophila
      pneumoniae

<400> SEQUENCE: 4

uucccuuaac cacaacccga ccuuguguua gc                                   32


<210> SEQ ID NO 5
<211> LENGTH: 15
<212> TYPE: DNA
<213> ORGANISM: Chlamydophila pneumoniae

<400> SEQUENCE: 5

gctaacacaa ggtcg                                                      15


<210> SEQ ID NO 6
<211> LENGTH: 15
<212> TYPE: RNA
<213> ORGANISM: Chlamydophila pneumoniae

<400> SEQUENCE: 6

gcuaacacaa ggucg                                                      15


<210> SEQ ID NO 7
<211> LENGTH: 15
<212> TYPE: DNA
<213> ORGANISM: Chlamydophila pneumoniae
```

-continued

<400> SEQUENCE: 7
cgaccttgtg ttagc 15

<210> SEQ ID NO 8
<211> LENGTH: 15
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 8
cgaccuugug uuagc 15

<210> SEQ ID NO 9
<211> LENGTH: 20
<212> TYPE: DNA
<213> ORGANISM: Chlamydophila pneumoniae

<400> SEQUENCE: 9
gctaacacaa ggtcgggttg 20

<210> SEQ ID NO 10
<211> LENGTH: 20
<212> TYPE: RNA
<213> ORGANISM: Chlamydophila pneumoniae

<400> SEQUENCE: 10
gcuaacacaa ggucggguug 20

<210> SEQ ID NO 11
<211> LENGTH: 20
<212> TYPE: DNA
<213> ORGANISM: Chlamydophila pneumoniae

<400> SEQUENCE: 11
caacccgacc ttgtgttagc 20

<210> SEQ ID NO 12
<211> LENGTH: 20
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 12
caacccgacc uuguguuagc 20

<210> SEQ ID NO 13
<211> LENGTH: 21
<212> TYPE: DNA
<213> ORGANISM: Chlamydophila pneumoniae

<400> SEQUENCE: 13
caaggtcggg ttgtggttaa g 21

<210> SEQ ID NO 14
<211> LENGTH: 21
<212> TYPE: RNA
<213> ORGANISM: Chlamydophila pneumoniae

<400> SEQUENCE: 14
caaggucggg uugugguuaa g 21

-continued

<210> SEQ ID NO 15
<211> LENGTH: 21
<212> TYPE: DNA
<213> ORGANISM: Chlamydophila pneumoniae

<400> SEQUENCE: 15
cttaaccaca acccgacctt g 21

<210> SEQ ID NO 16
<211> LENGTH: 21
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 16
cuuaaccaca acccgaccuu g 21

<210> SEQ ID NO 17
<211> LENGTH: 23
<212> TYPE: DNA
<213> ORGANISM: Chlamydophila pneumoniae

<400> SEQUENCE: 17
caaggtcggg ttgtggttaa ggg 23

<210> SEQ ID NO 18
<211> LENGTH: 23
<212> TYPE: RNA
<213> ORGANISM: Chlamydophila pneumoniae

<400> SEQUENCE: 18
caaggucggg uugugguuaa ggg 23

<210> SEQ ID NO 19
<211> LENGTH: 23
<212> TYPE: DNA
<213> ORGANISM: Chlamydophila pneumoniae

<400> SEQUENCE: 19
cccttaacca caacccgacc ttg 23

<210> SEQ ID NO 20
<211> LENGTH: 23
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 20
cccuuaacca caacccgacc uug 23

<210> SEQ ID NO 21
<211> LENGTH: 25
<212> TYPE: DNA
<213> ORGANISM: Chlamydophila pneumoniae

<400> SEQUENCE: 21
caaggtcggg ttgtggttaa gggaa 25

<210> SEQ ID NO 22

-continued

<211> LENGTH: 25
<212> TYPE: RNA
<213> ORGANISM: Chlamydophila pneumoniae

<400> SEQUENCE: 22
caaggucggg uugugguuaa gggaa 25

<210> SEQ ID NO 23
<211> LENGTH: 25
<212> TYPE: DNA
<213> ORGANISM: Chlamydophila pneumoniae

<400> SEQUENCE: 23
ttcccttaac cacaacccga ccttg 25

<210> SEQ ID NO 24
<211> LENGTH: 25
<212> TYPE: RNA
<213> ORGANISM: Artificial
<220> FEATURE:
<223> OTHER INFORMATION: Sequence derived from 23S rRNA of Chlamydophila
pneumoniae

<400> SEQUENCE: 24
uucccuuaac cacaacccga ccuug 25

<210> SEQ ID NO 25
<211> LENGTH: 33
<212> TYPE: DNA
<213> ORGANISM: Chlamydophila pneumoniae

<400> SEQUENCE: 25
gttaaatatt cctgtaccac ctaaaacttt agc 33

<210> SEQ ID NO 26
<211> LENGTH: 33
<212> TYPE: RNA
<213> ORGANISM: Chlamydophila pneumoniae

<400> SEQUENCE: 26
guuaaauauu ccuguaccac cuaaaacuuu agc 33

<210> SEQ ID NO 27
<211> LENGTH: 33
<212> TYPE: DNA
<213> ORGANISM: Chlamydophila pneumoniae

<400> SEQUENCE: 27
gctaaagttt taggtggtac aggaatattt aac 33

<210> SEQ ID NO 28
<211> LENGTH: 33
<212> TYPE: RNA
<213> ORGANISM: Artificial
<220> FEATURE:
<223> OTHER INFORMATION: Sequence derived from 23S rRNA of Chlamydophila
pneumoniae

<400> SEQUENCE: 28
gcuaaaguuu uaggugguac aggaauauuu aac 33

<210> SEQ ID NO 29
<211> LENGTH: 27
<212> TYPE: DNA
<213> ORGANISM: Chlamydophila pneumoniae -continued

<400> SEQUENCE: 29
gttttaggtg gtacaggaat atttaac 27

<210> SEQ ID NO 30
<211> LENGTH: 27
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 30
guuuuaggug guacaggaau auuuaac 27

<210> SEQ ID NO 31
<211> LENGTH: 27
<212> TYPE: DNA
<213> ORGANISM: Chlamydophila pneumoniae

<400> SEQUENCE: 31
gttaaatatt cctgtaccac ctaaaac 27

<210> SEQ ID NO 32
<211> LENGTH: 27
<212> TYPE: RNA
<213> ORGANISM: Chlamydophila pneumoniae

<400> SEQUENCE: 32
guuaaauauu ccuguaccac cuaaaac 27

<210> SEQ ID NO 33
<211> LENGTH: 23
<212> TYPE: DNA
<213> ORGANISM: Chlamydophila pneumoniae

<400> SEQUENCE: 33
gctaaagttt taggtggtac agg 23

<210> SEQ ID NO 34
<211> LENGTH: 23
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 34
gcuaaaguuu uaggugguac agg 23

<210> SEQ ID NO 35
<211> LENGTH: 23
<212> TYPE: DNA
<213> ORGANISM: Chlamydophila pneumoniae

<400> SEQUENCE: 35
cctgtaccac ctaaaacttt agc 23

<210> SEQ ID NO 36
<211> LENGTH: 23
<212> TYPE: RNA
<213> ORGANISM: Chlamydophila pneumoniae

<400> SEQUENCE: 36

-continued

```
ccuguaccac cuaaaacuuu agc                                              23


<210> SEQ ID NO 37
<211> LENGTH: 50
<212> TYPE: DNA
<213> ORGANISM: Chlamydophila pneumoniae

<400> SEQUENCE: 37

gtggttaagg gaaatcttcg gaggaactga tagtgtggcg caaggctttc                 50


<210> SEQ ID NO 38
<211> LENGTH: 50
<212> TYPE: RNA
<213> ORGANISM: Chlamydophila pneumoniae

<400> SEQUENCE: 38

gugguuaagg gaaaucuucg gaggaacuga uaguguggcg caaggcuuuc                 50


<210> SEQ ID NO 39
<211> LENGTH: 50
<212> TYPE: DNA
<213> ORGANISM: Chlamydophila pneumoniae

<400> SEQUENCE: 39

gaaagccttg cgccacacta tcagttcctc cgaagatttc ccttaaccac                 50


<210> SEQ ID NO 40
<211> LENGTH: 50
<212> TYPE: RNA
<213> ORGANISM: Artificial
<220> FEATURE:
<223> OTHER INFORMATION: Sequence derived from 23S rRNA of Chlamydophila
      pneumoniae

<400> SEQUENCE: 40

gaaagccuug cgccacacua ucaguuccuc cgaagauuuc ccuuaaccac                 50


<210> SEQ ID NO 41
<211> LENGTH: 23
<212> TYPE: DNA
<213> ORGANISM: Chlamydophila pneumoniae

<400> SEQUENCE: 41

ctccgaagat ttcccttaac cac                                              23


<210> SEQ ID NO 42
<211> LENGTH: 23
<212> TYPE: RNA
<213> ORGANISM: Artificial
<220> FEATURE:
<223> OTHER INFORMATION: Sequence derived from 23S rRNA of Chlamydophila
      pneumoniae

<400> SEQUENCE: 42

cuccgaagau uucccuuaac cac                                              23


<210> SEQ ID NO 43
<211> LENGTH: 23
<212> TYPE: DNA
<213> ORGANISM: Chlamydophila pneumoniae

<400> SEQUENCE: 43

gtggttaagg gaaatcttcg gag                                              23
```

-continued

<210> SEQ ID NO 44
<211> LENGTH: 23
<212> TYPE: RNA
<213> ORGANISM: Chlamydophila pneumoniae

<400> SEQUENCE: 44
gugguuaagg gaaaucuucg gag 23

<210> SEQ ID NO 45
<211> LENGTH: 22
<212> TYPE: DNA
<213> ORGANISM: Chlamydophila pneumoniae

<400> SEQUENCE: 45
cacactatca gttcctccga ag 22

<210> SEQ ID NO 46
<211> LENGTH: 22
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 46
cacacuauca guuccuccga ag 22

<210> SEQ ID NO 47
<211> LENGTH: 22
<212> TYPE: DNA
<213> ORGANISM: Chlamydophila pneumoniae

<400> SEQUENCE: 47
cttcggagga actgatagtg tg 22

<210> SEQ ID NO 48
<211> LENGTH: 22
<212> TYPE: RNA
<213> ORGANISM: Chlamydophila pneumoniae

<400> SEQUENCE: 48
cuucggagga acugauagug ug 22

<210> SEQ ID NO 49
<211> LENGTH: 19
<212> TYPE: DNA
<213> ORGANISM: Chlamydophila pneumoniae

<400> SEQUENCE: 49
ccacactatc agttcctcc 19

<210> SEQ ID NO 50
<211> LENGTH: 19
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 50
ccacacuauc aguuccucc 19

<210> SEQ ID NO 51
<211> LENGTH: 19
<212> TYPE: DNA

-continued

<213> ORGANISM: Chlamydophila pneumoniae

<400> SEQUENCE: 51
ggaggaactg atagtgtgg 19

<210> SEQ ID NO 52
<211> LENGTH: 19
<212> TYPE: RNA
<213> ORGANISM: Chlamydophila pneumoniae

<400> SEQUENCE: 52
ggaggaacug auagugugg 19

<210> SEQ ID NO 53
<211> LENGTH: 18
<212> TYPE: DNA
<213> ORGANISM: Chlamydophila pneumoniae

<400> SEQUENCE: 53
gcgccacact atcagttc 18

<210> SEQ ID NO 54
<211> LENGTH: 18
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 54
gcgccacacu aucaguuc 18

<210> SEQ ID NO 55
<211> LENGTH: 18
<212> TYPE: DNA
<213> ORGANISM: Chlamydophila pneumoniae

<400> SEQUENCE: 55
gaactgatag tgtggcgc 18

<210> SEQ ID NO 56
<211> LENGTH: 18
<212> TYPE: RNA
<213> ORGANISM: Chlamydophila pneumoniae

<400> SEQUENCE: 56
gaacugauag uguggcgc 18

<210> SEQ ID NO 57
<211> LENGTH: 22
<212> TYPE: DNA
<213> ORGANISM: Chlamydophila pneumoniae

<400> SEQUENCE: 57
ccttgcgcca cactatcagt tc 22

<210> SEQ ID NO 58
<211> LENGTH: 22
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 58
ccuugcgcca cacuaucagu uc 22

<210> SEQ ID NO 59
<211> LENGTH: 22
<212> TYPE: DNA
<213> ORGANISM: Chlamydophila pneumoniae

<400> SEQUENCE: 59
gaactgatag tgtggcgcaa gg 22

<210> SEQ ID NO 60
<211> LENGTH: 22
<212> TYPE: RNA
<213> ORGANISM: Chlamydophila pneumoniae

<400> SEQUENCE: 60
gaacugauag uguggcgcaa gg 22

<210> SEQ ID NO 61
<211> LENGTH: 18
<212> TYPE: DNA
<213> ORGANISM: Chlamydophila pneumoniae

<400> SEQUENCE: 61
cttgcgccac actatcag 18

<210> SEQ ID NO 62
<211> LENGTH: 18
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 62
cuugcgccac acuaucag 18

<210> SEQ ID NO 63
<211> LENGTH: 18
<212> TYPE: DNA
<213> ORGANISM: Chlamydophila pneumoniae

<400> SEQUENCE: 63
ctgatagtgt ggcgcaag 18

<210> SEQ ID NO 64
<211> LENGTH: 18
<212> TYPE: RNA
<213> ORGANISM: Chlamydophila pneumoniae

<400> SEQUENCE: 64
cugauagugu ggcgcaag 18

<210> SEQ ID NO 65
<211> LENGTH: 17
<212> TYPE: DNA
<213> ORGANISM: Chlamydophila pneumoniae

<400> SEQUENCE: 65
ccttgcgcca cactatc 17

<210> SEQ ID NO 66
<211> LENGTH: 17

-continued

<212> TYPE: RNA
<213> ORGANISM: Artificial
<220> FEATURE:
<223> OTHER INFORMATION: Sequence derived from 23S rRNA of Chlamydophila
pneumoniae

<400> SEQUENCE: 66
ccuugcgcca cacuauc 17

<210> SEQ ID NO 67
<211> LENGTH: 17
<212> TYPE: DNA
<213> ORGANISM: Chlamydophila pneumoniae

<400> SEQUENCE: 67
gatagtgtgg cgcaagg 17

<210> SEQ ID NO 68
<211> LENGTH: 17
<212> TYPE: RNA
<213> ORGANISM: Chlamydophila pneumoniae

<400> SEQUENCE: 68
gauagugugg cgcaagg 17

<210> SEQ ID NO 69
<211> LENGTH: 21
<212> TYPE: DNA
<213> ORGANISM: Chlamydophila pneumoniae

<400> SEQUENCE: 69
gaaagccttg cgccacacta t 21

<210> SEQ ID NO 70
<211> LENGTH: 21
<212> TYPE: RNA
<213> ORGANISM: Artificial
<220> FEATURE:
<223> OTHER INFORMATION: Sequence derived from 23S rRNA of Chlamydophila
pneumoniae

<400> SEQUENCE: 70
gaaagccuug cgccacacua u 21

<210> SEQ ID NO 71
<211> LENGTH: 21
<212> TYPE: DNA
<213> ORGANISM: Chlamydophila pneumoniae

<400> SEQUENCE: 71
atagtgtggc gcaaggcttt c 21

<210> SEQ ID NO 72
<211> LENGTH: 21
<212> TYPE: RNA
<213> ORGANISM: Chlamydophila pneumoniae

<400> SEQUENCE: 72
auaguguggc gcaaggcuuu c 21

<210> SEQ ID NO 73
<211> LENGTH: 33
<212> TYPE: DNA
<213> ORGANISM: Chlamydophila pneumoniae -continued

<400> SEQUENCE: 73
cggagtacgt taagcacgcg gacgattgga aat 33

<210> SEQ ID NO 74
<211> LENGTH: 33
<212> TYPE: RNA
<213> ORGANISM: Chlamydophila pneumoniae

<400> SEQUENCE: 74
cggaguacgu uaagcacgcg gacgauugga aau 33

<210> SEQ ID NO 75
<211> LENGTH: 33
<212> TYPE: DNA
<213> ORGANISM: Chlamydophila pneumoniae

<400> SEQUENCE: 75
atttccaatc gtccgcgtgc ttaacgtact ccg 33

<210> SEQ ID NO 76
<211> LENGTH: 33
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 76
auuuccaauc guccgcgugc uuaacguacu ccg 33

<210> SEQ ID NO 77
<211> LENGTH: 33
<212> TYPE: DNA
<213> ORGANISM: Chlamydophila pneumoniae

<400> SEQUENCE: 77
cggagtacgt taagcacgcg gacgattgga aat 33

<210> SEQ ID NO 78
<211> LENGTH: 33
<212> TYPE: RNA
<213> ORGANISM: Chlamydophila pneumoniae

<400> SEQUENCE: 78
cggaguacgu uaagcacgcg gacgauugga aau 33

<210> SEQ ID NO 79
<211> LENGTH: 33
<212> TYPE: DNA
<213> ORGANISM: Chlamydophila pneumoniae

<400> SEQUENCE: 79
atttccaatc gtccgcgtgc ttaacgtact ccg 33

<210> SEQ ID NO 80
<211> LENGTH: 33
<212> TYPE: RNA
<213> ORGANISM: Artificial
<220> FEATURE:
<223> OTHER INFORMATION: Sequence derived from 23S rRNA of Chlamydophila pneumoniae

<400> SEQUENCE: 80
auuuccaauc guccgcgugc uuaacguacu ccg 33

-continued

<210> SEQ ID NO 81
<211> LENGTH: 17
<212> TYPE: DNA
<213> ORGANISM: Chlamydophila pneumoniae

<400> SEQUENCE: 81
cggagtacgt taagcac 17

<210> SEQ ID NO 82
<211> LENGTH: 17
<212> TYPE: RNA
<213> ORGANISM: Chlamydophila pneumoniae

<400> SEQUENCE: 82
cggaguacgu uaagcac 17

<210> SEQ ID NO 83
<211> LENGTH: 17
<212> TYPE: DNA
<213> ORGANISM: Chlamydophila pneumoniae

<400> SEQUENCE: 83
gtgcttaacg tactccg 17

<210> SEQ ID NO 84
<211> LENGTH: 17
<212> TYPE: DNA
<213> ORGANISM: Artificial
<220> FEATURE:
<223> OTHER INFORMATION: Sequence derived from 23S rRNA of Chlamydophila pneumoniae

<400> SEQUENCE: 84
gtgcttaacg tactccg 17

<210> SEQ ID NO 85
<211> LENGTH: 26
<212> TYPE: DNA
<213> ORGANISM: Chlamydophila pneumoniae

<400> SEQUENCE: 85
gagtacgtta agcacgcgga cgattg 26

<210> SEQ ID NO 86
<211> LENGTH: 26
<212> TYPE: RNA
<213> ORGANISM: Chlamydophila pneumoniae

<400> SEQUENCE: 86
gaguacguua agcacgcgga cgauug 26

<210> SEQ ID NO 87
<211> LENGTH: 26
<212> TYPE: DNA
<213> ORGANISM: Chlamydophila pneumoniae

<400> SEQUENCE: 87
caatcgtccg cgtgcttaac gtactc 26

<210> SEQ ID NO 88
<211> LENGTH: 26
<212> TYPE: RNA
<213> ORGANISM: Artificial

-continued

```
<220> FEATURE:
<223> OTHER INFORMATION: Sequence derived from 23S rRNA of Chlamydophila
      pneumoniae

<400> SEQUENCE: 88

caaucguccg cgugcuuaac guacuc                                          26


<210> SEQ ID NO 89
<211> LENGTH: 20
<212> TYPE: DNA
<213> ORGANISM: Chlamydophila pneumoniae

<400> SEQUENCE: 89

gttaagcacg cggacgattg                                                 20


<210> SEQ ID NO 90
<211> LENGTH: 20
<212> TYPE: RNA
<213> ORGANISM: Chlamydophila pneumoniae

<400> SEQUENCE: 90

guuaagcacg cggacgauug                                                 20


<210> SEQ ID NO 91
<211> LENGTH: 20
<212> TYPE: DNA
<213> ORGANISM: Chlamydophila pneumoniae

<400> SEQUENCE: 91

caatcgtccg cgtgcttaac                                                 20


<210> SEQ ID NO 92
<211> LENGTH: 20
<212> TYPE: RNA
<213> ORGANISM: Artificial
<220> FEATURE:
<223> OTHER INFORMATION: Sequence derived from 23S rRNA of Chlamydophila
      pneumoniae

<400> SEQUENCE: 92

caaucguccg cgugcuuaac                                                 20


<210> SEQ ID NO 93
<211> LENGTH: 21
<212> TYPE: DNA
<213> ORGANISM: Chlamydophila pneumoniae

<400> SEQUENCE: 93

gttaagcacg cggacgattg g                                               21


<210> SEQ ID NO 94
<211> LENGTH: 21
<212> TYPE: RNA
<213> ORGANISM: Chlamydophila pneumoniae

<400> SEQUENCE: 94

guuaagcacg cggacgauug g                                               21


<210> SEQ ID NO 95
<211> LENGTH: 21
<212> TYPE: DNA
<213> ORGANISM: Chlamydophila pneumoniae

<400> SEQUENCE: 95
```

-continued

```
ccaatcgtcc gcgtgcttaa c                                                21


<210> SEQ ID NO 96
<211> LENGTH: 21
<212> TYPE: RNA
<213> ORGANISM: Artificial
<220> FEATURE:
<223> OTHER INFORMATION: Sequence derived from 23S rRNA of Chlamydophila
      pneumoniae

<400> SEQUENCE: 96

ccaaucgucc gcgugcuuaa c                                                21


<210> SEQ ID NO 97
<211> LENGTH: 27
<212> TYPE: DNA
<213> ORGANISM: Artificial
<220> FEATURE:
<223> OTHER INFORMATION: T7 RNA polymerase promoter sequence

<400> SEQUENCE: 97

aatttaatac gactcactat agggaga                                          27


<210> SEQ ID NO 98
<211> LENGTH: 139
<212> TYPE: DNA
<213> ORGANISM: Chlamydophila pneumoniae

<400> SEQUENCE: 98

cggagtacgt taagcacgcg gacgattgga aatgtccgta tcacaatgag actggttagt      60

aggcaaatcc gctaacacaa ggtcgggttg tggttaaggg aaatcttcgg aggaactgat     120

agtgtggcgc aaggctttc                                                  139


<210> SEQ ID NO 99
<211> LENGTH: 139
<212> TYPE: RNA
<213> ORGANISM: Chlamydophila pneumoniae

<400> SEQUENCE: 99

cggaguacgu uaagcacgcg gacgauugga aauguccgua ucacaaugag acugguuagu      60

aggcaaaucc gcuaacacaa ggucggguug ugguuaaggg aaaucuucgg aggaacugau     120

aguguggcgc aaggcuuuc                                                  139


<210> SEQ ID NO 100
<211> LENGTH: 139
<212> TYPE: DNA
<213> ORGANISM: Chlamydophila pneumoniae

<400> SEQUENCE: 100

gcctcatgca attcgtgcgc ctgctaacct ttacaggcat agtgttactc tgaccaatca      60

tccgtttagg cgattgtgtt ccagcccaac accaattccc tttagaagcc tccttgacta     120

tcacaccgcg ttccgaaag                                                  139


<210> SEQ ID NO 101
<211> LENGTH: 139
<212> TYPE: RNA
<213> ORGANISM: Artificial
<220> FEATURE:
<223> OTHER INFORMATION: Sequence derived from 23 rRNA of Chlamydophila
      pneumoniae

<400> SEQUENCE: 101
```

-continued

```
gccucaugca auucgugcgc cugcuaaccu uuacaggcau aguguuacuc ugaccaauca     60

uccguuuagg cgauuguguu ccagcccaac accaauuccc uuuagaagcc uccuugacua    120

ucacaccgcg uuccgaaag                                                 139


<210> SEQ ID NO 102
<211> LENGTH: 33
<212> TYPE: DNA
<213> ORGANISM: Artificial
<220> FEATURE:
<223> OTHER INFORMATION: Immobilized probe binding region sequence of a
      capture probe

<400> SEQUENCE: 102

tttaaaaaaa aaaaaaaaaa aaaaaaaaaa aaa                                  33


<210> SEQ ID NO 103
<211> LENGTH: 56
<212> TYPE: DNA
<213> ORGANISM: Artificial
<220> FEATURE:
<223> OTHER INFORMATION: Capture probe sequence for binding and
      isolating 23S rRNA of Chlamydophila pneumoniae

<400> SEQUENCE: 103

gctaaagttt taggtggtac aggtttaaaa aaaaaaaaaa aaaaaaaaaa aaaaaa         56


<210> SEQ ID NO 104
<211> LENGTH: 49
<212> TYPE: DNA
<213> ORGANISM: Artificial
<220> FEATURE:
<223> OTHER INFORMATION: Promoter-primer sequence for binding and
      amplifying 23S rRNA of Chlamydophila pneumoniae

<400> SEQUENCE: 104

aatttaatac gactcactat agggagacac actatcagtt cctccgaag                 49


<210> SEQ ID NO 105
<211> LENGTH: 15
<212> TYPE: RNA
<213> ORGANISM: Artificial
<220> FEATURE:
<223> OTHER INFORMATION: Detection probe sequence for binding and
      detecting sequence derived from 23S rRNA of Chlamydophila
      pneumoniae
<220> FEATURE:
<221> NAME/KEY: misc_feature
<222> LOCATION: (1)..(15)
<223> OTHER INFORMATION: 2'-O-methyl ribonucleotides

<400> SEQUENCE: 105

gcuaacacaa ggucg                                                      15


<210> SEQ ID NO 106
<211> LENGTH: 57
<212> TYPE: DNA
<213> ORGANISM: Artificial
<220> FEATURE:
<223> OTHER INFORMATION: Capture probe sequence for binding and
      isolating 23S rRNA of Chlamydophila pneumoniae

<400> SEQUENCE: 106

gctccatcgt ctacgcattt gtgctttaaa aaaaaaaaaa aaaaaaaaaa aaaaaaa        57


<210> SEQ ID NO 107
```

-continued

<211> LENGTH: 44
<212> TYPE: DNA
<213> ORGANISM: Artificial
<220> FEATURE:
<223> OTHER INFORMATION: Promoter-primer sequence for binding and amplifying 23S rRNA of Chlamydophila pneumoniae

<400> SEQUENCE: 107
aatttaatac gactcactat agggagacct tgcgccacac tatc 44

<210> SEQ ID NO 108
<211> LENGTH: 19
<212> TYPE: RNA
<213> ORGANISM: Artificial
<220> FEATURE:
<223> OTHER INFORMATION: Detection probe sequence for binding and detecting sequence derived from 23S rRNA of Chlamydophila pneumoniae
<220> FEATURE:
<221> NAME/KEY: misc_feature
<222> LOCATION: (1)..(19)
<223> OTHER INFORMATION: 2'-O-methyl ribonucleotides

<400> SEQUENCE: 108
caaugagacu gguuaguag 19

<210> SEQ ID NO 109
<211> LENGTH: 45
<212> TYPE: DNA
<213> ORGANISM: Artificial
<220> FEATURE:
<223> OTHER INFORMATION: Promoter-primer sequence for binding and amplifying 23S rRNA of Chlamydophila pneumoniae

<400> SEQUENCE: 109
aatttaatac gactcactat agggagagcg ccacactatc agttc 45

<210> SEQ ID NO 110
<211> LENGTH: 49
<212> TYPE: DNA
<213> ORGANISM: Artificial
<220> FEATURE:
<223> OTHER INFORMATION: Promoter-primer sequence for binding and amplifying 23S rRNA of Chlamydophila pneumoniae

<400> SEQUENCE: 110
aatttaatac gactcactat agggagacct tgcgccacac tatcagttc 49

<210> SEQ ID NO 111
<211> LENGTH: 44
<212> TYPE: DNA
<213> ORGANISM: Artificial
<220> FEATURE:
<223> OTHER INFORMATION: Promoter-primer sequence for binding and amplifying 23S rRNA of Chlamydophila pneumoniae

<400> SEQUENCE: 111
aatttaatac gactcactat agggagacct tgcgccacac tatc 44

<210> SEQ ID NO 112
<211> LENGTH: 48
<212> TYPE: DNA
<213> ORGANISM: Artificial
<220> FEATURE:
<223> OTHER INFORMATION: Promoter-primer sequence for binding and amplifying 23S rRNA of Chlamydophila pneumoniae

<400> SEQUENCE: 112

-continued

```
aatttaatac gactcactat agggagagaa agccttgcgc cacactat           48


<210> SEQ ID NO 113
<211> LENGTH: 60
<212> TYPE: DNA
<213> ORGANISM: Artificial
<220> FEATURE:
<223> OTHER INFORMATION: Capture probe sequence for binding and
      isolating 23S rRNA of Chlamydophila pneumoniae

<400> SEQUENCE: 113

gttttaggtg gtacaggaat atttaacttt aaaaaaaaaa aaaaaaaaaa aaaaaaaaaa     60
```